US012703695B2

(12) United States Patent
Turchi et al.

(10) Patent No.: US 12,703,695 B2
(45) Date of Patent: Aug. 11, 2026

(54) KU INHIBITORS AND THEIR USE

(71) Applicant: INDIANA UNIVERSITY RESEARCH AND TECHNOLOGY CORPORATION, Indianapolis, IN (US)

(72) Inventors: John J Turchi, Indianapolis, IN (US); Navnath Gavande, Indianapolis, IN (US); Pamela S. Vandervere-Carozza, Zionsville, IN (US)

(73) Assignee: INDIANA UNIVERSITY RESEARCH AND TECHNOLOGY CORPORATION, Indianapolis, IN (US)

( * ) Notice: Subject to any disclaimer, the term of this patent is extended or adjusted under 35 U.S.C. 154(b) by 1323 days.

(21) Appl. No.: 17/388,906

(22) Filed: Jul. 29, 2021

(65) Prior Publication Data

US 2022/0089577 A1 Mar. 24, 2022

Related U.S. Application Data

(62) Division of application No. 16/303,454, filed as application No. PCT/US2017/034254 on May 24, 2017, now Pat. No. 11,098,033.

(60) Provisional application No. 62/340,639, filed on May 24, 2016.

(51) Int. Cl.

| | |
|---|---|
| ***C07D 405/14*** | (2006.01) |
| ***A61K 31/41*** | (2006.01) |
| ***A61K 31/4155*** | (2006.01) |
| ***A61P 43/00*** | (2006.01) |
| ***C07D 405/06*** | (2006.01) |
| ***C07D 409/06*** | (2006.01) |
| ***C12N 5/10*** | (2006.01) |
| ***C12N 9/22*** | (2006.01) |
| ***C12N 9/78*** | (2006.01) |
| ***C12N 15/11*** | (2006.01) |
| ***C12N 15/87*** | (2006.01) |
| ***C12N 15/90*** | (2006.01) |

(52) U.S. Cl.

CPC ............ *C07D 405/14* (2013.01); *A61K 31/41* (2013.01); *A61K 31/4155* (2013.01); *A61P 43/00* (2018.01); *C07D 405/06* (2013.01); *C07D 409/06* (2013.01); *C12N 5/10* (2013.01); *C12N 9/22* (2013.01); *C12N 9/78* (2013.01); *C12N 15/111* (2013.01); *C12N 15/87* (2013.01); *C12N 15/90* (2013.01); *C12N 2310/20* (2017.05)

(58) Field of Classification Search

CPC .. C07D 405/14; C07D 405/06; C07D 409/06; A61K 31/41; A61K 31/4155; A61P 43/00; C12N 9/22; C12N 15/111; C12N 15/90

USPC ......... 435/455, 463, 476, 478, 199; 536/6.1, 536/6.2, 17.2, 18.4, 18.1, 23.1, 23.2, 23.7

See application file for complete search history.

(56) References Cited

U.S. PATENT DOCUMENTS

| | | | |
|---|---|---|---|
| 8,513,266 | B2 | 8/2013 | Lamb |
| 8,697,359 | B1 | 4/2014 | Zhang |
| 8,859,532 | B2 | 10/2014 | Turchi |
| 8,980,955 | B2 | 3/2015 | Turchi |
| 10,774,063 | B2 | 9/2020 | Turchi |
| 2007/0196395 | A1 | 8/2007 | Mackerell et al. |
| 2010/0216853 | A1 | 8/2010 | Marmorstein et al. |
| 2010/0249165 | A1 | 9/2010 | Gether et al. |
| 2013/0142887 | A1 | 6/2013 | Alani et al. |
| 2014/0242702 | A1 | 8/2014 | Chen |
| 2015/0024500 | A1 | 1/2015 | Yu et al. |
| 2015/0031134 | A1 | 1/2015 | Zhang et al. |
| 2015/0044772 | A1 | 2/2015 | Zhao |
| 2015/0064790 | A1 | 3/2015 | Gupta et al. |
| 2015/0071906 | A1 | 3/2015 | Liu et al. |
| 2015/0093802 | A1 | 4/2015 | Mccray et al. |
| 2015/0274674 | A1 | 10/2015 | Almstead |
| 2020/0222367 | A1 | 7/2020 | Turchi et al. |
| 2023/0056729 | A1 | 2/2023 | Turchi |

FOREIGN PATENT DOCUMENTS

| | | | |
|---|---|---|---|
| EP | 1905762 | | 4/2008 |
| WO | 2006129583 | | 12/2006 |
| WO | 2007120842 | | 10/2007 |
| WO | 2008045663 | A2 | 4/2008 |
| WO | 2009145829 | | 12/2009 |
| WO | 2015028929 | A1 | 3/2015 |

OTHER PUBLICATIONS

Dorjsuren et al. 2012, PLOS One, 7(10), e47974, 1-12. (Year: 2012).*

Doudna & Charpentier 2014, Science, 346(6213), 1077-1086. (Year: 2014).*

(Continued)

*Primary Examiner* — Anne Marie S Wehbe
*Assistant Examiner* — Katie L Pennington
(74) *Attorney, Agent, or Firm* — Barnes & Thornburg LLP

(57) ABSTRACT

The present disclosure relates to certain compounds having binding affinity for Ku, and uses thereof. Specifically, the present disclosure relates to the use of Ku inhibitors as described herein in site-specific genome engineering technologies, including but not limited to CRISPR/Cas9, Zinc finger nuclease (ZFN), Transcription activator-like effector nuclease (TALEN), and meganuclease. The present disclosure also relates to kits useful for site-specific genome engineering that include at least one compound as described herein.

20 Claims, 5 Drawing Sheets

(56) References Cited

OTHER PUBLICATIONS

Ogiwara et al. 2016, Cancer Discovery, 6(4), 430-445, ePub Nov. 24, 2015. (Year: 2015).*
Robert et al. 2015, Genome Medicine, 7(93), 1-11. (Year: 2015).*
Vidigal & Ventura 2015, Nature Communications, 6, 8083, 1-7. (Year: 2015).*
Horizon Discovery, Dharmacon™ Edit-RTM CRISPR Cas9 gene engineering with Lentiviral Cas9 and sgRNA, published Jul. 2015 , retrieved on Dec. 14, 2024 from the Internet: < https://horizondiscovery.com/-/media/Files/Horizon/resources/Technical-manuals/edit-r-lentiviral-sgrna-manual.pdf>. (Year: 2015).*
Moreau et al. 2008, Bioorganic & Medicinal Chemistry Letters, 18(14), 4022-26. (Year: 2008).*
PCT Search Report and Written Opinion prepared for PCT/US2017/034254, completed Aug. 24, 2017.
Anonymous, Pubchem, NCBI National Center for Biotechnology Information. PubChem Compound Database; CID=50885097, https://pubchem.ncbi.nlm.nih.gov/compound/50885097 create date Feb. 22, 2011.
Moreau, F. et al., "Discovery of new Gram-negative antivirulence drugs: Structure and properties of novel *E. coli* WaaC inhibitors," Bioorganic & Medicinal Chemistry Letters, Jul. 2008, 18(14) pp. 4022-4026.
Pawelczak, K.S. et al., "Coordination of DNA-PK Activation and Nuclease Processing of DNA Termini in NHEJ," Antioxidants & Redox Signaling, 2011, 14(12) pp. 2531-2543.
Grundy, G.J.,et al., "One ring to bring them all—The role of Ku in mammalian non-homologous end joining," DNA Repair, 2014, vol. 17, pp. 30-38.
Hammel, M. et al., "Ku and DNA-dependent Protein Kinase Dynamic Conformations and Assembly Regulate DNA Binding and the initial Non-homologous End Joining Complex," The Journal of Biological Chemistry, 2010, 285(2) pp. 1414-1423.
Cox, et al., "Therapeutic Genome Editing: Prospects and Challenges," Nature Medicine, 2015, 21(2) pp. 121-131.
Pauli, G.F. et al, "Importance of Purity Evaluation and the Potential of Quantitative 1H NMR as a Purity Assay," Journal of Medicinal Chemistry, 2014, 57(2) pp. 9220-9231.
Cushman, et al., "Absolute Quantitative 1H NMR Spectroscopy for Compound Purity Determination," Journal of Medicinal Chemistry, 2014, 57(22) pp. 9219.
Gaj, T. et al., "ZFN, TALEN, and CRISPR/Cas-based methods for genome engineering," Trends in Biotechnology, 2013, 31(7) pp. 397-405.
Anciano Granadillo, V.J. et al., "Targeting the OB-folds of replication protein A with small molecules", Journal of Nucleic Acids, 2010, vol. 2010, Article ID 304035, pp. 1-11.
Andrews, "Development of a high-throughput screen for inhibitors of replication protein A and its role in nucleotide excision repair," Mol. Cancer Ther., 2004, 3, 385-391.
Bernhardt et al., Terpene conjugates of diaminedichloridoplatinum (II) complexes: antiproliferative effects in HL-60 leukemia, 518A2 melanoma, and HT-29 colon cancer cells. Chemistry & Biodiversity, Aug. 2008, vol. 5, No. 8, p. 1645-1659. abstract, p. 1645, para 1, p. 1647, Scheme 1, p. 1649Table 1.
Bowers et al.: "Virtual Ligand Screening of the p300/CBP HistoneAcetyltransferase: Identification of a Selective Small Molecule Inhibitor", Chemistry & Biology, vol. 17, No. 5, May 1, 2010 (May 1, 2010), pp. 471-482, XP055575681, GB ISSN: 1074-5521, DOI: 10.1016/j.chembiol.2010.03.006.
Buchko et al. Structural features of the minimal DNA binding domain (M98-F219) of human nucleotide excision repair protein XPA; Neucleic Acids Research, 1998, vol. 26, (pp. 2779-2788).
CAS RN: 131645-11-9 (entered Jan. 25, 1991).
Deng, "Structure of the Full-length Human RPA 14/32 Complex Gives Insights into the Mechanism of DNA Binding and Complex Formation," J. Mol. Biol., 2007, 374, 865-876.
Extended European Search Report for application No. EP11740474.9, dated Aug. 5, 2013.
Fadda E. "Role of the XPA protein in the NER pathway: A perspective on the function of structural disorder in macromolecular assembly." Comput Struct Biotechnol J. Dec. 8, 2015;14:78-85. doi: 10.1016/j.csbj.2015.11.007. PMID: 26865925; PMCID: PMC4710682.
Gavande, N. S. et al.: "Design and Structure-Guided Development of Novel Inhibitors of the Xeroderma Pigmentosum Group A (XPA) Protein-DNA Interaction", Journal of Medicinal Chemistry, vol. 60, No. 19, Sep. 21, 2017 (Sep. 21, 2017), pp. 8055-8070, XP055796870, US ISSN: 0022-2623.
Gavande, N.S. et al., Structure-Guided Optimization of Replication Protein A (RPA)-DNA Interaction Inhibitors. ACS Medicinal Chemistry Letters. Jan. 2, 2020, vol. 11, No. 6; pp. 1118-1124; DOI: 10.1021/acsmedchemlett.9b00440.
Hilton, B., et al. "A new structural insight into XPA-DNA interactions" Biosci. Rep. 34(6), 831-40 (2014).
Ikegami, T., et al. "Solution structure of the DNA- and RPA-binding domain of the human repair factor XPA" Nat. Struct. Bio., vol. 5, No. Aug. 8, 1998 (pp. 701-706).
International Preliminary Report on Patentability of the International Searching Authority for PCT/US2011/023838, dated Aug. 2012.
JP2022-535116—Office Action dated Nov. 11, 2024 from Japenese Patent Application No. 2022-535116 (including English translation); 6 pages.
Koch, S.C., et al. "Structural insights into the recognition of cisplatin and AAF-dG lesion by Rad14 (XPA)" Proc. Natl. Acad. Sci. U. S. A. 2015, 112, 8272-8277.
Lehman, J. et al., DNA-Dependent Conformational Changes in the Ku Heterodimer. Biochemistry, (2008), vol. 47, pp. 4359-4368.
Loudon, Organic Chemistry, Fourth Edition, New York: Oxford University Press, 2002, pp. 360-361, 1084-1085. (Book Reference available by request).
Mishra, A.K. et al., "Chemical inhibitor targeting the replication protein A-DNA interaction increases the efficacy of Pt-based chemotherapy in lung and ovarian cancer" , Biochemical Pharmacology, 2015, vol. 93, No. 1, pp. 25-33 ([E-pub.] Nov. 4, 2014).
Neher et al.: "Identification of Novel Small Molecule Inhibitors of the XPA Protein Using in Silico Based Screening", ACS Chemical Biology, vol. 5, No. 10, Oct. 15, 2010 (Oct. 15, 2010), pp. 953-965, XP055159629, ISSN: 1554-8929, DOI: 10.1021 /cb1000444.
Park, H. et al., "A novel class of Hsp90 inhibitors isolated by structure-based virtual screening", Bioorganic & Medicinal Chemistry Letters, 2007, vol. 17, No. 22, pp. 6345-6349.
Patrick SM, Turchi JJ, "Stopped-flow kinetic analysis of replication protein A-binding DNA—Damage recognition and affinity for single-stranded DNA reveal differential contributions of k(on) and k(off) rate constants," J. Biol. Chem., 2001, 276.22630-22637.
Patrick SM, Turchi JJ. "Replication Protein A (RPA) Binding to Duplex Cisplatin-damaged DNA is Mediated through the Generation of Single-stranded DNA," J. Biol. Chem., 1999, 274, 14972-14978.
Patrick, S.M., et al. "Xeroderma Pigmentosum Complementation Group A Protein (XPA) Modulates RPA-DNA Interactions via Enhanced Complex Stability and Inhibition of Strand Separation Activity" J. Biol. Chem. v. 277, No. 18, pp. 16096-16101, May 3, 2002.
Pawelczak et al., A mechanism for DNA-PK activation requiring unique contributions from each strand of a DNA terminus and implications for microhomology-mediated nonhomologous DNA end joining. Nucleic Acids Res., (2008), vol. 36, pp. 4022-4031.
Pawelczak et al., Differential activation of DNA-PK based on DNA strand orientation and sequence bias. Nucleic Acids Res., (2005), vol. 33, pp. 152-161.
PCT International Search Report and Written Opinion completed Dec. 12, 2019 and issued in connection with PCT/US2018/051416.
PCT International Search Report and Written Opinion completed by the ISA/US on Feb. 3, 2021 and issued in connection with PCT/US2020/064191.
PCT International Search Report and Written Opinion for PCT/US2011/023838, May 2011.
PCT International Search Report and Written Opinion issued in connection with PCT/US2015/060675, dated Jun. 29, 2016.

(56) References Cited

OTHER PUBLICATIONS

Pierce et al., "Ku DNA end-binding protein modulates homologous repair of double-strand breaks in mammalian cells." 2001, Genes & Development, 15, pp. 3237-3242.
PubChem CID CID 3153480, 4-(3,5-diphenyl-4,5-dihydro-1H-pyrazol-1-yl)-4-oxobutanoic acid <available at https://pubchem.ncbi.nlm.nih.gov/compound/3153480>.
Pubchem, Oprea1_266901; CID 48272669. Pubchem Entry (online). National Center for Biotechnology Information. Jun. 20, 2015 [retrieved on Feb. 3, 2021]. Retrieved from the Internet: [URL: https,//pubchem.ncbi.nlm.nih.gov/substance/48272669 ]; p. 2.
Raghav, Neera et al., "SAR studies of differently functionalized chalcones based hydrazones and their cyclized derivatives as inhibitors of mammalian cathepsin B and cathepsin H", Bioorganic & Medicinal Chemistry, 2014, vol. 22, pp. 4233-4245 ([E-pub.] May 24, 2014).
Robert F. et al, "Pharmacological inhibition of DNA-PK stimulates Cas9-mediated genome editing", Genome Medicine, (Aug. 27, 2015), vol. 7, No. 1, doi: 10.1186/S13073-015-0215-6, ISSN 1756-994X, pp. 1-11, XP002769169.
Rongxue Peng et al, "Potential pitfalls of CRISPR/Cas9-mediated genome editing", FEBS Journal, GB, (20151127), vol. 283, No. 7, doi:10.1111/febs.13586, ISSN 1742-464X, pp. 1218-1231, XP055377561.
Saijo, M., et al. "Nucleotide Excision Repair by Mutant Xeroderma Pigmentosum Group A (XPA) Proteins with Deficiency in Interaction with RPA" J. Biol. Chern, v. 286, No. 7, pp. 5476-5483, Feb. 18, 2011.
Sears et al. "Complex Cisplatin-Double Strand Break (DSB) Lesions Directly Impair Cellular Non-Homologous End-Joining (NHEJ) Independent of Downstream Damage Response (DDR) Pathways." 2012. J Biol Chem, 287(29), pp. 24263-24272.
Seluanov et al., "Analysis of DNA double-strand break (DSB) repair in mammalian cells." 2010, Journal of Visualized Experiments, 43, pp. 1-6.
Sharp, "In vitro Biological Characterization of a Novel, Synthetic Inhibitors Diaryl Pyrazole Resorcinol Class of Heat Shock Protein 90," Cancer Res., 2007, 67, 2206-2216.
Shuck et al., "Targeted inhibition of replication protein A reveals cytotoxic activity, synergy with chemotherapeutic DNA-damaging agents, and insight into cellular function", Cancer Res., 2010, vol. 70, No. 8, pp. 3189-3198.
Shuck et al., "Abstract #5545: The effect of a small molecule inhibitor of Replication Protein A (TDRL-505) on DNA binding, cellular function and platinum sensitivity." Cancer Research, May 1, 2009, 69, 5545.
Shuck, "Identification of Novel Small Molecule Inhibitors of Proteins Required for Genomic Maintenance and Stability," Doctoral thesis, Indiana University. Jun. 2010, pp. 1-131 <available at https://scholar works .iupui.edu/bitstream/handle/ 1805/223 3/Final%20thesis%2003.pdf?sequence=1 >.
Smith and March, March's Advanced Organic Chemistry: Reactions, Mechanisms, and Structure, Fifth Edition, Wiley-Interscience, 2001, pp. 394-415. (Book Reference available by request).
STN Registry Database entry for CAS RN 1311879-37-4; Entered STN Jul. 7, 2011.
Sugitani, N. et al. "Redefining the DNA-Binding Domain of Human XPA" Journal of the American Chemical Society, 2014, 136, 10830-10833.
Sugitani, N. et al. "XPA: A key scaffold for human nucleotide excision repair." DNA Repair (Amst). Aug. 2016, 44:123-135. doi: 10.1016/j.dnarep.2016.05.018. Epub May 20, 2016. PMID: 27247238; PMCID: PMC4958585.
Supplementary European Search Report for counterpart EP patent application No. 20897908.8 dated Oct. 27, 2023.
Turchi J. et al., "Targeting Nucleotide Excision Repair as a Mechanism to Increase Cisplatain Efficacy," In: Bonetti A, Leone R, Muggia FM, Howell SB, editors. Platinum and Other Heavy Metal Compounds in Cancer Chemotherapy. New York: Humana Press; 2009, 177-187, published Dec. 18, 2008.
Vidal. D. et al., "Structure-based discovery of new small molecule inhibitors of low molecular weight protein tyrosine phosphatase," European Journal of Medicinal Chemistry, 2007, 42, 1102-1108.
Wang, Xu et al., "A novel methodology for synthesis of dihydropyrazole derivatives as potential anticancer agents", Organic & Biomolecular Chemistry, 2014, vol. 12, No. 13, pp. 2028-2032 ([E-pub.] Jan. 22, 2014).
Wold MS, "Replication protein A: a heterotrimeric, single-stranded DNA-binding protein required for eukaryotic DNA metabolism," Annual Review of Biochemistry, 1997, 66, 61-92.
Woods et al. "Recognition of DNA Termini by the C-Termunal Region of the Ku80 and the DNA-Dependent Protein Kinase Catalytic Subunit." 2015, PLoS One, 10(5), e0127321.
Yang, Z. "Specific and Efficient Binding of Xeroderma Pigmentosum Complementation Group A to Double-Strand/Single-Strand DNA Junctions with 3' and/or 5' -ssDNA Branches" Biochemistry 2006, 45, 15921-15930.

* cited by examiner

KU INHIBITORS AND THEIR USE

CROSS-REFERENCE TO RELATED APPLICATIONS

This application is a divisional application of U.S. application Ser. No. 16/303,454 filed on Nov. 20, 2018, which is a national stage entry under 35 USC § 371 of PCT International Application Number PCT/US2017/034254, filed May 24, 2017, which claims the benefit of U.S. Provisional Application Ser. No. 62/340,639, filed May 24, 2016.

STATEMENT OF GOVERNMENT RIGHTS

This invention was made with government support under CA180710 awarded by the National Institutes of Health. The Government has certain rights in the invention.

FIELD

The present disclosure relates to certain compounds having binding affinity for Ku, and uses thereof. Specifically, the present disclosure relates to the use of Ku inhibitors as described herein in site-specific genome engineering technologies, including but not limited to CRISPR/Cas9, Zinc finger nuclease (ZFN), Transcription activator-like effector nuclease (TALEN), and meganuclease. The present disclosure also relates to kits useful for site-specific genome engineering that include at least one compound as described herein.

BACKGROUND

Genome engineering is at the forefront of both a clinical and biotechnology research. The ability to make targeted genetic modifications through genome editing (also referred to herein as genome editing with engineered nucleases (GEEN)) has opened up a wide variety of options for scientists in industry and academia and in both therapeutic and biotechnology disciplines. The significance of the method lies in the ability to make targeted insertions, deletions or replacements of DNA sequences in the genome of an organism using engineered nucleases as the "molecular scissors" that initiate the process. Genome editing has found application in targeted gene mutation, creating chromosome rearrangements, studying gene function with stem cells, transgenic animals, endogenous gene labeling, targeted transgene addition, and the like. Because of the wide range of applications and possible genome modifications made possible with the advent of genome editing technologies, the genome editing market is expected to increase to over $3,500M by 2019.

Despite the promise of genome engineering, several drawbacks and challenges in the method have been identified. For example, the principal behind genome editing is the use of engineered nucleases to create a double-stranded DNA break (DSB) in a genome sequence. Following creation of the DNA DSB, one of two pathways is engaged to remedy the break, non-homologous end joining (NHEJ) or homology directed repair (HDR). NHEJ is the dominant pathway for repair of DNA DSB in mammalian cells. This extremely efficient, relatively simple pathway is active throughout the entire cell cycle, unlike HDR which is typically restricted to S and G2 phase of the cell cycle. In addition, NHEJ also does not require a homologous donor molecule. One problem that arises from NHEJ being the dominant repair mechanism is that NHEJ is error-prone, and often leads to insertions and deletions at the site of the DSB. Another issue with NHEJ is that its low gene targeting efficiency necessitates extensive experimentation to identify a single modified clonal cell. Also, NHEJ activity can result in non-specific insertion of a donor DNA molecule into random DSBs that occur naturally throughout the genome. This is problematic as it can result in even lower gene targeting efficiency.

In the presence of a homologous donor sequence, HDR results in accurate insertion of the donor molecule at the DSB site. However, because NHEJ is the dominant DNA repair pathway, the efficiency of genome editing has been limited. Previous research has shown that inhibiting NHEJ results in an increase in HDR activity (Pierce A J 2001). As a result, a need exists to find new pathways through which the NHEJ DNA repair pathway can be inhibited and/or HDR DNA repair pathway can be activated.

SUMMARY

It has been discovered that certain aryl-pyrazone compounds show activity against Ku and can inhibit the interaction of Ku with a DSB to act to shut down the NHEJ DNA repair pathway. In one aspect, the present disclosure provides for a compound of the formula I

I

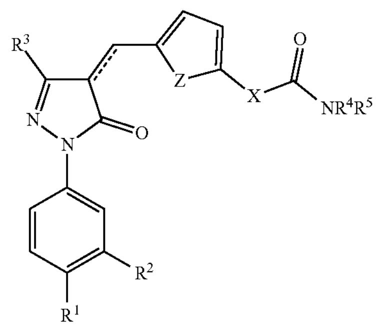

wherein

X is absent, or $C_6$-$C_{10}$ aryl, wherein each hydrogen in $C_6$-$C_{10}$ aryl is optionally substituted with an $R^{10}$, such as

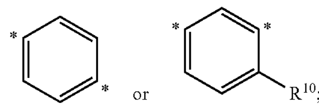

Z is O or S;

$R^1$ and $R^2$ are independently selected from the group consisting of H, halogen, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, 5- to 7-membered heteroaryl, —$OR^6$, —CN, —$NO_2$, —$C(O)R^6$, —$CO_2R^6$, —$C(O)NR^6R^7$, —$OS(O)R^6$, —$OS(O)_2R^6$, —$SR^6$, —$S(O)R^6$, —$S(O)_2R^6$, —$S(O)NR^6R^7$, —$S(O)_2NR^6R^7$, —$OS(O)NR^6R^7$, —$OS(O)_2NR^6R^7$, and —$NR^6R^7$; wherein each hydrogen atom in $C_1$-$C_6$ alkyl, $C_2$-$C_6$ alkenyl, $C_2$-$C_6$ alkynyl or $C_3$-$C_6$ cycloalkyl is independently optionally substituted with halogen;

$R^3$ is H, halogen, or $C_1$-$C_6$ alkyl, wherein each hydrogen atom in $C_1$-$C_6$ alkyl, $C_2$-$C_6$ alkenyl, $C_2$-$C_6$ alkynyl or $C_3$-$C_6$ cycloalkyl is independently optionally substituted with halogen;

$R^4$ and $R^5$ are each independently selected from the group consisting of H, $C_1$-$C_6$ alkyl, $C_2$-$C_6$ alkenyl, $C_2$-$C_6$ alkynyl, $C_3$-$C_6$ cycloalkyl, —$C_1$-$C_6$ alkyl-($C_3$-$C_6$ cycloalkyl), —$C_1$-$C_6$ alkyl-($C_6$-$C_{10}$ aryl), 3- to 7-membered heterocycloalkyl, $C_6$-$C_{10}$ aryl and 5- to 7-membered heteroaryl, wherein each hydrogen atom in $C_1$-$C_6$ alkyl, $C_2$-$C_6$ alkenyl, $C_2$-$C_6$ alkynyl, $C_3$-$C_6$ cycloalkyl, —$C_1$-$C_6$ alkyl-($C_3$-$C_6$ cycloalkyl), —$C_1$-$C_6$ alkyl-($C_6$-$C_{10}$ aryl) or $C_6$-$C_{10}$ aryl is independently optionally substituted with halogen, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, 5- to 7-membered heteroaryl, —$OR^8$, —CN, —$NO_2$, —C(O)$R^8$, —$CO_2R^8$, —C(O)$NR^8R^9$, —OS(O)$R^8$, —$OS(O)_2R^8$, —$SR^8$, —S(O)$R^8$, —$S(O)_2R^8$, —S(O)$NR^8R^9$, —$S(O)_2NR^8R^9$, —OS(O)$NR^8R^9$, —$OS(O)_2NR^8R^9$, or —$NR^8R^9$, provided that one of $R^4$ or $R^5$ is not H;

$R^6$, $R^7$, $R^8$, $R^9$, $R^{11}$ and $R^{12}$ are each independently selected from the group consisting of H, $C_1$-$C_6$ alkyl, $C_2$-$C_6$ alkenyl, $C_2$-$C_6$ alkynyl, $C_3$-$C_6$ cycloalkyl, —$C_1$-$C_6$ alkyl-($C_3$-$C_6$ cycloalkyl), —$C_1$-$C_6$ alkyl-($C_6$-$C_{10}$ aryl), 3- to 7-membered heterocycloalkyl and $C_6$-$C_{10}$ aryl;

$R^{10}$ is selected from the group consisting of halogen, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, 5- to 7-membered heteroaryl, —$OR^{11}$, —CN, —$NO_2$, —C(O)$R^{11}$, —$CO_2R^{11}$, —C(O) $NR^{11}R^{12}$, —OS(O)$R^{11}$, —$OS(O)_2R^{11}$, —$SR^{11}$, —S(O)$R^{11}$, —$S(O)_2R^{11}$, —S(O)$NR^{11}R^{12}$, —$S(O)_2NR^{11}R^{12}$, —OS(O)$NR^{11}R^{12}$, —$OS(O)_2NR^{11}R^{12}$, and —$NR^{11}R^{12}$;

----- is either a single bond or a pi-bond; and represent the points of attachment of X.

In another aspect, the present disclosure provides a kit comprising at least one compound as described herein, and a set of instructions for using the compound in a genome editing method or procedure. In another aspect, the present disclosure provides a kit comprising at least one compound as described herein, and at least one engineered nuclease useful in a genome editing method. In another aspect, the present disclosure provides a kit comprising at least one compound as described herein, and at least one engineered nuclease useful in a genome editing method, and a set of instructions for using the compound in a genome editing method or procedure. In some embodiments, the present disclosure provides for a kit comprising an engineered, non-naturally occurring CRISPR-Cas system comprising one or more vectors comprising:

a) a first regulatory element operable in a eukaryotic cell operably linked to at least one nucleotide sequence encoding a CRISPR-Cas system guide RNA that hybridizes with a target sequence of a DNA molecule in a eukaqotic cell that contains the DNA molecule, wherein the DNA molecule encodes and the eukaryotic cell expresses at least one gene product, and b) a second regulatory element operable in a eukaryotic cell operably linked to a nucleotide sequence encoding a Type-II Cas9 protein, wherein components (a) and (b) are located on same or different vectors of the system, and at least one compound for the formula II

II

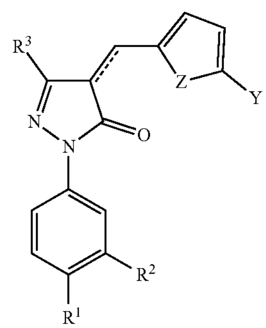

wherein

Y, Z, $R^1$, $R^2$ and $R^3$ are as defined herein.

In another aspect, the present disclosure provides a method of gene editing comprising a. contacting a compound of the formula II

II

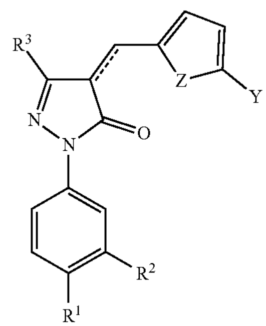

wherein

Z is O or S;

$R^1$ and $R^2$ are independently selected from the group consisting of H, halogen, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, 5- to 7-membered heteroaryl, —$OR^6$, —CN, —$NO_2$, —C(O)$R^6$, —$CO_2R^6$, —C(O)$NR^6R^7$, —OS(O)$R^6$, —$OS(O)_2R^6$, —$SR^6$, —S(O)$R^6$, —$S(O)_2R^6$, —S(O)$NR^6R^7$, —$S(O)_2NR^6R^7$, —OS(O)$NR^6R^7$, —$OS(O)_2NR^6R^7$, and —$NR^6R^7$; wherein each hydrogen atom in $C_1$-$C_6$ alkyl, $C_2$-$C_6$ alkenyl, $C_2$-$C_6$ alkynyl or $C_3$-$C_6$ cycloalkyl is independently optionally substituted with halogen;

$R^3$ is H, halogen, or $C_1$-$C_6$ alkyl, wherein each hydrogen atom in $C_1$-$C_6$ alkyl, $C_2$-$C_6$ alkenyl, $C_2$-$C_6$ alkynyl or $C_3$-$C_6$ cycloalkyl is independently optionally substituted with halogen;

Y is —C(O)$NR^4R^5$ or phenyl, wherein each hydrogen atom in phenyl is optionally substituted with halogen, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, 5- to 7-membered heteroaryl, —$OR^4$, —CN, —$NO_2$, —C(O)$R^4$, —$CO_2R^4$, —C(O)$NR^4R^5$, —OS(O)$R^4$, —$OS(O)_2R^4$, —$SR^4$, —S(O)$R^4$, —$S(O)_2R^4$, —S(O)$NR^4R^5$, —$S(O)_2NR^4R^5$, —OS(O)$NR^4R^5$, —$OS(O)_2$ $NR^4R^5$, and —$NR^4R^5$, or two adjacent hydrogen atoms on phenyl are optionally substituted with a group that combines with the carbon atoms to which they are attached to form a 5- to 7-membered heterocycloalkyl ring;

$R^4$ and $R^5$ are each independently selected from the group consisting of H, $C_1$-$C_6$ alkyl, $C_2$-$C_6$ alkenyl, $C_2$-$C_6$ alkynyl, $C_3$-$C_6$ cycloalkyl, —$C_1$-$C_6$ alkyl-($C_3$-$C_6$ cycloalkyl), —$C_1$-$C_6$ alkyl-($C_6$-$C_{10}$ aryl), 3- to 7-membered heterocycloalkyl, $C_6$-$C_{10}$ aryl and 5- to 7-membered heteroaryl, wherein each hydrogen atom in $C_1$-$C_6$ alkyl, $C_2$-$C_6$ alkenyl, $C_2$-$C_6$ alkynyl, $C_3$-$C_6$ cycloalkyl, —$C_1$-$C_6$ alkyl-($C_3$-$C_6$ cycloalkyl) or —$C_1$-$C_6$ alkyl-($C_6$-$C_{10}$ aryl) is independently optionally substituted with halogen, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, 5- to 7-membered heteroaryl, —$OR^8$, —CN, —$NO_2$, —$C(O)R^8$, —$CO_2R^8$, —$C(O)NR^8R^9$, —$OS(O)R^8$, —$OS(O)_2R^8$, —$SR^8$, —$S(O)R^8$, —$S(O)_2R^8$, —$S(O)NR^8R^9$, —$S(O)_2NR^8R^9$, —$OS(O)NR^8R^9$, —$OS(O)_2NR^8R^9$, or —$NR^8R^9$;

each $R^6$, $R^7$, $R^8$ and $R^9$ is independently selected from the group consisting of H, $C_1$-$C_6$ alkyl, $C_2$-$C_6$ alkenyl, $C_2$-$C_6$ alkynyl, $C_3$-$C_6$ cycloalkyl, alkyl-($C_3$-$C_6$ cycloalkyl), —$C_1$-$C_6$ alkyl-($C_6$-$C_{10}$ aryl), 3- to 7-membered heterocycloalkyl and $C_6$-$C_{10}$ aryl; $C_1$-$C_6$ alkyl, $C_2$-$C_6$ alkenyl, $C_2$-$C_6$ alkynyl, $C_3$-$C_6$ cycloalkyl, alkyl-($C_3$-$C_6$ cycloalkyl) or —$C_1$-$C_6$ alkyl-($C_6$-$C_{10}$ aryl) is independently optionally substituted with halogen, and $\overline{\overline{-----}}$ is either a single bond or a pi-bond, with at least one cell comprising at least one programmable nuclease.

In some embodiments, the present disclosure provides a method of altering expression of at least one gene product comprising (a) introducing into a eukaryotic cell containing and expressing a DNA molecule having a target sequence and encoding the gene product an engineered, non-naturally occurring CRISPR-CRISPR associated (Cas) (CRISPR-Cas) system comprising one or more vectors comprising:

(1) a first regulatory element operable in a eukaryotic cell operably linked to at least one nucleotide sequence encoding a CRISPR-Cas system guide RNA that hybridizes with the target sequence, and (2) a second regulatory element operable in a eukaryotic cell operably linked to a nucleotide sequence encoding a Type-II Cas9 protein, wherein components (1) and (2) are located on same or different vectors of the system, whereby the guide RNA targets the target sequence and the Cas9 protein cleaves the DNA molecule, whereby expression of the at least one gene product is altered; and, wherein the Cas9 protein and the guide RNA do not naturally occur together; and (b) contacting the eukaryotic cell with at least one compound of the formula II

II

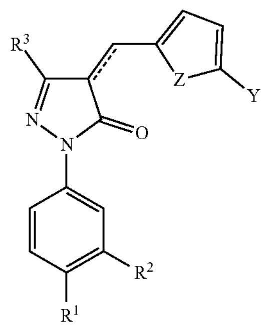

wherein

Y, Z, $R^1$, $R^2$ and $R^3$ are as defined herein.

In another aspect, the present disclosure provide a cell comprising a genome editing systems; and at least one compound of the formula II

II

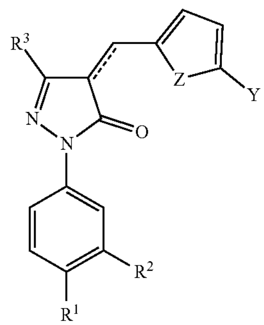

wherein

Y, Z, $R^1$, $R^2$ and $R^3$ are as defined herein. In some embodiments, the genome editing system is selected from the group consisting of CRISPR/Cas9, TALEN, Zn Finger and meganuclease.

Additional embodiments, features, and advantages of the disclosure will be apparent from the following detailed description and through practice of the disclosure. The compounds of the present disclosure can be described as embodiments in any of the following enumerated clauses. It will be understood that any of the embodiments described herein can be used in connection with any other embodiments described herein to the extent that the embodiments do not contradict one another.

1. A compound of the formula I

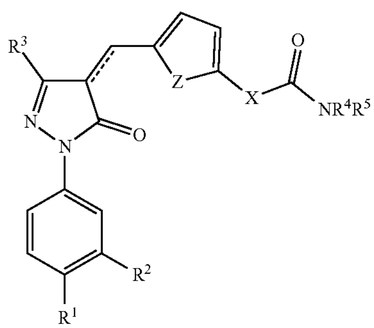

I wherein

X is absent, or $C_6$-$C_{10}$ aryl, wherein each hydrogen in $C_6$-$C_{10}$ aryl is optionally substituted with an $R^{10}$, such as

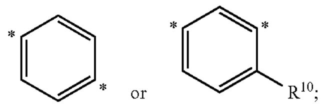

Z is O or S;

$R^1$ and $R^2$ are independently selected from the group consisting of H, halogen, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, 5- to 7-membered heteroaryl, —$OR^6$, —CN, —$NO_2$, —$C(O)R^6$, —$CO_2R^6$, —$C(O)NR^6R^7$, —$OS(O)R^6$, —$OS(O)_2R^6$, —$SR^6$, —$S(O)R^6$, —$S(O)_2R^6$, —$S(O)NR^6R^7$, —$S(O)_2NR^6R^7$, —$OS(O)NR^6R^7$, —$OS(O)_2NR^6R^7$, and —$NR^6R^7$; wherein each hydrogen atom in $C_1$-$C_6$ alkyl, $C_2$-$C_6$ alkenyl, $C_2$-$C_6$ alkynyl or $C_3$-$C_6$ cycloalkyl is independently optionally substituted with halogen;

$R^3$ is H, halogen, or $C_1$-$C_6$ alkyl, wherein each hydrogen atom in $C_1$-$C_6$ alkyl, $C_2$-$C_6$ alkenyl, $C_2$-$C_6$ alkynyl or $C_3$-$C_6$ cycloalkyl is independently optionally substituted with halogen;

$R^4$ and $R^5$ are each independently selected from the group consisting of H, $C_1$-$C_6$ alkyl, $C_2$-$C_6$ alkenyl, $C_2$-$C_6$ alkynyl, $C_3$-$C_6$ cycloalkyl, —$C_1$-$C_6$ alkyl-($C_3$-$C_6$ cycloalkyl), —$C_1$-$C_6$ alkyl-($C_6$-$C_{10}$ aryl), 3- to 7-membered heterocycloalkyl, $C_6$-$C_{10}$ aryl and 5- to 7-membered heteroaryl, wherein each hydrogen atom in $C_1$-$C_6$ alkyl, $C_2$-$C_6$ alkenyl, $C_2$-$C_6$ alkynyl, $C_3$-$C_6$ cycloalkyl, —$C_1$-$C_6$ alkyl-($C_3$-$C_6$ cycloalkyl), —$C_1$-$C_6$ alkyl-($C_6$-$C_{10}$ aryl) or $C_6$-$C_{10}$ aryl is independently optionally substituted with halogen, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, 5- to 7-membered heteroaryl, —$OR^8$, —CN, —$NO_2$, —$C(O)R^8$, —$CO_2R^8$, —$C(O)NR^8R^9$, —$OS(O)R^8$, —$OS(O)_2R^8$, —$S(O)R^8$, —$S(O)_2R^8$, —$S(O)NR^8R^9$, —$S(O)_2NR^8R^9$, —$OS(O)NR^8R^9$, —$OS(O)_2NR^8R^9$, or —$NR^8R^9$, provided that one of $R^4$ or $R^5$ is not H;

$R^6$, $R^7$, $R^8$, $R^9$, $R^{11}$ and $R^{12}$ are each independently selected from the group consisting of H, $C_1$-$C_6$ alkyl, $C_2$-$C_6$ alkenyl, $C_2$-$C_6$ alkynyl, $C_3$-$C_6$ cycloalkyl, —$C_1$-$C_6$ alkyl-($C_3$-$C_6$ cycloalkyl), —$C_1$-$C_6$ alkyl-($C_6$-$C_{10}$ aryl), 3- to 7-membered heterocycloalkyl and $C_6$-$C_{10}$ aryl;

$R^{10}$ is selected from the group consisting of halogen, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, 5- to 7-membered heteroaryl, —$OR^{11}$, —CN, —$NO_2$, —$C(O) R^{11}$, —$CO_2R^{11}$, —$C(O) NR^{11}R^{12}$, —$OS(O) R^{11}$, —$OS(O)_2R^{11}$, —$SR^{11}$, —$S(O)R^{11}$, —$S(O)_2R^{11}$, —$S(O)NR^{11}R^{12}$, —$S(O)_2NR^{11}R^{12}$, —$OS(O)NR^{11}R^{12}$, —$OS(O)_2NR^{11}R^{12}$, and —$NR^{11}R^{12}$;

----- is either a single bond or a pi-bond; and

* represent the points of attachment of X.

2. The compound of clause 1, having the formula Ia,

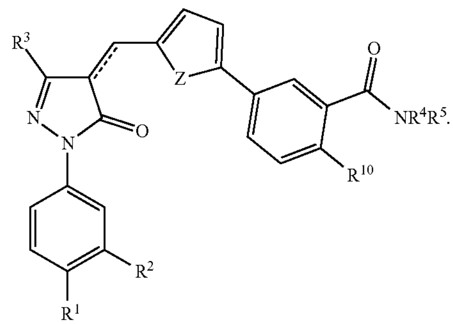

3. The compound of clause 2, wherein $R^{10}$ is chloro.

4. The compound of clause 1, having the formula Ib

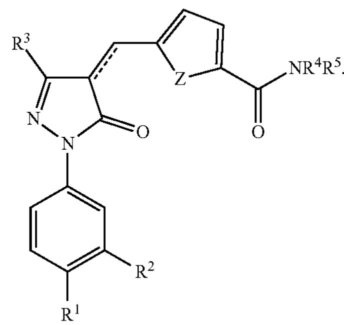

4. The compound of any one of the preceding clauses, wherein Z is O.

5. The compound of any one of clauses 1-3, wherein Z is S.

6. The compound of any one of the preceding clauses, wherein $R^4$ is $C_6$-$C_{10}$ aryl, wherein each hydrogen atom in $C_6$-$C_{10}$ aryl is independently optionally substituted with halogen, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, 5- to 7-membered heteroaryl, —$OR^8$, —CN, —$NO_2$, —$C(O)R^8$, —$CO_2R^8$, —$C(O)NR^8R^9$, —$OS(O)R^8$, —$OS(O)_2R^8$, —$SR^8$, —$S(O)R^8$, —$S(O)_2R^8$, —$S(O)NR^8R^9$, —$S(O)_2NR^8R^9$, —$OS(O)NR^8R^9$, —$OS(O)_2NR^8R^9$, or —$NR^8R^9$.

7. The compound of any one of the preceding clauses, wherein $R^4$ is $C_6$-$C_{10}$ aryl, wherein $C_6$-$C_{10}$ aryl is substituted with at least one halogen or —$OR^8$.

8. The compound of any one of clauses 1 to 6, wherein $R^4$ is phenyl, wherein each hydrogen atom in phenyl is independently optionally substituted with halogen, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, 5- to 7-membered heteroaryl, —$OR^8$, —CN, —$NO_2$, —C(O)R$^8$, —CO$_2$R$^8$, —C(O)NR$^8$R$^9$, —OS(O)R$^8$, —OS(O)$_2$R$^8$, —SR$^8$, —S(O)R$^8$, —S(O)$_2$R$^8$, —S(O)NR$^8$R$^9$, —S(O)$_2$NR$^8$R$^9$, —OS(O)NR$^8$R$^9$, —OS(O)$_2$NR$^8$R$^9$, or —NR$^8$R$^9$.

9. The compound of any one of clauses 1 to 6, wherein R$^4$ is phenyl substituted with at least one halogen or —OR$^8$.

10. The compound of any one of clauses 1 to 5, wherein R$^4$ is —C$_1$-C$_6$ alkyl-(C$_3$-C$_6$ cycloalkyl).

11. The compound of any one of clauses 1 to 5, wherein R$^4$ is —C$_1$-C$_6$ alkyl-(C$_6$-C$_{10}$ aryl), and each hydrogen atom in C$_6$-C$_{10}$ aryl is independently optionally substituted with halogen, C$_1$-C$_6$ alkyl, C$_2$-C$_6$ alkenyl, C$_2$-C$_6$ alkynyl, C$_3$-C$_6$ cycloalkyl, 3- to 7-membered heterocycloalkyl, 5- to 7-membered heteroaryl, —OR$^8$, —CN, —NO$_2$, —C(O)R$^8$, —CO$_2$R$^8$, —C(O)NR$^8$R$^9$, —OS(O)R$^8$, —OS(O)$_2$R$^8$, —SR$^8$, —S(O)R$^8$, —S(O)$_2$R$^8$, —S(O)NR$^8$R$^9$, —S(O)$_2$NR$^8$R$^9$, —OS(O)NR$^8$R$^9$, —OS(O)$_2$NR$^8$R$^9$, or —NR$^8$R$^9$.

12. The compound of any one of clauses 1 to 5, wherein R$^4$ is —C$_1$-C$_6$ alkyl-(C$_6$-C$_{10}$ aryl), wherein C$_6$-C$_{10}$ aryl is substituted with at least one halogen or —OR$^8$.

13. The compound of any one of clauses 1 to 5, wherein R$^4$ is benzyl, wherein each hydrogen atom in benzyl is independently optionally substituted with halogen, C$_1$-C$_6$ alkyl, C$_2$-C$_6$ alkenyl, C$_2$-C$_6$ alkynyl, C$_3$-C$_6$ cycloalkyl, 3- to 7-membered heterocycloalkyl, 5- to 7-membered heteroaryl, —OR$^8$, —CN, —NO$_2$, —C(O)R$^8$, —CO$_2$R$^8$, —C(O)NR$^8$R$^9$, —OS(O)R$^8$, —OS(O)$_2$R$^8$, —SR$^8$, —S(O)R$^8$, —S(O)$_2$R$^8$, —S(O)NR$^8$R$^9$, —S(O)$_2$NR$^8$R$^9$, —OS(O)NR$^8$R$^9$, —OS(O)$_2$NR$^8$R$^9$, or —NR$^8$R$^9$.

14. The compound of any one of clauses 1 to 5, wherein R$^4$ is benzyl substituted with at least one halogen or —OR$^8$.

15. The compound of any one of clauses 1 to 5, wherein R$^4$ selected from the group consisting of

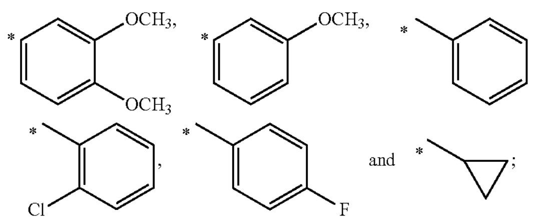

wherein * represent the point of attachment of R$^4$ to the amide nitrogen.

16. The compound of any one of the preceding clauses, wherein R$^5$ is H.

17. The compound of any one of the preceding clauses, wherein R$^3$ is C$_1$-C$_6$ alkyl.

18. The compound of any one of the preceding clauses, wherein R$^3$ is methyl.

19. The compound of any one of the preceding clauses, wherein R$^1$ and R$^2$ are each independently H, 5- to 7-membered heteroaryl, —CN, —CO$_2$R$^6$ or —S(O)$_2$NR$^6$R$^7$, provided that at least one of R$^1$ and R$^2$ is not H.

20. The compound of any one of the preceding clauses, wherein R$^1$ is H and R$^2$ is 5- to 7-membered heteroaryl, —CN or —CO$_2$R$^6$.

21. The compound of any one of clauses 1 to 17, wherein R$^1$ is —CO$_2$R$^6$ or —S(O)$_2$NR$^6$R$^7$, and R$^2$ is H.

22. The compound of clause 20, wherein R$^2$ is —CO$_2$R$^6$, and R$^6$ is H.

23. The compound of clause 20, wherein R$^2$ is —CO$_2$R$^6$, and R$^6$ is ethyl.

24. The compound of clause 21, wherein R$^1$ is —CO$_2$R$^6$, and R$^6$ is H.

25. The compound of clause 21, wherein R$^1$ is —CO$_2$R$^6$, and R$^6$ is ethyl.

26. The compound of clause 21, wherein R$^1$ is —S(O)$_2$NR$^6$R$^7$, and R$^6$ and R$^7$ are H.

27. The compound of clause 20, wherein R$^2$ is 5-tetrazole.

28. The compound of any one of the preceding clauses, wherein ═ ═ ═ is a single bond.

29. The compound of any one of clauses 1 to 27, wherein ═ ═ ═ is a pi-bond.

30. A compound of the formula selected from the group consisting of

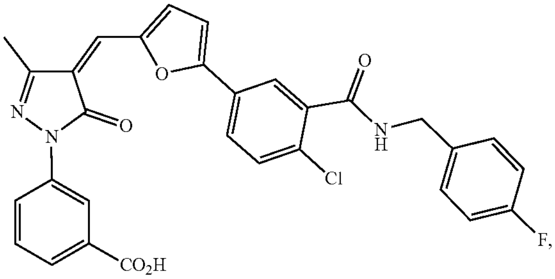

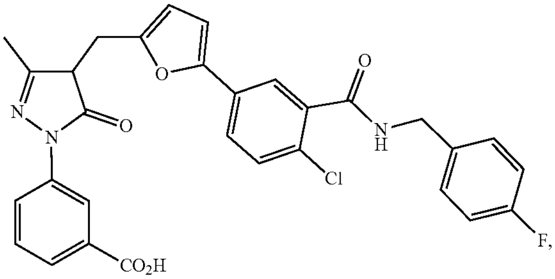

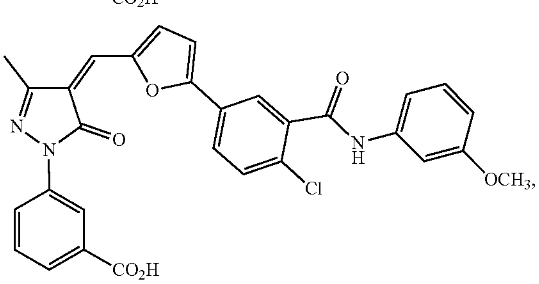

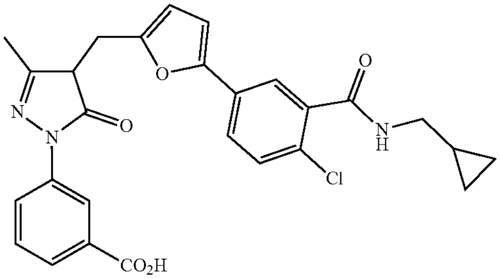

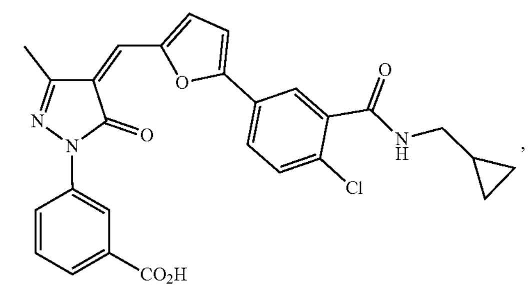
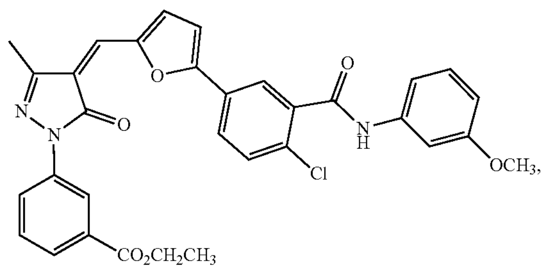
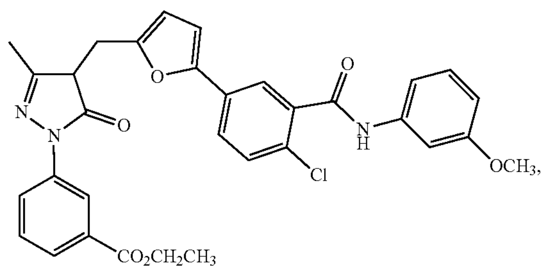
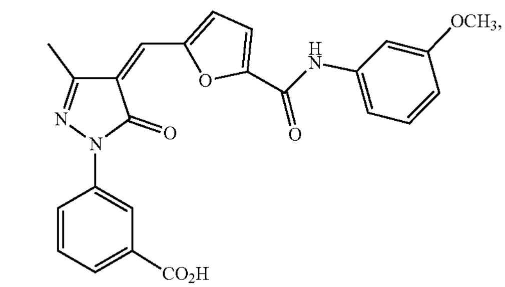
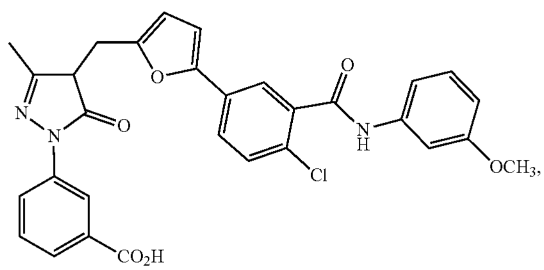
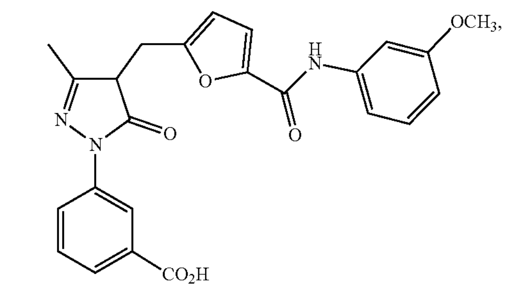
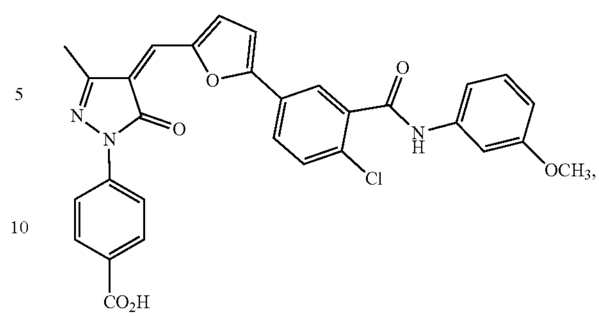
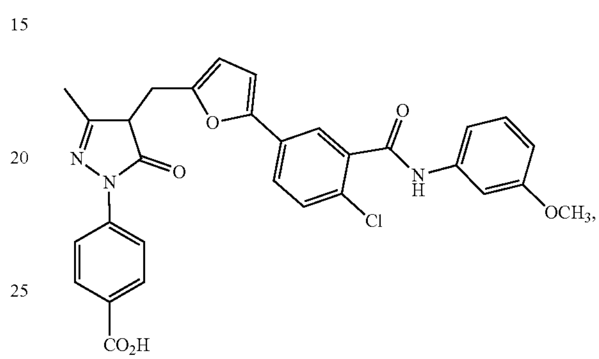
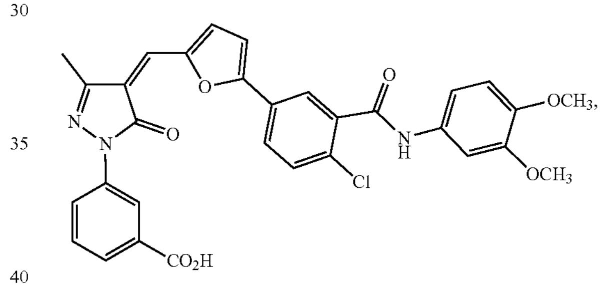
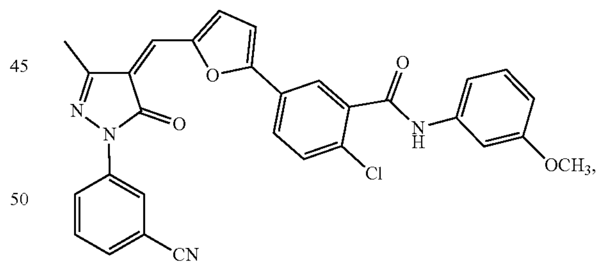
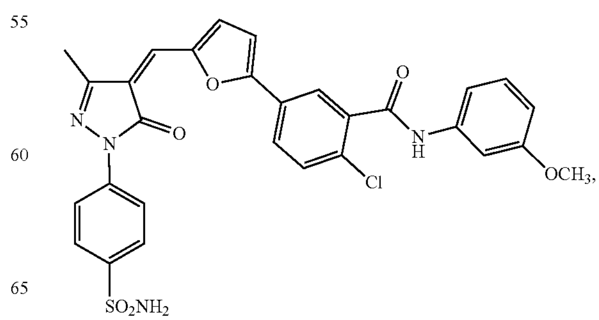

-continued
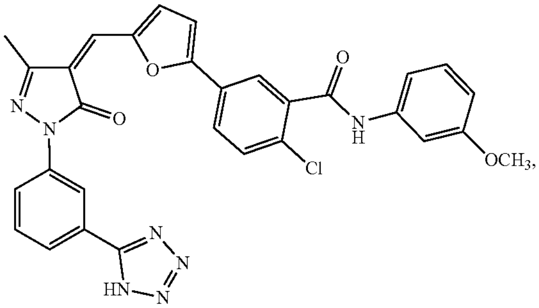,
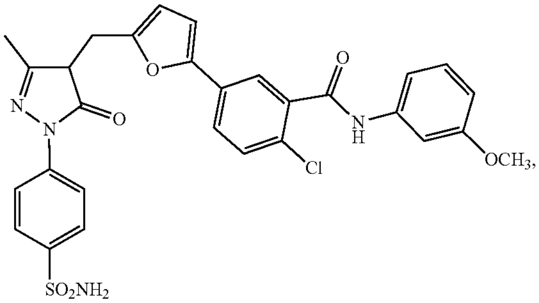,
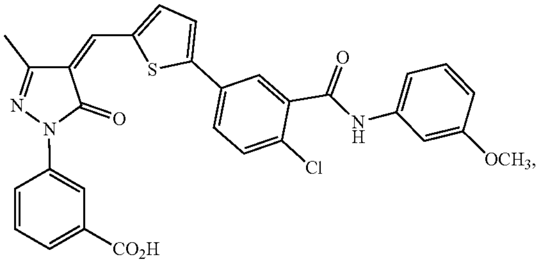,
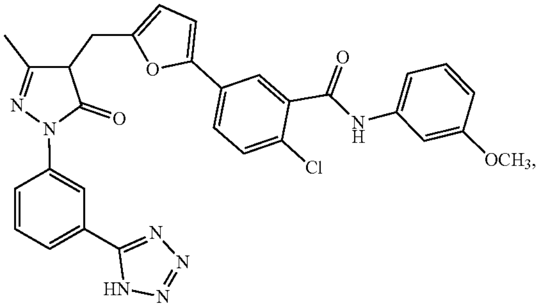,
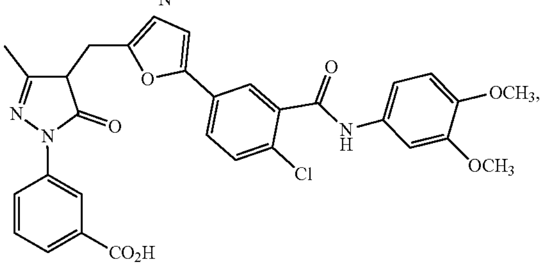,
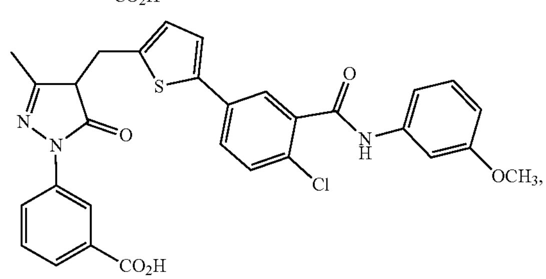,
-continued
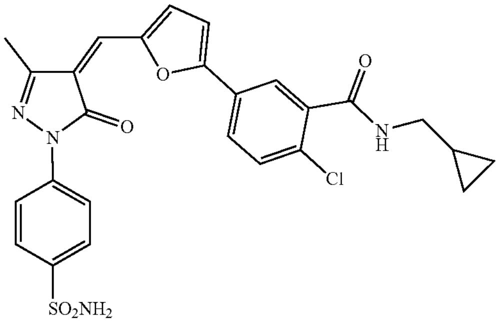,
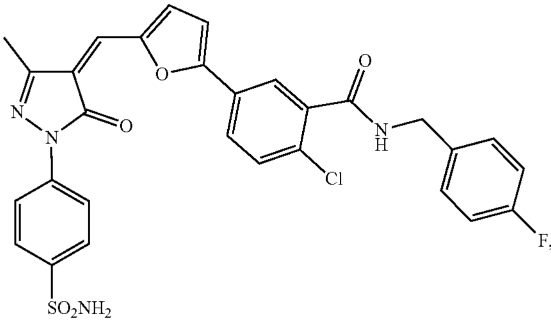,
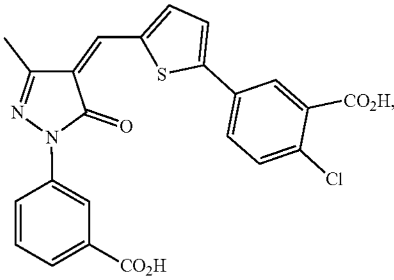,
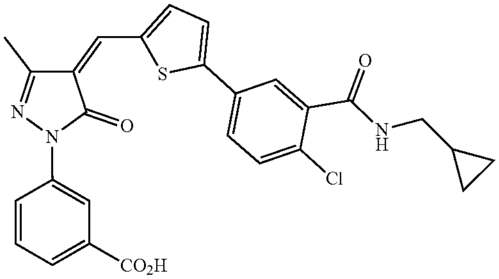,
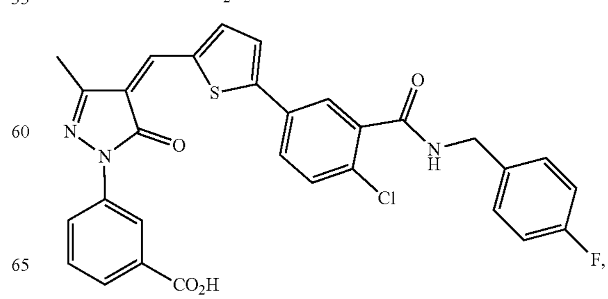, -continued
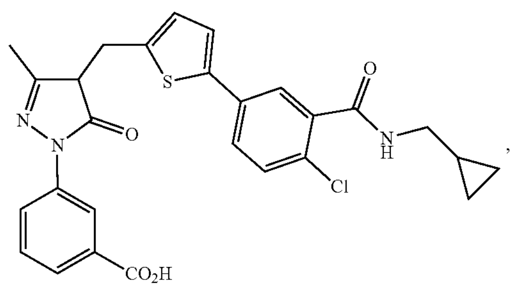
,
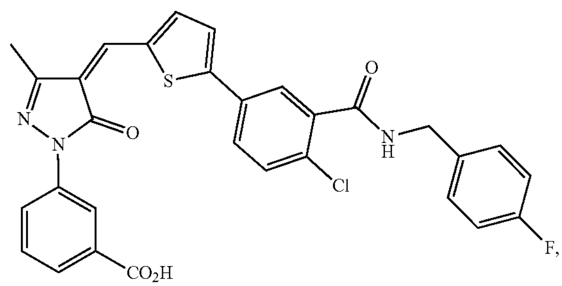
,
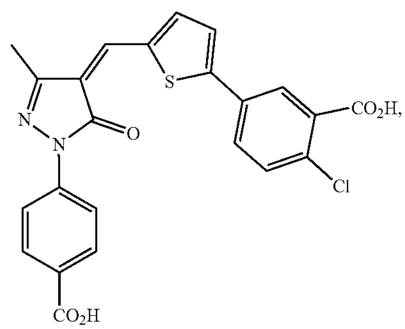
,
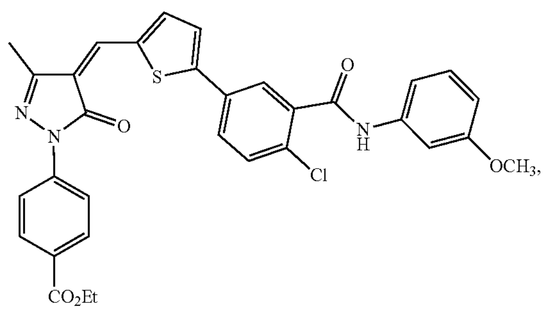
,
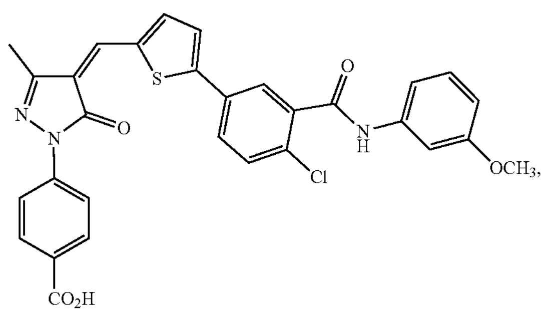
,
-continued
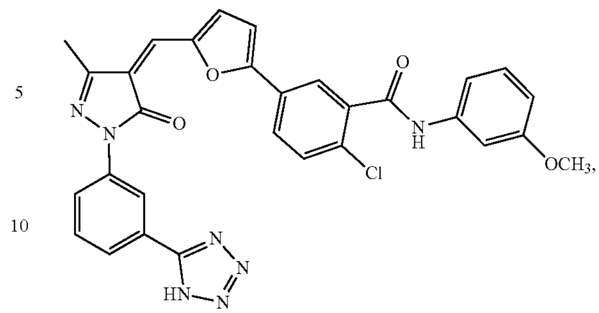
,
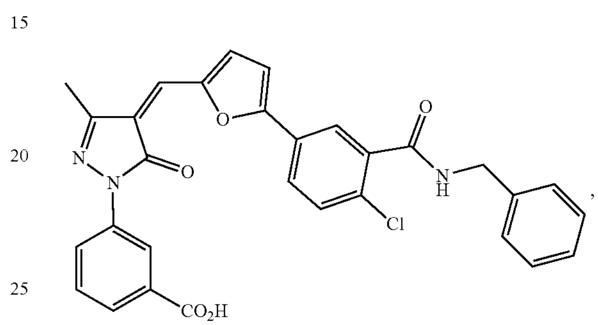
,
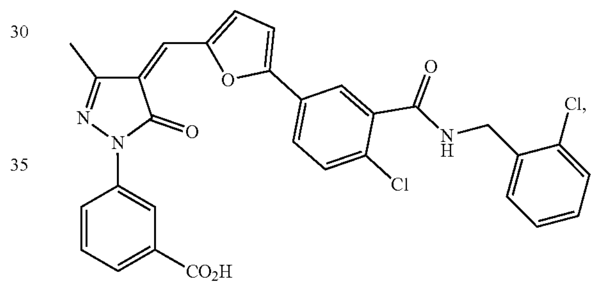
,
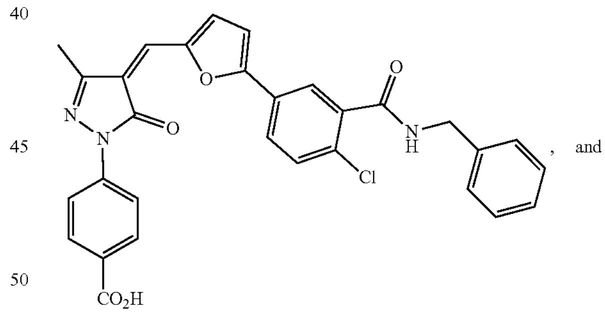
, and
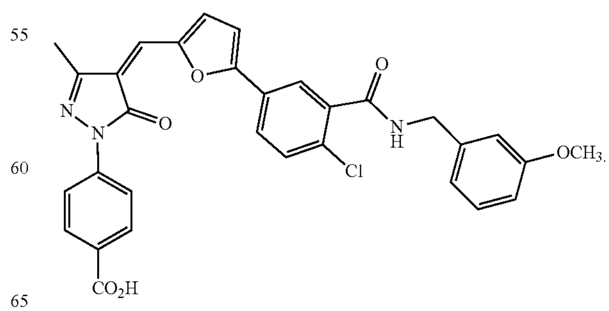
.

27. A method of gene editing comprising a. contacting a compound of the formula II

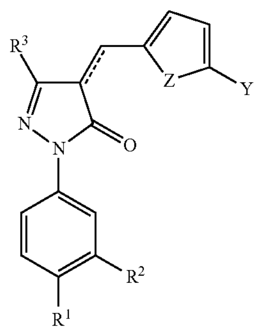

II wherein

Z is O or S;

$R^1$ and $R^2$ are independently selected from the group consisting of H, halogen, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, 5- to 7-membered heteroaryl, —$OR^6$, —CN, —$NO_2$, —$C(O)R^6$, —$CO_2R^6$, —$C(O)NR^6R^7$, —$OS(O)R^6$, —$OS(O)_2R^6$, —$SR^6$, —$S(O)R^6$, —$S(O)_2R^6$, —$S(O)NR^6R^7$, —$S(O)_2NR^6R^7$, —$OS(O)NR^6R^7$, —$OS(O)_2NR^6R^7$, and —$NR^6R^7$; wherein each hydrogen atom in $C_1$-$C_6$ alkyl, $C_2$-$C_6$ alkenyl, $C_2$-$C_6$ alkynyl or $C_3$-$C_6$ cycloalkyl is independently optionally substituted with halogen;

$R^3$ is H, halogen, or $C_1$-$C_6$ alkyl, wherein each hydrogen atom in $C_1$-$C_6$ alkyl, $C_2$-$C_6$ alkenyl, $C_2$-$C_6$ alkynyl or $C_3$-$C_6$ cycloalkyl is independently optionally substituted with halogen;

Y is —$C(O)NR^4R^5$ or phenyl, wherein each hydrogen atom in phenyl is optionally substituted with halogen, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, 5- to 7-membered heteroaryl, —$OR^4$, —CN, —$NO_2$, —$C(O)R^4$, —$CO_2R^4$, —$C(O)NR^4R^5$, —$OS(O)R^4$, —$OS(O)_2R^4$, —$SR^4$, —$S(O)R^4$, —$S(O)_2R^4$, —$S(O)NR^4R^5$, 0173$S(O)_2NR^4R^5$, —$OS(O)NR^4R^5$, —$OS(O)_2NR^4R^5$, and —$NR^4R^5$, or two adjacent hydrogen atoms on phenyl are optionally substituted with a group that combines with the carbon atoms to which they are attached to form a 5- to 7-membered heterocycloalkyl ring;

$R^4$ and $R^5$ are each independently selected from the group consisting of H, $C_1$-$C_6$ alkyl, $C_2$-$C_6$ alkenyl, $C_2$-$C_6$ alkynyl, $C_3$-$C_6$ cycloalkyl, —$C_1$-$C_6$ alkyl-($C_3$-$C_6$ cycloalkyl), —$C_1$-$C_6$ alkyl-($C_6$-$C_{10}$ aryl), 3- to 7-membered heterocycloalkyl, $C_6$-$C_{10}$ aryl and 5- to 7-membered heteroaryl, wherein each hydrogen atom in $C_1$-$C_6$ alkyl, $C_2$-$C_6$ alkenyl, $C_2$-$C_6$ alkynyl, $C_3$-$C_6$ cycloalkyl, —$C_1$-$C_6$ alkyl-($C_3$-$C_6$ cycloalkyl) or —$C_1$-$C_6$ alkyl-($C_6$-$C_{10}$ aryl) is independently optionally substituted with halogen, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, 5- to 7-membered heteroaryl, —$OR^8$, —CN, —$NO_2$, —$C(O)R^8$, —$CO_2R^8$, —$C(O)NR^8R^9$, —$OS(O)R^8$, —$OS(O)_2R^8$, —$SR^8$, —$S(O)R^8$, —$S(O)_2R^8$, —$S(O)NR^8R^9$, —$S(O)_2NR^8R^9$, —$OS(O)NR^8R^9$, —$OS(O)_2NR^8R^9$, or —$NR^8R^9$;

each $R^6$, $R^7$, $R^8$ and $R^9$ is independently selected from the group consisting of H, $C_1$-$C_6$ alkyl, $C_2$-$C_6$ alkenyl, $C_2$-$C_6$ alkynyl, $C_3$-$C_6$ cycloalkyl, —$C_1$-$C_6$ alkyl-($C_3$-$C_6$ cycloalkyl), —$C_1$-$C_6$ alkyl-($C_6$-$C_{10}$ aryl), 3- to 7-membered heterocycloalkyl and $C_6$-$C_{10}$ aryl; $C_1$-$C_6$ alkyl, $C_2$-$C_6$ alkenyl, $C_2$-$C_6$ alkynyl, $C_3$-$C_6$ cycloalkyl, —$C_1$-$C_6$ alkyl-($C_3$-$C_6$ cycloalkyl) or —$C_1$-$C_6$ alkyl-($C_6$-$C_{10}$ aryl) is independently optionally substituted with halogen, and ===== is either a single bond or a pi-bond, with at least one cell comprising at least one programmable nuclease.

BRIEF DESCRIPTION OF THE DRAWINGS

FIG. 4 shows components used in CRISPR Biological Example 5.

FIG. 5 shows schematic and results for CRIPSR Biological Example 5.

DETAILED DESCRIPTION

Figure 1A:
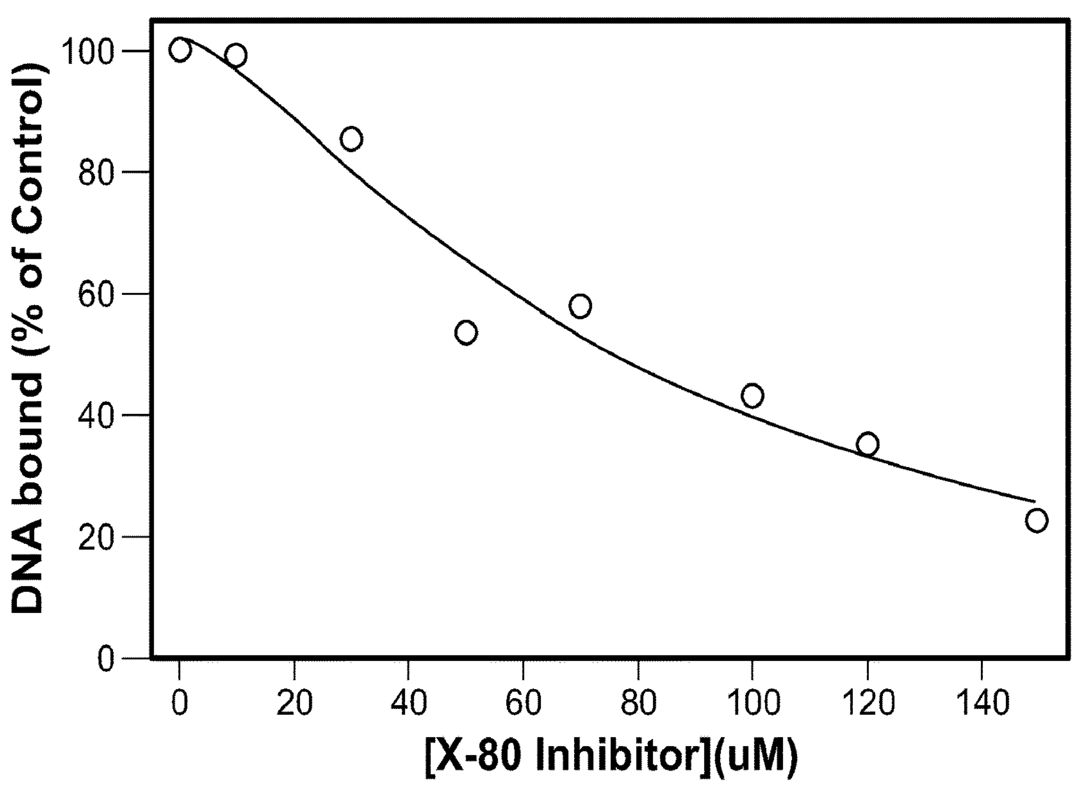
FIG. 1 shows the effect of X-80 on Ku binding DNA with FIG. 1A showing a plot of percentage of DNA bound as a function of X-80 concentration and FIG. 1B showing a DNA gel of Ku-DNA binding as a function of X-80 concentration.

Before the present disclosure is further described, it is to be understood that this disclosure is not limited to particular embodiments described, as such may, of course, vary. It is also to be understood that the terminology used herein is for the purpose of describing particular embodiments only, and is not intended to be limiting, since the scope of the present disclosure will be limited only by the appended claims.

Unless defined otherwise, all technical and scientific terms used herein have the same meaning as is commonly understood by one of ordinary skill in the art to which this disclosure belongs. All patents, applications, published applications and other publications referred to herein are incorporated by reference in their entireties. If a definition set forth in this section is contrary to or otherwise inconsistent with a definition set forth in a patent, application, or other publication that is herein incorporated by reference, the definition set forth in this section prevails over the definition incorporated herein by reference.

As used herein and in the appended claims, the singular forms "a," "an," and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As used herein, the terms "including," "containing," and "comprising" are used in their open, non-limiting sense.

To provide a more concise description, some of the quantitative expressions given herein are not qualified with the term "about". It is understood that, whether the term "about" is used explicitly or not, every quantity given herein is meant to refer to the actual given value, and it is also meant to refer to the approximation to such given value that would reasonably be inferred based on the ordinary skill in the art, including equivalents and approximations due to the experimental and/or measurement conditions for such given value. Whenever a yield is given as a percentage, such yield refers to a mass of the entity for which the yield is given with respect to the maximum amount of the same entity that could be obtained under the particular stoichiometric conditions. Concentrations that are given as percentages refer to mass ratios, unless indicated differently.

Except as otherwise noted, the methods and techniques of the present embodiments are generally performed according to conventional methods well known in the art and as described in various general and more specific references that are cited and discussed throughout the present specification. See, e.g., Loudon, Organic Chemistry, Fourth Edition, New York: Oxford University Press, 2002, pp. 360-361, 1084-1085; Smith and March, March's Advanced Organic Chemistry: Reactions, Mechanisms, and Structure, Fifth Edition, Wiley-Interscience, 2001.

Chemical nomenclature for compounds described herein has generally been derived using the commercially-available ACD/Name 2014 (ACD/Labs) or ChemBioDraw Ultra 13.0 (Perkin Elmer).

It is appreciated that certain features of the disclosure, which are, for clarity, described in the context of separate embodiments, may also be provided in combination in a single embodiment. Conversely, various features of the disclosure, which are, for brevity, described in the context of a single embodiment, may also be provided separately or in any suitable subcombination. All combinations of the embodiments pertaining to the chemical groups represented by the variables are specifically embraced by the present disclosure and are disclosed herein just as if each and every combination was individually and explicitly disclosed, to the extent that such combinations embrace compounds that are stable compounds (i.e., compounds that can be isolated, characterized, and tested for biological activity). In addition, all subcombinations of the chemical groups listed in the embodiments describing such variables are also specifically embraced by the present disclosure and are disclosed herein just as if each and every such sub-combination of chemical groups was individually and explicitly disclosed herein.

Definitions

As used herein, the term "alkyl" includes a chain of carbon atoms, which is optionally branched and contains from 1 to 20 carbon atoms. It is to be further understood that in certain embodiments, alkyl may be advantageously of limited length, including $C_1$-$C_{12}$, $C_1$-$C_{10}$, $C_1$-$C_9$, $C_1$-$C_8$, $C_1$-$C_7$, $C_1$-$C_6$, and $C_1$-$C_4$, Illustratively, such particularly limited length alkyl groups, including $C_1$-$C_8$, $C_1$-$C_7$, $C_1$-$C_6$, and $C_1$-$C_4$, and the like may be referred to as "lower alkyl." Illustrative alkyl groups include, but are not limited to, methyl, ethyl, n-propyl, isopropyl, n-butyl, isobutyl, sec-butyl, tert-butyl, pentyl, 2-pentyl, 3-pentyl, neopentyl, hexyl, heptyl, octyl, and the like. Alkyl may be substituted or unsubstituted. Typical substituent groups include cycloalkyl, aryl, heteroaryl, heteroalicyclic, hydroxy, alkoxy, aryloxy, mercapto, alkylthio, arylthio, cyano, halo, carbonyl, oxo, (=O), thiocarbonyl, O-carbamyl, N-carbamyl, O-thiocarbamyl, N-thiocarbamyl, C-amido, N-amido, C-carboxy, O-carboxy, nitro, and amino, or as described in the various embodiments provided herein. It will be understood that "alkyl" may be combined with other groups, such as those provided above, to form a functionalized alkyl. By way of example, the combination of an "alkyl" group, as described herein, with a "carboxy" group may be referred to as a "carboxyalkyl" group. Other non-limiting examples include hydroxyalkyl, aminoalkyl, and the like.

As used herein, the term "alkenyl" includes a chain of carbon atoms, which is optionally branched, and contains from 2 to 20 carbon atoms, and also includes at least one carbon-carbon double bond (i.e. C=C). It will be understood that in certain embodiments, alkenyl may be advantageously of limited length, including $C_2$-$C_{12}$, $C_2$-$C_9$, $C_2$-$C_8$, $C_2$-$C_7$, $C_2$-$C_6$, and $C_2$-$C_4$. Illustratively, such particularly limited length alkenyl groups, including $C_2$-$C_8$, $C_2$-$C_7$, $C_2$-$C_6$, and $C_2$-$C_4$ may be referred to as lower alkenyl. Alkenyl may be unsubstituted, or substituted as described for alkyl or as described in the various embodiments provided herein. Illustrative alkenyl groups include, but are not limited to, ethenyl, 1-propenyl, 2-propenyl, 1-, 2-, or 3-butenyl, and the like.

As used herein, the term "alkynyl" includes a chain of carbon atoms, which is optionally branched, and contains from 2 to 20 carbon atoms, and also includes at least one carbon-carbon triple bond (i.e. C≡C). It will be understood that in certain embodiments, alkynyl may each be advantageously of limited length, including $C_2$-$C_{12}$, $C_2$-$C_9$, $C_2$-$C_8$, $C_2$-$C_7$, $C_2$-$C_6$, and $C_2$-$C_4$. Illustratively, such particularly limited length alkynyl groups, including $C_2$-$C_8$, $C_2$-$C_7$, $C_2$-$C_6$, and $C_2$-$C_4$ may be referred to as lower alkynyl. Alkenyl may be unsubstituted, or substituted as described for alkyl or as described in the various embodiments provided herein. Illustrative alkenyl groups include, but are not limited to, ethynyl, 1-propynyl, 2-propynyl, 1-, 2-, or 3-butynyl, and the like.

As used herein, the term "aryl" refers to an all-carbon monocyclic or fused-ring polycyclic groups of 6 to 12 carbon atoms having a completely conjugated pi-electron system. It will be understood that in certain embodiments, aryl may be advantageously of limited size such as $C_6$-$C_{10}$ aryl. Illustrative aryl groups include, but are not limited to, phenyl, naphthalenyl and anthracenyl. The aryl group may be unsubstituted, or substituted as described for alkyl or as described in the various embodiments provided herein.

As used herein, the term "cycloalkyl" refers to a 3 to 15 member all-carbon monocyclic ring, including an all-carbon 5-member/6-member or 6-member/6-member fused bicyclic ring, or a multicyclic fused ring (a "fused" ring system means that each ring in the system shares an adjacent pair of carbon atoms with each other ring in the system) group, where one or more of the rings may contain one or more double bonds but the cycloalkyl does not contain a completely conjugated pi-electron system. It will be understood that in certain embodiments, cycloalkyl may be advantageously of limited size such as $C_3$-$C_{13}$, $C_3$-$C_9$, $C_3$-$C_6$ and $C_4$-$C_6$. Cycloalkyl may be unsubstituted, or substituted as described for alkyl or as described in the various embodiments provided herein. Illustrative cycloalkyl groups include, but are not limited to, cyclopropyl, cyclobutyl, cyclopentyl, cyclopentenyl, cyclopentadienyl, cyclohexyl, cyclohexenyl, cycloheptyl, adamantyl, norbornyl, norbornenyl, 9H-fluoren-9-yl, and the like. Illustrative examples of cycloalkyl groups shown in graphical representations include the following entities, in the form of properly bonded moieties:

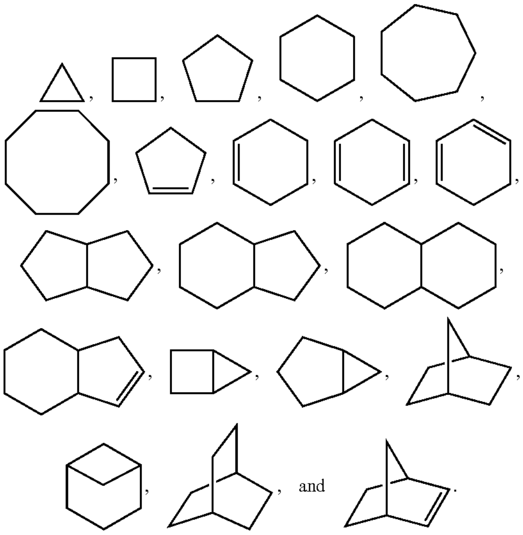

As used herein, the term “heterocycloalkyl” refers to a monocyclic or fused ring group having in the ring(s) from 3 to 12 ring atoms, in which at least one ring atom is a heteroatom, such as nitrogen, oxygen or sulfur, the remaining ring atoms being carbon atoms. Heterocycloalkyl may optionally contain 1, 2, 3 or 4 heteroatoms. Heterocycloalkyl may also have one of more double bonds, including double bonds to nitrogen (e.g. C═N or N═N) but does not contain a completely conjugated pi-electron system. It will be understood that in certain embodiments, heterocycloalkyl may be advantageously of limited size such as 3- to 7-membered heterocycloalkyl, 5- to 7-membered heterocycloalkyl, and the like. Heterocycloalkyl may be unsubstituted, or substituted as described for alkyl or as described in the various embodiments provided herein. Illustrative heterocycloalkyl groups include, but are not limited to, oxiranyl, thianaryl, azetidinyl, oxetanyl, tetrahydrofuranyl, pyrrolidinyl, tetrahydropyranyl, piperidinyl, 1,4-dioxanyl, morpholinyl, 1,4-dithianyl, piperazinyl, oxepanyl, 3,4-dihydro-2H-pyranyl, 5,6-dihydro-2H-pyranyl, 2H-pyranyl, 1, 2, 3, 4-tetrahydropyridinyl, and the like. Illustrative examples of heterocycloalkyl groups shown in graphical representations include the following entities, in the form of properly bonded moieties:

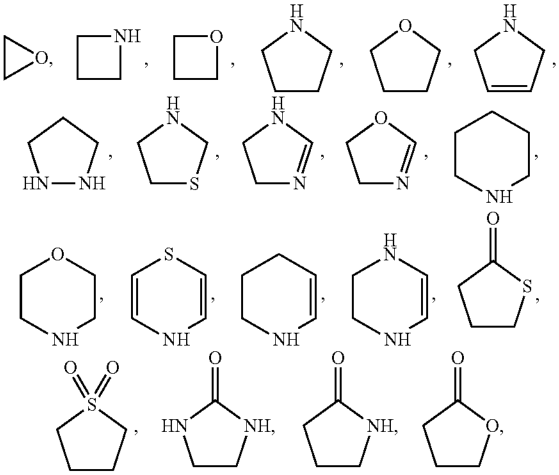

-continued

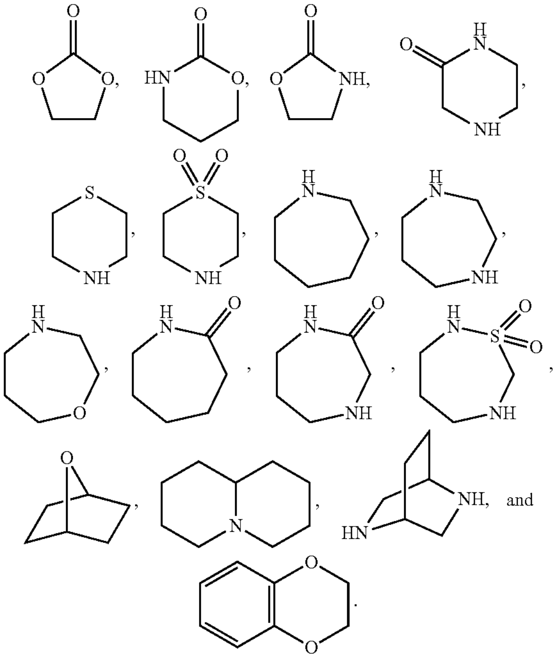

As used herein, the term “heteroaryl” refers to a monocyclic or fused ring group of 5 to 12 ring atoms containing one, two, three or four ring heteroatoms selected from nitrogen, oxygen and sulfur, the remaining ring atoms being carbon atoms, and also having a completely conjugated pi-electron system. It will be understood that in certain embodiments, heteroaryl may be advantageously of limited size such as 3- to 7-membered heteroaryl, 5- to 7-membered heteroaryl, and the like. Heteroaryl may be unsubstituted, or substituted as described for alkyl or as described in the various embodiments provided herein. Illustrative heteroaryl groups include, but are not limited to, pyrrolyl, furanyl, thiophenyl, imidazolyl, oxazolyl, thiazolyl, pyrazolyl, pyridinyl, pyrimidinyl, quinolinyl, isoquinolinyl, purinyl, tetrazolyl, triazinyl, pyrazinyl, tetrazinyl, quinazolinyl, quinoxalinyl, thienyl, isoxazolyl, isothiazolyl, oxadiazolyl, thiadiazolyl, triazolyl, benzimidazolyl, benzoxazolyl, benzthiazolyl, benzisoxazolyl, benzisothiazolyl and carbazoloyl, and the like. Illustrative examples of heteroaryl groups shown in graphical representations, include the following entities, in the form of properly bonded moieties:

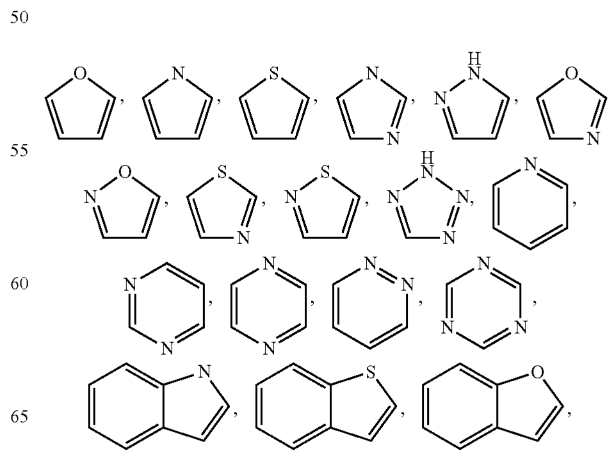

-continued

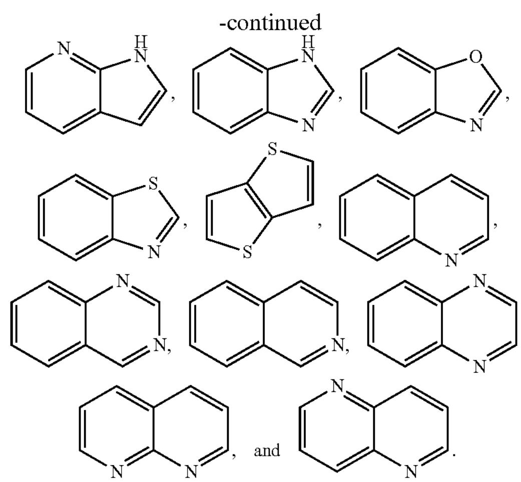

, and .

As used herein, "hydroxy" or "hydroxyl" refers to an —OH group.

As used herein, "alkoxy" refers to both an —O-(alkyl) or an —O-(unsubstituted cycloalkyl) group. Representative examples include, but are not limited to, methoxy, ethoxy, propoxy, butoxy, cyclopropyloxy, cyclobutyloxy, cyclopentyloxy, cyclohexyloxy, and the like.

As used herein, "aryloxy" refers to an —O-aryl or an —O-heteroaryl group. Representative examples include, but are not limited to, phenoxy, pyridinyloxy, furanyloxy, thienyloxy, pyrimidinyloxy, pyrazinyloxy, and the like, and the like.

As used herein, "mercapto" refers to an —SH group.

As used herein, "alkylthio" refers to an —S-(alkyl) or an —S-(unsubstituted cycloalkyl) group. Representative examples include, but are not limited to, methylthio, ethylthio, propylthio, butylthio, cyclopropylthio, cyclobutylthio, cyclopentylthio, cyclohexylthio, and the like.

As used herein, "arylthio" refers to an —S-aryl or an —S-heteroaryl group. Representative examples include, but are not limited to, phenylthio, pyridinylthio, furanylthio, thienylthio, pyrimidinylthio, and the like.

As used herein, "halo" or "halogen" refers to fluorine, chlorine, bromine or iodine.

As used herein, "cyano" refers to a —CN group.

The term "oxo" represents a carbonyl oxygen. For example, a cyclopentyl substituted with oxo is cyclopentanone.

As used herein, "bond" refers to a covalent bond.

The term "substituted" means that the specified group or moiety bears one or more substituents. The term "unsubstituted" means that the specified group bears no substituents. Where the term "substituted" is used to describe a structural system, the substitution is meant to occur at any valency-allowed position on the system. In some embodiments, "substituted" means that the specified group or moiety bears one, two, or three substituents. In other embodiments, "substituted" means that the specified group or moiety bears one or two substituents. In still other embodiments, "substituted" means the specified group or moiety bears one substituent.

As used herein, "optional" or "optionally" means that the subsequently described event or circumstance may but need not occur, and that the description includes instances where the event or circumstance occurs and instances in which it does not. For example, "wherein each hydrogen atom in $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, or mono- or bicyclic heteroaryl is independently optionally substituted by $C_1$-$C_6$ alkyl" means that an alkyl may be but need not be present on any of the $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, or mono- or bicyclic heteroaryl by replacement of a hydrogen atom for each alkyl group, and the description includes situations where the $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, or mono- or bicyclic heteroaryl is substituted with an alkyl group and situations where the $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, or mono- or bicyclic heteroaryl is not substituted with the alkyl group.

As used herein, "independently" means that the subsequently described event or circumstance is to be read on its own relative to other similar events or circumstances. For example, in a circumstance where several equivalent hydrogen groups are optionally substituted by another group described in the circumstance, the use of "independently optionally" means that each instance of a hydrogen atom on the group may be substituted by another group, where the groups replacing each of the hydrogen atoms may be the same or different. Or for example, where multiple groups exist all of which can be selected from a set of possibilities, the use of "independently" means that each of the groups can be selected from the set of possibilities separate from any other group, and the groups selected in the circumstance may be the same or different.

Any formula depicted herein is intended to represent a compound of that structural formula as well as certain variations or forms. For example, a formula given herein is intended to include a racemic form, or one or more enantiomeric, diastereomeric, or geometric isomers, or a mixture thereof. Additionally, any formula given herein is intended to refer also to a hydrate, solvate, or polymorph of such a compound, or a mixture thereof.

Representative Embodiments

It will be appreciated that certain advantages can be gained from applying any of the compounds described herein to genome editing methodologies or technologies. For example, inhibiting the NHEJ pathway to increase the efficiency of the HDR DNA repair pathway will increase the efficiency of genome editing methodologies or technologies. One advantage of targeting Ku lies in the early role Ku plays in the NHEJ DNA repair pathway. Without being bound by theory, Ku is believed to be responsible for initiation of the NHEJ pathway by binding to the termini of broken DNA (Pawelczak K S, et al., Antioxid Redox Signal Vol 14; No. 12; pp. 2531-43 (2011)). Thus, inhibiting the initial molecular event in the NHEJ pathway, Ku interactions with DNA ends, Ku inhibition proves to efficiently block NHEJ catalyzed repair, and drive the processing enzymes to allow HDR mediated recombination with the appropriate donor DNA molecule. On the contrary, prior technologies have inhibited the final step, ligation of the DNA strands through, for example, DNA Ligase IV (Grundy, G J., 2014, Hammel, M., 2010). Such downstream interference with the NHEJ repair pathway may provide incomplete NHEJ processing of the DSB, but it also renders the break unable to be repaired by HDR as well, resulting in cell death. An advantage of targeting Ku is that the DSB will remain unprocessed and eligible for HDR engagement, and thus represents a true increase in the number of cells that are capable of HDR activity. Furthermore, inhibiting NHEJ can decrease non-specific gene editing, which is significant in some settings, such as, researchers using the technology to generate genetically modified products or for use in clinical applications subject to regulatory review. Additionally, decreasing non-specific gene editing products will allow for easier screening to identify rare targeting events, as researchers will not have to screen large population of recombinants to eliminate the non-specific gene editing events.

Genome editing has found application in numerous areas of clinical medicine and biotechnological research. For example, genome editing for therapeutic use has been the subject of a great deal of research and may prove to be a promising therapy in many diverse diseases including, but not limited to, hemophilia B, HIV, Duchenne muscular dystrophy (DMD), Hepatitis B (Hep B), SCID, cataracts, cystic fibrosis, hereditary tyrosinemia and cancer. See for example, Turitz-Cox, D. B. et al., Nature Medicine, Vol. 21, No. 2, pp. 121-131 (2015). IN addition, genome editing has been applied to the biotechnological and genetic research as a tool to understand the function of genes and for the manipulation of genes. Genome editing has been used for gene disruption, gene addition and gene correction in cells from numerous organisms including but not limited to human, zebrafish, bovine, rat, *Arabidopsis, C. elegans*, hamster, *Drosophila*, rice, mouse, maize, tobacco, and the like. In addition, a wide range of genes have been manipulated by gene editing technology including, but not limited to, CCRS, TCR, go1, nt1, kra, GGTA1, LDLR, ACAN12, p65, EMX1, PVALB, IgM, Rab38, ADH1, TT4, ben-1, rex-1, sdc-1, DHFR, yellow, OsSWEET14, OCT4, PITX3, F9 (coagulation Factor IX), Rosa26, AAVS1, VEGF-A, tyrosine hydroxylase, fam46c, smad5, IPK1, IL2RG, A1AT, HBB, SNCA, SuRA, SurRB, and the like. See for example, Gaj, T. et al., Trends in Biotechnology, v. 31, No. 7, pp. 397-405 (2013). In addition, genome editing technologies have been applied in agricultural research. See for example Petolino, J F., 2015.

It will be appreciated that the compounds described herein can be applied to any genome editing methodology or technology known to one of skill in the art, and that the identity of the genome editing methodology or technology is not particularly limited in anyway. It will be appreciated that the various genome editing technologies known in the art are typically classified according to the type of engineered nuclease being applied in the technology. Exemplary genome editing technologies useful in connection with the compounds described herein include, but are not limited to, CRISPR/Cas9, TALEN, Zn Finger, and meganuclease.

CRISPR

Clustered Regularly Interspaced Short Palindromic repeat (CRISPR)-associated nuclease Cas9 introduces DNA double-stand breaks (DSBs) at targeted sequences. The CRISPR-Cas9 system comprises a programmable nuclease that targets DNA through an RNA-DNA interaction and by protein-DNA interactions. The CRISPR-Cas9 system comprises a plasmid encoding the Cas9 endonuclease and a plasmid encoding a CRISPR RNA (crRNA) specific for a DNA sequence. The CRISPR-Cas9 system is programmable by selecting a crRNA specific for the DNA target. The CRISPR-Cas9 system is reprogrammable by changing the crRNA in the crRNA plasmid. See for example, U.S. Pat. No. 8,697,359; United States Patent Publication No. US20150031134; United States Patent Publication No. US20150044772; United States Patent Publication No. US20150024500, incorporated herein by reference.

Preparing a CRISPR-Cas9 system comprises identifying a target DNA sequence. Once the target DNA sequence is identified, a guide RNA (gRNA) comprising the crRNA with a trans-activating RNA (tracrRNA) is prepared by PCR. As an example, the prepared gRNA can then be co-transfected with mRNA coding Cas9 into a target cell, in addition to other mechanisms of delivery. An illustrative method for preparing the gRNA is the GeneArt™ Method by ThermoFisher. Another illustrative method for preparing the gRNA is by cloning the target sequence into a pCas Guide vector as provided by Origene. The pCas Guide vector can be co-transfected with donor vector comprising left and right homologous arms into target cells. The CRISPR-Cas9 system can then be transfected or transduced into a target cell. Illustrative target cell lines include the mammalian cell lines HEK 293, CHO, A549, U2OS, HEP-2, MDCKII, Vero76, A375, Hela, HepG2, HACAT, HCT116, HepaRG, Jurkat, WT macrophages, and TF-1, although any suitable bacterial, yeast, mammalian or plant cell is comprehended. The target cell lines also include plant lines. As another example, the requisite proteins and enzymes for CRISPR/Cas9 can be directly introduced into the target cells.

TALEN

Transcription activator-like effector nucleases (TALENs) introduce DNA DSBs at targeted sequences. The TALEN system comprises a programmable nuclease that targets DNA through a protein-DNA interaction. The TALEN system comprises linking together a TALE monomer with a non-specific nuclease. Each TALE monomer comprises a series of TALES that are each specific for a single DNA base pair. The plurality TALEs are linked together to recognize a specific DNA sequence (14-20 bp per monomer) and conjugated to a nuclease to introduce the DSB into the targeted DNA. The TALEN system is programmable by selecting the appropriate combination of TALE domains specific for the DNA target. The TALEN system is reprogrammable by interchanging the TALE domains in the TALE monomer by molecular cloning. See, for example, United States Patent Publication No. US20150071906; incorporated herein by reference.

Preparing the TALEN system comprises identifying a target DNA sequence. The target DNA sequence can be provided to a vendor to produce a TALEN specific for the target DNA sequence. An illustrative method for preparing the TALEN is by providing the target DNA to a vendor, for example ThermoFisher. Illustratively, the vendor will clone the requisite TALEs into a vector comprising a nuclease to produce the TALEN system. The TALEN is then transfected or transduced into the target cell. Target cells include bacterial cells, mammalian cells, yeast cells, and plant cells.

Zn Finger

Zn-finger nucleases (ZFNs) introduce DNA DSBs at targeted sequences. The ZFN system comprises a programmable nuclease that targets DNA through a protein-DNA interaction. The ZFN system comprises linking together a zinc-finger monomer with a non-specific nuclease. Each zinc-finger monomer comprises a plurality of $Cys_2$-$His_2$ zinc-finger domains that each recognize a specific 3-base pair combination of DNA. The plurality of $Cys_2$-$His_2$ zinc-finger domains are linked together to form the Zn-finger monomer that recognizes a specific DNA sequence (9-18 bp per monomer) and conjugated to a nuclease to insert a DSB near the targeted site. The ZFN system is programmable by selecting the appropriate combination of zinc-finger domains specific for the DNA target sequence. The ZFN system is reprogrammable by linking together different $Cys_2$-$His_2$ zinc-finger domains specific for a target DNA sequence. See for example, United States Patent Publication No. US20150093802; United States Patent Publication No. US20150064790; incorporated herein by reference.

Preparing the ZFN system comprises identifying a target DNA sequence. The target DNA sequence can then be provided to a vendor to produce a ZFN specific for the target DNA. An illustrative vendor is Sigma Aldrich which prepares a CompoZr™ kit. Illustratively, upon supplying the target DNA sequence, the vendor will use an algorithm to design ZFN candidates targeting the gene region of interest. The ZFN candidates can then be validated. The validated ZFNs in a plasmid can then be transfected or transduced into a target cell. Target cells include bacterial cells, mammalian cells, yeast cells, and plant cells.

Meganucleases

Meganucleases introduce DNA DSBs at targeted sequences. The meganuclease system comprises a programmable nuclease that targets >14 bp of DNA through a protein-DNA interaction. Retargeting the meganucleases requires changing the domains that recognize the target DNA.

In some embodiments, at least one programmable nuclease is transfected into a target cell, and the cell is contacted with at least one compound of the present disclosure. In some embodiments, at least one programmable nuclease is transfected into a target cell using a transfection reagent. Alternatively, in some embodiments, at least one programmable nuclease is electroporated into a target cell. In some embodiments, at least one programmable nuclease is packaged in at least one AAV vector and transduced into a target cell. In some embodiments, a programmable nuclease may be packaged into a single AAV vector, or alternatively, may be packaged into more than one AAV vector. In some embodiments, the methods described herein include additional steps depending on the type of genome editing technology being used, such as CRISPR/Cas9, TALEN, Zn Finger, or meganuclease. One of skill in the art will readily appreciate that the steps and reagents described in the paragraphs above for each of the representative technologies can be used in connection with the present teachings.

In addition, the present disclosure provides for kits of parts directed to genome editing technologies in connection with the compounds described herein. In one aspect, the present disclosure provides a kit comprising one or more of the components described herein. In some embodiments, the kit comprises a vector system and instructions for using the kit. In some embodiments, the vector system comprises (a) a first regulatory element operably linked to a tracr mate sequence and one or more insertion sites for inserting one or more guide sequences upstream of the tracr mate sequence, wherein when expressed, the guide sequence directs sequence-specific binding of a CRISPR complex to a target sequence in a eukaryotic cell, wherein the CRISPR complex comprises a CRISPR enzyme complexed with (1) the guide sequence that is hybridized to the target sequence, and (2) the tracr mate sequence that is hybridized to the tracr sequence; and/or (b) a second regulatory element operably linked to an enzyme-coding sequence encoding said CRISPR enzyme comprising a nuclear localization sequence. In some embodiments, the kit comprises components (a) and (b) located on the same or different vectors of the system; and (c) at least one compound as described herein.

Elements may be provided individually or in combinations, and may be provided in any suitable container, such as a vial, a bottle, or a tube. In some embodiments, the kit includes instructions in one or more languages, for example in more than one language. Reagents may be provided in any suitable container. For example, a kit may provide one or more reaction or storage buffers. Reagents may be provided in a form that is usable in a particular assay, or in a form that requires addition of one or more other components before use (e.g. in concentrate or lyophilized form). A buffer can be any buffer, including but not limited to a sodium carbonate buffer, a sodium bicarbonate buffer, a borate buffer, a Tris buffer, a MOPS buffer, a HEPES buffer, and combinations thereof. In some embodiments, the buffer is alkaline. In some embodiments, the buffer has a pH from about 7 to about 10. In some embodiments, the kit comprises one or more oligonucleotides corresponding to a guide sequence for insertion into a vector so as to operably link the guide sequence and a regulatory element. In some embodiments, the kit comprises a homologous recombination template polynucleotide.

In some embodiments, the present disclosure provides a compound of the formula

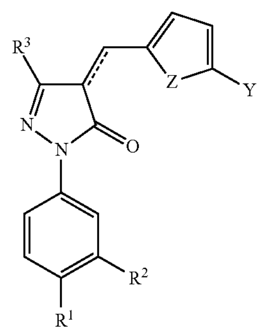

wherein

Z is O or S;

$R^1$ and $R^2$ are independently selected from the group consisting of H, halogen, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, 5- to 7-membered heteroaryl, —$OR^6$, —CN, —$NO_2$, —$C(O)R^6$, —$CO_2R^6$, —$C(O)NR^6R^7$, —$OS(O)R^6$, —$OS(O)_2R^6$, —$SR^6$, —$S(O)R^6$, —$S(O)_2R^6$, —$S(O)NR^6R^7$, —$S(O)_2NR^6R^7$, —$OS(O)NR^6R^7$, —$OS(O)_2NR^6R^7$, and —$NR^6R^7$; wherein each hydrogen atom in $C_1$-$C_6$ alkyl, $C_2$-$C_6$ alkenyl, $C_2$-$C_6$ alkynyl or $C_3$-$C_6$ cycloalkyl is independently optionally substituted with halogen;

$R^3$ is H, halogen, or $C_1$-$C_6$ alkyl, wherein each hydrogen atom in $C_1$-$C_6$ alkyl, $C_2$-$C_6$ alkenyl, $C_2$-$C_6$ alkynyl or $C_3$-$C_6$ cycloalkyl is independently optionally substituted with halogen;

Y is —$C(O)NR^4R^5$ or phenyl, wherein each hydrogen atom in phenyl is optionally substituted with halogen, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, 5- to 7-membered heteroaryl, —$OR^4$, —CN, —$NO_2$, —$C(O)R^4$, —$CO_2R^4$, —$C(O)NR^4R^5$, —$OS(O)R^4$, —$OS(O)_2R^4$, —$SR^4$, —$S(O)R^4$, —$S(O)_2R^4$, —$S(O)NR^4R^5$, 0173$S(O)_2NR^4R^5$, —$OS(O)NR^4R^5$, —$OS(O)_2NR^4R^5$, and —$NR^4R^5$, or two adjacent hydrogen atoms on phenyl are optionally substituted with a group that combines with the carbon atoms to which they are attached to form a 5- to 7-membered heterocycloalkyl ring;

$R^4$ and $R^5$ are each independently selected from the group consisting of H, $C_1$-$C_6$ alkyl, $C_2$-$C_6$ alkenyl, $C_2$-$C_6$ alkynyl, $C_3$-$C_6$ cycloalkyl, —$C_1$-$C_6$ alkyl-($C_3$-$C_6$ cycloalkyl), —$C_1$-$C_6$ alkyl-($C_6$-$C_{10}$ aryl), 3- to 7-membered heterocycloalkyl, $C_6$-$C_{10}$ aryl and 5- to 7-membered heteroaryl, wherein each hydrogen atom in $C_1$-$C_6$ alkyl, $C_2$-$C_6$ alkenyl, $C_2$-$C_6$ alkynyl, $C_3$-$C_6$ cycloalkyl, —$C_1$-$C_6$ alkyl-($C_3$-$C_6$ cycloalkyl) or —$C_1$-$C_6$ alkyl-($C_6$-$C_{10}$ aryl) is independently optionally substituted with halogen, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, 5- to 7-membered heteroaryl, —$OR^8$, —CN, —$NO_2$, —$C(O)R^8$, —$CO_2R^8$, —$C(O)NR^8R^9$, —$OS(O)R^8$, —$OS(O)_2R^8$, —$SR^8$, —$S(O)R^8$, —$S(O)_2R^8$, —$S(O)NR^8R^9$, —$S(O)_2NR^8R^9$, —$OS(O)NR^8R^9$, —$OS(O)_2NR^8R^9$, and —$NR^8R^9$;

each $R^6$, $R^7$, $R^8$ and $R^9$ is independently selected from the group consisting of H, $C_1$-$C_6$ alkyl, $C_2$-$C_6$ alkenyl, $C_2$-$C_6$ alkynyl, $C_3$-$C_6$ cycloalkyl, —$C_1$-$C_6$ alkyl-($C_3$-$C_6$ cycloalkyl), —$C_1$-$C_6$ alkyl-($C_6$-$C_{10}$ aryl), 3- to 7-membered heterocycloalkyl and $C_6$-$C_{10}$ aryl; $C_1$-$C_6$ alkyl, $C_2$-$C_6$ alkenyl, $C_2$-$C_6$ alkynyl, $C_3$-$C_6$ cycloalkyl, —$C_1$-$C_6$ alkyl-($C_3$-$C_6$ cycloalkyl) or —$C_1$-$C_6$ alkyl-($C_6$-$C_{10}$ aryl) is independently optionally substituted with halogen, and ==== is either a single bond or a pi-bond, with at least one cell comprising at least one programmable nuclease.

In some embodiments, Y is —$C(O)NR^4R^5$ or phenyl. In some embodiments, phenyl is of the formula

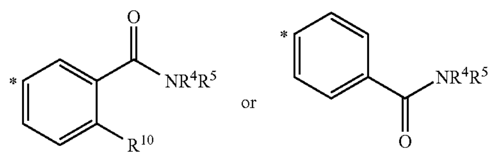

wherein $R^4$, $R^5$ and $R^{10}$ are as defined herein, and * represents a covalent bond to the compound of the formula II. In some embodiments, Y is —$C(O)NR^4R^5$ or phenyl, wherein each hydrogen atom in phenyl is optionally substituted with halogen, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, 5- to 7-membered heteroaryl, —$OR^4$, —CN, —$NO_2$, —$C(O)R^4$, —$CO_2R^4$, —$C(O)NR^4R^5$, —$OS(O)R^4$, —$OS(O)_2R^4$, —$SR^4$, —$S(O)R^4$, —$S(O)_2R^4$, —$S(O)NR^4R^5$, 0173$S(O)_2NR^4R^5$, —$OS(O)NR^4R^5$, —$OS(O)_2NR^4R^5$, and —$NR^4R^5$, or two adjacent hydrogen atoms on phenyl are optionally substituted with a group that combines with the carbon atoms to which they are attached to form a 5- to 7-membered heterocycloalkyl ring. In some embodiments, Y is —$C(O)NR^4R^5$.

In some embodiments, compounds described herein are of the formula Ia,

Ia

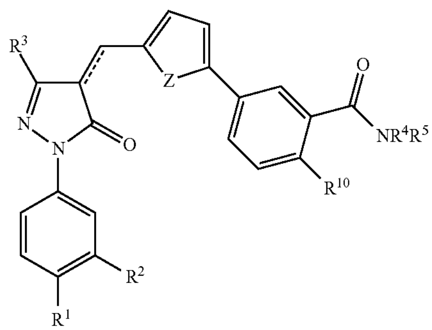

wherein each of Z, $R^1$, $R^2$, $R^3$, $R^4$, $R^5$ and $R^{10}$ are as defined herein.

In some embodiments, compounds described herein are of the formula Ib

Ib

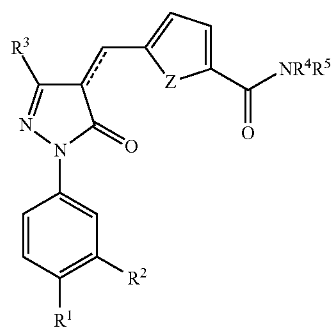

wherein each of Z, $R^1$, $R^2$, $R^3$, $R^4$ and $R^5$ are as defined herein.

In some embodiments, compounds described herein are of the formula Ic

Ic

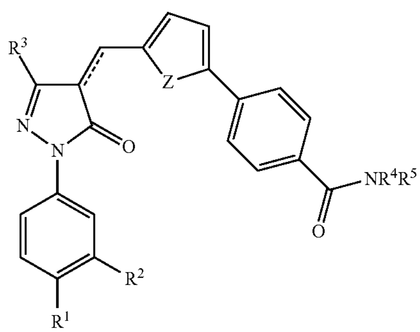

wherein each of Z, $R^1$, $R^2$, $R^3$, $R^4$ and $R^5$ are as defined herein.

In some embodiments, Z is O. In some embodiments, Z is S. In some embodiments, $R^4$ is $C_6$-$C_{10}$ aryl, wherein each hydrogen atom in $C_6$-$C_{10}$ aryl is independently optionally substituted with halogen, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, 5- to 7-membered heteroaryl, —$OR^8$, —CN, —$NO_2$, —$C(O)R^8$, —$CO_2R^8$, —$C(O)NR^8R^9$, —$OS(O)R^8$, —$OS(O)_2R^8$, —$SR^8$, —$S(O)R^8$, —$S(O)_2R^8$, —$S(O)NR^8R^9$, —$S(O)_2NR^8R^9$, —$OS(O)NR^8R^9$, —$OS(O)_2NR^8R^9$, and —$NR^8R^9$. In some embodiments, $R^4$ is $C_6$-$C_{10}$ aryl, substituted with one substituent selected from the group consisting of halogen, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, 5- to 7-membered heteroaryl, —$OR^8$, —CN, —$NO_2$, —$C(O)R^8$, —$CO_2R^8$, —$C(O)NR^8R^9$, —$OS(O)R^8$, —$OS(O)_2R^8$, —$SR^8$, —$S(O)R^8$, —$S(O)_2R^8$, —$S(O)NR^8R^9$, —$S(O)_2NR^8R^9$, —$OS(O)NR^8R^9$, —$OS(O)_2NR^8R^9$, and —$NR^8R^9$. In some embodiments, the one substituent is in the para-position. In some embodiments, the one substituent is in the meta-position. In some embodiments, $R^4$ is $C_6$-$C_{10}$ aryl, substituted with two substituents independently selected from the group consisting of halogen, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, 5- to 7-membered heteroaryl, —$OR^8$, —CN, —$NO_2$, —C(O)$R^8$, —$CO_2R^8$, —C(O)$NR^8R^9$, —OS(O)$R^8$, —OS$(O)_2R^8$, —$SR^8$, —S(O)$R^8$, —S$(O)_2R^8$, —S(O)$NR^8R^9$, —S$(O)_2NR^8R^9$, —OS(O)$NR^8R^9$, —OS$(O)_2NR^8R^9$, and —$NR^8R^9$.

In some embodiments, $R^4$ is $C_6$-$C_{10}$ aryl, wherein $C_6$-$C_{10}$ aryl is substituted with at least one halogen, or —$OR^8$. In some embodiments, $R^4$ is phenyl, wherein each hydrogen atom in phenyl is independently optionally substituted with halogen, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, 5- to 7-membered heteroaryl, —$OR^8$, —CN, —$NO_2$, —C(O)$R^8$, —$CO_2R^8$, —C(O)$NR^8R^9$, —OS(O)$R^8$, —OS$(O)_2R^8$, —$SR^8$, —S(O)$R^8$, —S$(O)_2R^8$, —S(O)$NR^8R^9$, —S$(O)_2NR^8R^9$, —OS(O)$NR^8R^9$, —OS$(O)_2NR^8R^9$, or —$NR^8R^9$. In some embodiments, $R^4$ is phenyl, substituted with on substituent selected from the groups consisting of halogen, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, 5- to 7-membered heteroaryl, —$OR^8$, —CN, —$NO_2$, —C(O)$R^8$, —$CO_2R^8$, —C(O)$NR^8R^9$, —OS(O)$R^8$, —OS$(O)_2R^8$, —$SR^8$, —S(O)$R^8$, —S$(O)_2R^8$, —S(O)$NR^8R^9$, —S$(O)_2NR^8R^9$, —OS(O)$NR^8R^9$, —OS$(O)_2NR^8R^9$, and —$NR^8R^9$. In some embodiments, the one substituent is in the para-position. In some embodiments, the one substituent is in the meta-position. In some embodiments, $R^4$ is phenyl, substituted with two substituents independently selected from the group consisting of halogen, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, 5- to 7-membered heteroaryl, —$OR^8$, —CN, —$NO_2$, —C(O)$R^8$, —$CO_2R^8$, —C(O)$NR^8R^9$, —OS(O)$R^8$, —OS$(O)_2R^8$, —$SR^8$, —S(O)$R^8$, —S$(O)_2R^8$, —S(O)$NR^8R^9$, —S$(O)_2NR^8R^9$, —OS(O)$NR^8R^9$, —OS$(O)_2NR^8R^9$, and —$NR^8R^9$.

In some embodiments, $R^4$ is phenyl substituted with at least one halogen, or —$OR^8$.

In some embodiments, $R^4$ is —$C_1$-$C_6$ alkyl-($C_3$-$C_6$ cycloalkyl). In some embodiments, $R^4$ is —$C_1$-$C_6$ alkyl-($C_6$-$C_{10}$ aryl), and each hydrogen atom in $C_6$-$C_{10}$ aryl is independently optionally substituted with halogen, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, 5- to 7-membered heteroaryl, —$OR^8$, —CN, —$NO_2$, —C(O)$R^8$, —$CO_2R^8$, —C(O)$NR^8R^9$, —OS(O)$R^8$, —OS$(O)_2R^8$, —$SR^8$, —S(O)$R^8$, —S$(O)_2R^8$, —S(O)$NR^8R^9$, —S$(O)_2NR^8R^9$, —OS(O)$NR^8R^9$, —OS$(O)_2NR^8R^9$, or —$NR^8R^9$. In some embodiments, $R^4$ is —$C_1$-$C_6$ alkyl-($C_6$-$C_{10}$ aryl), substituted one substituent selected from the groups consisting of halogen, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, 5- to 7-membered heteroaryl, —$OR^8$, —CN, —$NO_2$, —C(O)$R^8$, —$CO_2R^8$, —C(O)$NR^8R^9$, —OS(O)$R^8$, —OS$(O)_2R^8$, —$SR^8$, —S(O)$R^8$, —S$(O)_2R^8$, —S(O)$NR^8R^9$, —S$(O)_2NR^8R^9$, —OS(O)$NR^8R^9$, —OS$(O)_2NR^8R^9$, and —$NR^8R^9$. In some embodiments, the one substituent is in the para-position. In some embodiments, the one substituent is in the meta-position. In some embodiments, $R^4$ is —$C_1$-$C_6$ alkyl-($C_6$-$C_{10}$ aryl), substituted two substituents independently selected from the groups consisting of halogen, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, 5- to 7-membered heteroaryl, —$OR^8$, —CN, —$NO_2$, —C(O)$R^8$, —$CO_2R^8$, —C(O)$NR^8R^9$, —OS(O)$R^8$, —OS$(O)_2R^8$, —$SR^8$, —S(O)$R^8$, —S$(O)_2R^8$, —S(O)$NR^8R^9$, —S$(O)_2NR^8R^9$, —OS(O)$NR^8R^9$, —OS$(O)_2NR^8R^9$, and —$NR^8R^9$.

In some embodiments, $R^4$ is —$C_1$-$C_6$ alkyl-($C_6$-$C_{10}$ aryl), wherein $C_6$-$C_{10}$ aryl is substituted with at least one halogen, or —$OR^8$.

In some embodiments, $R^4$ is benzyl, wherein each hydrogen atom in benzyl is independently optionally substituted with halogen, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, 5- to 7-membered heteroaryl, —$OR^8$, —CN, —$NO_2$, —C(O)$R^8$, —$CO_2R^8$, —C(O)$NR^8R^9$, —OS(O)$R^8$, —OS$(O)_2R^8$, —$SR^8$, —S(O)$R^8$, —S$(O)_2R^8$, —S(O)$NR^8R^9$, —S$(O)_2NR^8R^9$, —OS(O)$NR^8R^9$, —OS$(O)_2NR^8R^9$, and —$NR^8R^9$. In some embodiments, $R^4$ is benzyl, substituted with one substituent selected from the group consisting of halogen, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, 5- to 7-membered heteroaryl, —$OR^8$, —CN, —$NO_2$, —C(O)$R^8$, —$CO_2R^8$, —C(O)$NR^8R^9$, —OS(O)$R^8$, —OS$(O)_2R^8$, —$SR^8$, —S(O)$R^8$, —S$(O)_2R^8$, —S(O)$NR^8R^9$, —S$(O)_2NR^8R^9$, —OS(O)$NR^8R^9$, —OS$(O)_2NR^8R^9$, and —$NR^8R^9$. In some embodiments, the one substituent is in the para-position. In some embodiments, the one substituent is in the meta-position. In some embodiments, $R^4$ is benzyl, substituted with two substituents independently selected from the group consisting of halogen, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, 5- to 7-membered heteroaryl, —$OR^8$, —CN, —$NO_2$, —C(O)$R^8$, —$CO_2R^8$, —C(O)$NR^8R^9$, —OS(O)$R^8$, —OS$(O)_2R^8$, —$SR^8$, —S(O)$R^8$, —S$(O)_2R^8$, —S(O)$NR^8R^9$, —S$(O)_2NR^8R^9$, —OS(O)$NR^8R^9$, —OS$(O)_2NR^8R^9$, and —$NR^8R^9$.

In some embodiments, $R^4$ is benzyl substituted with at least one halogen, or —$OR^8$.

In some embodiments, $R^4$ selected from the group consisting of

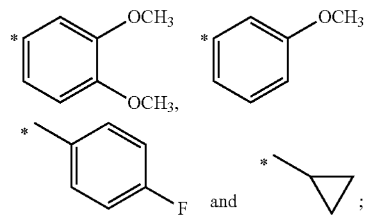

wherein * represent the point of attachment of $R^4$.

In some embodiments, $R^5$ is H. In some embodiments, $R^3$ is $C_1$-$C_6$ alkyl. In some embodiments, $R^3$ is methyl. In some embodiments, $R^1$ and $R^2$ are each independently H, 5- to 7-membered heteroaryl, —CN, —$CO_2R^6$ or —S$(O)_2NR^6R^7$, provided that at least one of $R^1$ and $R^2$ is not H. In some embodiments, $R^1$ is H and $R^2$ is 5- to 7-membered heteroaryl, —CN or —$CO_2R^6$. In some embodiments, $R^1$ is —$CO_2R^6$ or —S$(O)_2NR^6R^7$, and $R^2$ is H. In some embodiments, $R^2$ is —$CO_2R^6$, and $R^6$ is H. In some embodiments, $R^2$ is —$CO_2R^6$, and $R^6$ is ethyl. In some embodiments, $R^1$ is —$CO_2R^6$, and $R^6$ is H. In some embodiments, $R^1$ is —$CO_2R^6$, and $R^6$ is ethyl. In some embodiments, $R^1$ is —S$(O)_2NR^6R^7$, and $R^6$ and $R^7$ are H. In some embodiments, $R^2$ is 5-tetrazole. In some embodiments, $R^{10}$ is chloro. In some embodiments, ⚋ is a single bond. In some embodiments, ⚋ is a pi-bond.

Chemical Synthesis

General Synthesis of X80 and Derivatives

All chemicals used for synthesis were purchased from Aldrich, Alfa Aesar, Across, Fisher Scientific, AK Scientific and Combi-Blocks Chemical Co. (USA) and used without further purification. Anhydrous solvents were obtained from Fisher Scientific or Aldrich and used directly. All reactions involving air- or moisture-sensitive reagents were performed under a nitrogen atmosphere. $^1$H NMR spectra were recorded at 300 MHz and 500 MHz using Bruker AV NMR spectrometer. $^{13}$C NMR spectra were recorded at 75 MHz and 125 MHz using Bruker AV NMR spectrometer. The chemical shifts were reported as δ ppm relative to TMS, using the residual solvent peak as the reference unless otherwise noted. All coupling constants (J) are given in Hertz. Data are reported as follows: chemical shift, multiplicity (s=singlet, d=doublet, t=triplet, q=quartet, br=broad, m=multiplet), number of protons and coupling constants. Thin layer chromatography was performed on using Merck silica gel 60 F-254 thin layer plates, which were developed using one of the following techniques: UV fluorescence (254 nm), alkaline potassium permanganate solution (0.5% w/v) or ninhydrin (0.2% w/v) and Iodine vapors. Automated flash column chromatography was carried out on prepacked silica cartridges using the indicated solvent system on Biotage Isolera chromatography system. Target compounds were crystallized in ethanol, solid was collected, washed with EtOAc and then hot solutions of 20-30% EtOAc in hexanes to afford red to orange solids. If necessary, the products were purified with automated flash column chromatography. The chemical purity of target compounds was ≥95% determined by HPLC coupled to electrospray ionization mass spectrometry (LC/ESI-MS) analysis. LC-MS analyses and compounds purity data were obtained using an Agilent 6130 Quadrupole LC-MS connected to an Agilent 1200 HPLC system and both instruments were connected to an Agilent diode array detector. A C-18 reversed phase column (Vydac monomeric/Phenomenex/Kinetex 2.6 μM XB-C18, 50×4.6 mm) was used as stationary phase, water and methanol/acetonitrile (both containing 0.1 to 0.25% TFA) was used as mobile phase (gradient: 0-100% methanol, flow 0.8 mL/min, run time 15 min), and UV absorbance at the fixed wavelength of 254 nm and positive and negative ESI-MS data were recorded. The retention time and corresponding ESI-MS data were used as identity of molecules. HRMS data were obtained using Waters/Macromass LCT electrospray ionization (ESI) on a time of flight (TOF) mass spectrometer at the Mass Spectrometry Facility at Indiana University Chemistry Department (http://msf.chem.indiana.edu).

Example 1

General Synthetic Scheme of (Z)-2-Chloro-5-(5-((1-(3/4-(ethoxycarbonyl)phenyl)-3-methyl-5-oxo-1H-pyrazol-4(5H)-ylidene)methyl)furan-2-yl)benzoic acid Scheme 1

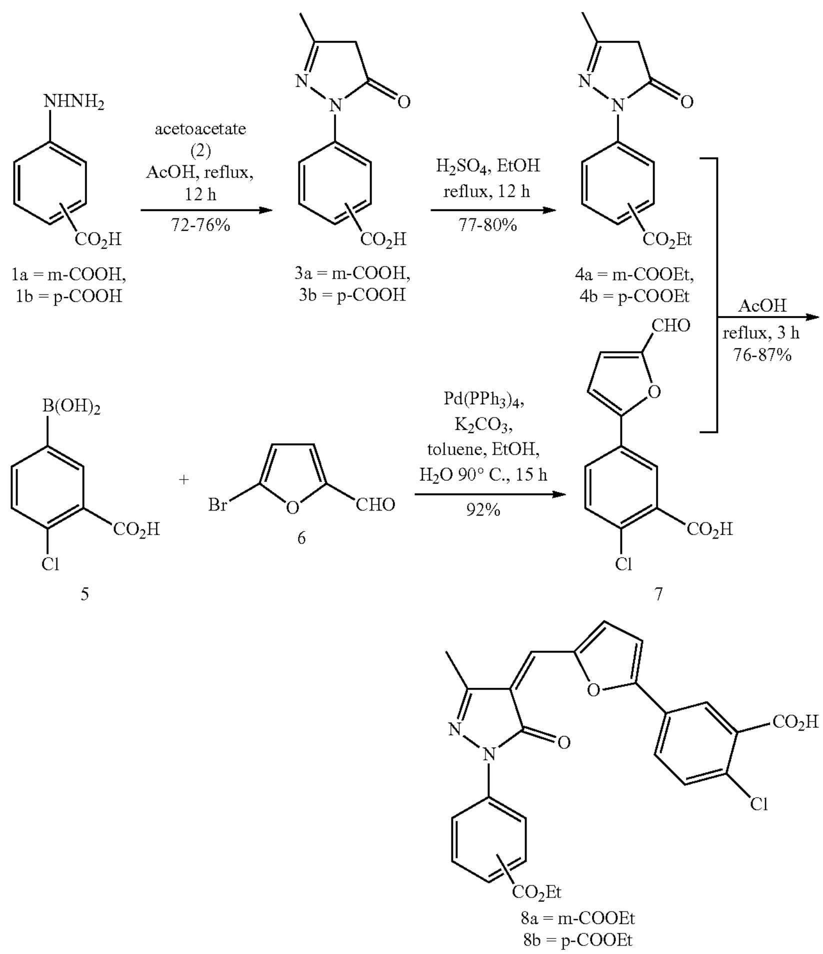

1a = m-COOH, 1b = p-COOH

3a = m-COOH, 3b = p-COOH

4a = m-COOEt, 4b = p-COOEt

5

6

7

8a = m-COOEt
8b = p-COOEt

Step 1: Synthesis of 3-(3-Methyl-5-oxo-4,5-dihydro-1H-pyrazol-1-yl)benzoic acid (3a)

Ethyl acetoacetate 2 (2.01 mL, 1.2 equiv.) was added to a solution of 3-hydrazino benzoic acid (2 gm, 1 equiv.) in glacial acetic acid (30 mL) under an argon atmosphere. After addition, the reaction mixture was heated at reflux with stirring for 12 h. Once the reaction was allowed to cool to room temperature, the reaction mixture was concentrated in vacuo resulting in the formation of a precipitate. The solid was filtered and washed with 5% MeOH in DCM (2 times) and then two times with DCM to obtain off-white solid (2.06 gm, 72% yield, require no further purification). TLC: 4% MeOH in DCM, $R_f$=0.42 visualized with UV.

$^1$H NMR (500 MHz, DMSO): δ 13.22 (brs, 1H, COOH), 8.36 (s, 1H), 8.05 (d, 1H, J=8.5 Hz), 7.94 (d, 1H, J=8.0 Hz), 7.70 (t, 1H, J=8.0 and 16 Hz), 5.97 (s, 1H), 2.45 (s, 3H); $^{13}$C NMR (125 MHz, DMSO): δ 166.48, 158.79, 154.09, 150.10, 144.90, 136.81, 132.15, 129.96, 127.57, 124.16, 120.66, 104.64, 102.19, 19.12, 14.25.

Alternate Step 1: Synthesis of 4-(3-Methyl-5-oxo-4,5-dihydro-1H-pyrazol-1-yl)benzoic acid (3b)

3b was prepared by an above described procedure using 4-hydrazinobenzoic acid hydrochloride (2 gm) as a starting material. Off-white solid, (1.76 gm, 76% yield, require no further purification). TLC: 4% MeOH in DCM, $R_f$=0.42 visualized with UV.

$^1$H NMR (300 MHz, DMSO): δ 12.87 (brs, 1H, COOH), 7.98 (d, 2H, J=8.8 Hz), 7.88 (d, 2H, J=8.4 Hz), 5.38 (s, 1H), 2.12 (s, 3H).

Step 2: Synthesis of Ethyl 3-(3-methyl-5-oxo-4,5-dihydro-1H-pyrazol-1-yl)benzoate (4a)

To a stirred suspension of 3-(3-Methyl-5-oxo-4,5-dihydro-1H-pyrazol-1-yl)benzoic acid 3a (1.95 gm) in anhydrous ethanol (30 mL) was added a catalytic amount of concentrated sulfuric acid (1.5 mL) slowly under an argon atmosphere. The reaction mixture was refluxed for 12 h and then it was allowed to cool to room temperature. The solvent was removed under vacuum, the obtained residue was dissolved in ethyl acetate and washed successively with a saturated $NaHCO_3$ (2×10 mL), water and brine solution. The organic layer was dried over $Na_2SO_4$ and concentrated under reduced pressure. The crude residue was purified by Biotage Flash chromatography using 0 to 50% EtOAc in hexanes as the eluent to furnish ethyl 3-(3-methyl-5-oxo-4,5-dihydro-1H-pyrazol-1-yl)benzoate 4a as a red oil (1.69 gm, 77% yield). TLC: 45% EtOAc in hexanes, $R_f$=0.44 visualized with UV.

$^1$H NMR (300 MHz, $CDCl_3$): δ 8.41 (s, 1H), 8.05 (d, 1H, J=8.2 Hz), 7.78 (d, 1H, J=8.0 Hz), 7.38 (t, 1H, J=7.95 and 15.99 Hz), 4.35-4.28 (q, 2H), 3.37 (s, 2H), 2.11 (s, 3H), 1.33 (t, 3H, J=7.11 and 14.25 Hz); $^{13}$C NMR (75 MHz, $CDCl_3$): δ 170.70, 166.14, 156.84, 138.18, 131.22, 128.82, 125.77, 122.69, 119.46, 61.10, 43.02, 16.93, 14.29.

Alternate Step 2: Synthesis of Ethyl 4-(3-methyl-5-oxo-4,5-dihydro-1H-pyrazol-1-yl)benzoate (4b)

4b was prepared by an above described procedure using 3b (1.60 gm) as a starting material. White solid, (1.44 gm, 80% yield). TLC: 40% EtOAc in hexanes, $R_f$=0.44 visualized with UV.

$^1$H NMR (300 MHz, $CDCl_3$): δ 8.05 (d, 2H, J=8.97 Hz), 8.01 (d, 2H, J=8.94 Hz), 4.40-4.33 (q, 2H), 3.46 (s, 2H), 2.22 (s, 3H), 1.39 (t, 3H, J=7.11 and 14.25 Hz); $^{13}$C NMR (75 MHz, $CDCl_3$): δ 170.78, 166.18, 156.89, 141.69, 130.54, 126.42, 117.61, 60.90, 43.17, 17.09, 14.36.

Step 3: Synthesis of 2-Chloro-5-(5-formylfuran-2-yl)benzoic acid (7)

A solution of $K_2CO_3$ (2.37 gm, 3 equiv.) in water (10 mL) was added to a mixture of 4-chloro-3-carboxyphenylboronic acid (1.37 gm, 1.2 equiv.) and 5-bromo-2-furaldehyde (1 gm, 1 equiv.) in toluene/ethanol (60 mL). The mixture was degassed with argon for 5 minute and then $Pd(PPh_3)_4$ (330 mg, 0.05 equiv.) was added. The reaction mixture was stirred at 90° C. for 15 h. The reaction mixture was cooled to room temperature, filtered through Celite and was with water (2×10 mL). The pH of solution was adjusted to 1-2 by addition of 6N HCl solution. The precipitated reaction mixture was extracted with dichloromethane (3×100 mL); the combined organic fractions were washed with brine, dried over anhydrous $Na_2SO_4$, and concentrated under reduced pressure. The crude product was triturated with 20-30% EtOAc in hexanes (2 times), solid was filtered to afford 2-chloro-5-(5-formylfuran-2-yl)benzoic acid 7 (1.24 gm, 87% yield) as an off-white solid. TLC: 60% EtOAc in hexanes, $R_f$=0.40 visualized with UV and $KMnO_4$ solution.

$^1$H NMR (300 MHz, DMSO): δ 13.74 (brs, 1H, COOH), 9.63 (s, 1H, CHO), 8.23 (d, 1H, J=2.22 Hz), 8.01 (dd, 1H, J=2.28 and 8.43 Hz), 7.70 (d, 1H, J=8.34 Hz), 7.67 (d, 1H, J=2.85 Hz), 7.45 (d, 1H, J=3.75 Hz); $^{13}$C NMR (75 MHz, DMSO): δ 178.64, 166.63, 156.44, 152.47, 132.93, 132.78, 132.13, 129.00, 128.10, 127.23, 110.56.

Step 4: Synthesis of (Z)-2-Chloro-5-(5-((1-(3-(ethoxycarbonyl)phenyl)-3-methyl-5-oxo-1H-pyrazol-4(5H)-ylidene)methyl)furan-2-yl)benzoic acid (8a)

Ethyl 3-(3-methyl-5-oxo-4,5-dihydro-1H-pyrazol-1-yl) benzoate 4a (1 gm, 1 equiv.) and 2-chloro-5-(5-formylfuran-2-yl)benzoic acid 7 (1.01 gm, 1 equiv.) were dissolved in glacial acetic acid (50 mL). The reaction mixture was heated at reflux with stirring for 3 h. Solvent was removed in vacuo, solid was suspended in EtOH, filtered, washed with EtOH, EtOAc and DCM (2 times each) to obtain a red solid (1.48 gm, 76% yield, require no further purification). TLC: 5% MeOH in DCM, $R_f$=0.45 visualized with UV.

Major Z-isomer data: $^1$H NMR (300 MHz, DMSO): δ 13.75 (brs, 1H, COOH), 8.63 (d, 1H, J=3.87 Hz), 8.48 (t, 1H, J=1.86 and 3.69 Hz), 8.27 (d, 1H, J=2.22 Hz), 8.19 (d, 1H, J=7.08 Hz), 8.01 (dd, 1H, J=2.22 and 8.43 Hz), 7.76-7.64 (m, 3H), 7.56-7.51 (m, 2H), 4.36-4.29 (q, 2H), 2.64 (s, 0.29H, minor isomer), 2.32 (s, 2.71H, major isomer), 1.33 (t, 3H, J= 7.08 and 14.16 Hz); $^{13}$C NMR (75 MHz, DMSO): δ 166.59, 165.88, 162.11, 157.65, 151.64, 150.82, 138.96, 133.15, 132.67, 131.11, 130.91, 130.08, 129.77, 128.96, 127.84, 127.26, 125.17, 122.41, 121.60, 118.43, 112.91, 61.38, 14.65, 13.29.

Alternate Step 4: Synthesis of (Z)-2-Chloro-5-(5-((1-(4-(ethoxycarbonyl)phenyl)-3-methyl-5-oxo-1H-pyrazol-4(5H)-ylidene)methyl)furan-2-yl)benzoic acid (8b)

4b was prepared by an above described procedure using 4b (1 gm, 1 equiv.) and 7 (1.01 gm, 1 equiv.) as starting materials. Red solid, (1.69 gm, 87% yield). TLC: 5% MeOH in DCM, $R_f$=0.48 visualized with UV.

Major Z-isomer data: $^1$H NMR (300 MHz, DMSO): δ 13.72 (brs, 1H, COOH), 8.62 (d, 1H, J=3.84 Hz), 8.33 (d, 1H, J=2.19 Hz), 8.15-7.90 (m, 5H), 7.79 (s, 1H), 7.71 (d, 1H, J=8.49 Hz), 7.58 (d, 1H, J=3.84 Hz), 4.33-4.26 (q, 2H), 2.68 (s, 0.51H, minor isomer), 2.34 (s, 2.49H, major isomer), 1.32 (t, 3H, J=7.11 and 14.19 Hz); $^{13}$C NMR (75 MHz, DMSO): δ 166.60, 165.69, 162.41, 157.81, 152.26, 150.83, 142.42, 133.23, 132.70, 132.18, 130.71, 129.03, 127.87, 127.35, 125.42, 121.39, 117.39, 112.97, 61.01, 14.67, 13.35.

Example 2

Synthesis of X80 [(Z)-5-(5-((1-(3-Carboxyphenyl)-3-methyl-5-oxo-1H-pyrazol-4(5H)-ylidene)methyl)furan-2-yl)-2-chlorobenzoic acid]

Scheme 2

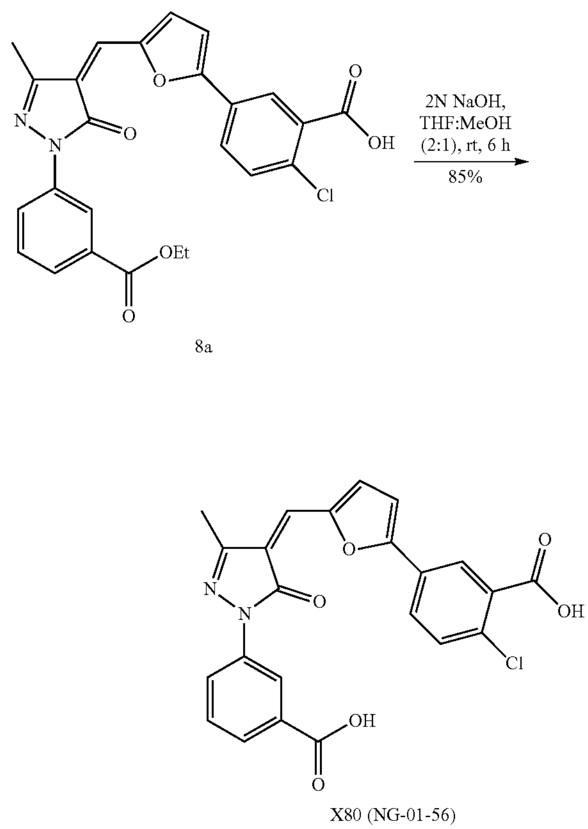

8a

X80 (NG-01-56)

To a stirred suspension of compound 8a (150 mg) in THF:MeOH (2:1, v/v, 10 mL) was added 2N NaOH (1 mL) solution. The reaction mixture was stirred at room temperature for 6 h. Solvent was removed in vacuo and residue was acidified to pH 2-3 using 20% citric acid solution. The product was extracted with EtOAc (3×15 mL). The combined organic extracts was washed with brine, dried over $Na_2SO_4$ and concentrated under reduced pressure. The product was crystallized in EtOAc and triturated with 30% EtOAc in hexanes to afford X-80 (120 mg, 85% yield) as an orange solid.

Example 3

Synthesis of (Z)-Benzyl 2-chloro-5-(5-((1-(3-(ethoxycarbonyl)phenyl)-3-methyl-5-oxo-1H-pyrazol-4(5H)-ylidene)methyl)furan-2-yl)benzoate (NG-01-62)

Scheme 3

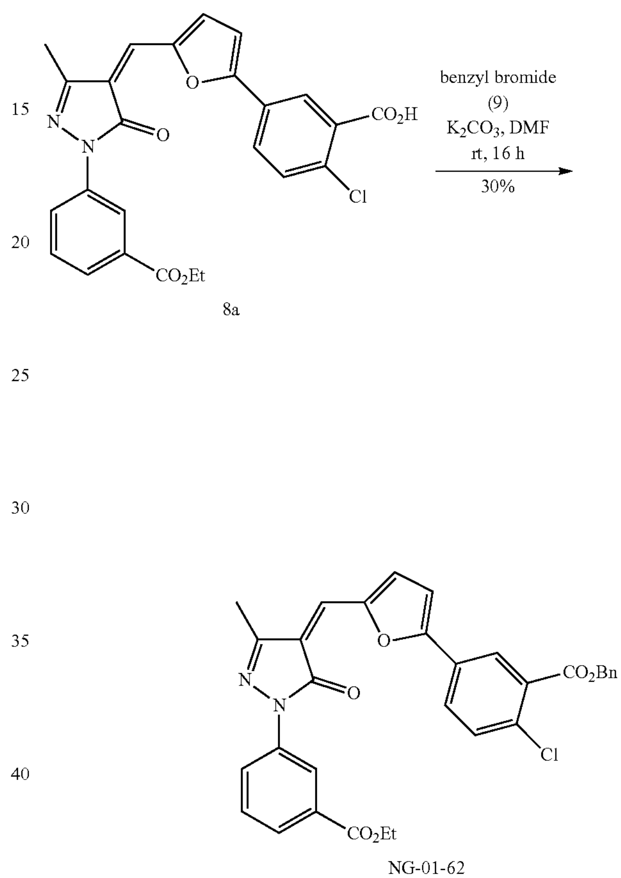

8a

NG-01-62

To a stirred suspension of 8a (150 mg, 1 equiv.) in dry DMF (3 mL) was added $K_2CO_3$ (86 mg, 2 equiv.) under an argon atmosphere. Benzyl bromide (40 μL, 1.1 equiv.) was added to the reaction mixture and stirring was continued for 16 h. The reaction mixture was poured into water and extracted with EtOAc (3×10 mL). The combined organic extracts was washed with brine, dried over $Na_2SO_4$ and concentrated under reduced pressure. The product was crystallized in EtOAc and triturated with 50% EtOAc in hexanes to afford X-80 (53 mg, 30% yield) as a red solid.

$^1$H NMR (500 MHz, $CDCl_3$): δ 8.64 (t, 1H, J=2.0 and 4.0 Hz); 8.30-8.27 (m, 2H), 7.90 (d, 1H, J=8.0 Hz); 7.80 (dd, 1H, J=2.5 and 8.5 Hz); 7.61 (d, 1H, J=8.5 Hz); 7.53-7.43 (m, 7H), 7.25 (d, 1H, J=4.0 Hz); 6.99 (d, 1H, J=4.0 Hz); 5.45 (s, 2H), 4.44-4.41 (q, 2H), 2.65 (s, 2.19H, major isomer), 2.39 (s, 0.81H, minor isomer), 1.44 (t, 1H, J=7.0 and 14.0 Hz); $^{13}$C NMR (125 MHz, $CDCl_3$): δ 166.37, 165.06, 165.02, 164.55, 162.17, 158.54, 157.35, 150.77, 150.33, 150.04, 147.72, 138.66, 135.35, 134.68, 131.30, 130.99, 128.79, 128.54, 127.41, 122.97, 122.44, 119.80, 119.44, 111.48, 110.74, 67.70, 61.09, 14.38, 13.01.

Example 4

Synthesis of Amides 10-19 from 8a and 8b

Scheme 4

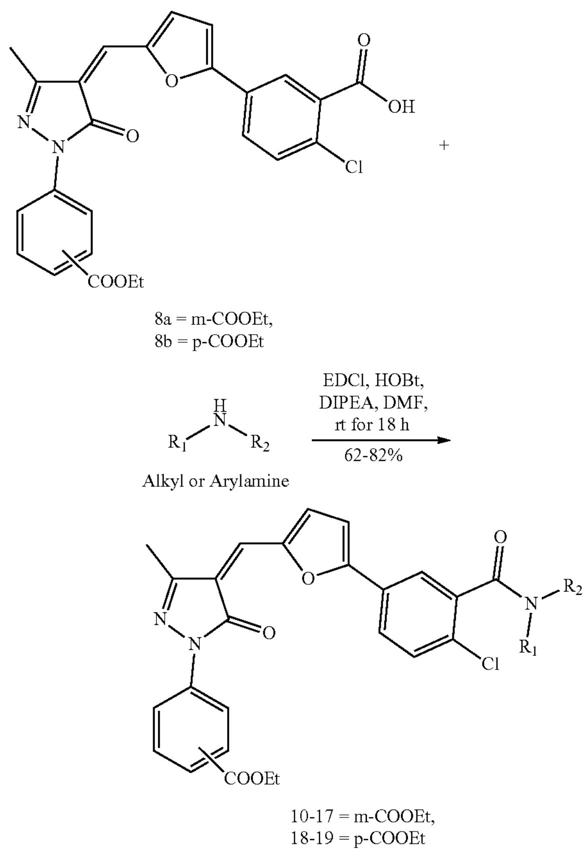

8a = m-COOEt,
8b = p-COOEt 10-17 = m-COOEt,
18-19 = p-COOEt

Synthesis of [(Z)-ethyl 3-(4-((5-(4-chloro-3-((4-fluorobenzyl)carbamoyl)phenyl)furan-2-yl)methylene)-3-methyl-5-oxo-4,5-dihydro-1H-pyrazol-1-yl) benzoate] (10)

Scheme 5

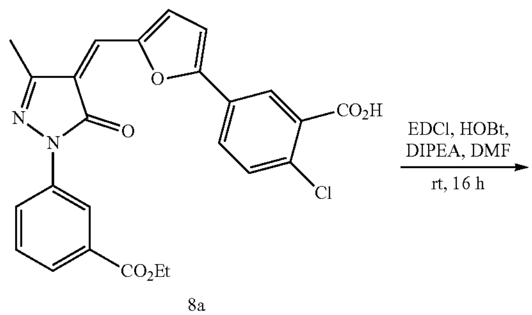

8a

-continued

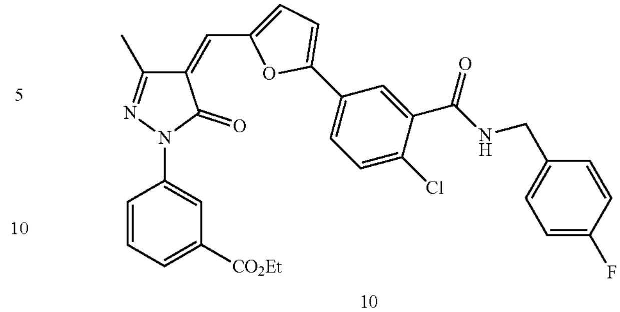

10

To a solution of compound 8a (300 mg, 1 equiv.) in dry DMF (6 mL) was added EDCI.HCl (180 mg, 1.5 equiv), HOBt (127 mg 1.5 equiv.), DIPEA (0.16 mL, 1.5 equiv.) and the mixture was stirred for 30 min at room temperature under an argon atmosphere. 4-Fluorobenzylamine (75 μL, 1.05 equiv.) and DIPEA (0.16 mL, 1.5 equiv.) were added to the reaction mixture. The reaction mixture was stirred at room temperature for 18 h. The reaction mixture was poured into water and extracted with EtOAc (3×20 mL). The combined organic extracts was washed with saturated $NaHCO_3$ (2×10 mL), brine, dried over $Na_2SO_4$ and concentrated under reduced pressure. The product was triturated with mixture of EtOAc in hexanes (2-3 times) to afford 10 (279 mg, 76% yield) as a red solid.

Scheme 6

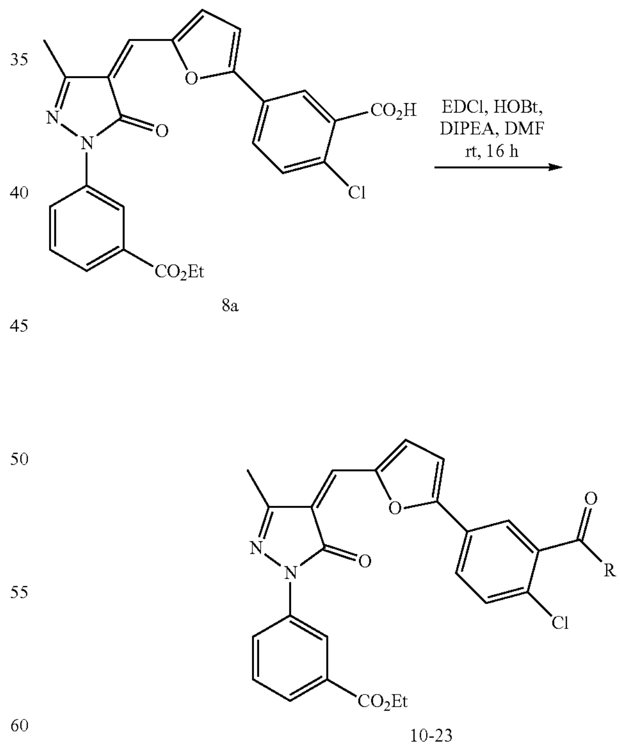

8a 10-23

Compounds 11-19 were synthesized by an above synthetic procedure described for the preparation of compound 10 using appropriate starting materials. Each compound was triturated with the mixture of EtOAc in hexanes (2-3 times) to afford desired compound.

(Z)-Ethyl 3-(4-((5-(4-chloro-3-((3-methoxyphenyl) carbamoyl)phenyl)furan-2-yl)methylene)-3-methyl-5-oxo-4,5-dihydro-1H-pyrazol-1-yl)benzoate (11)

Red solid (226 mg, 62% yield). TLC: 3% MeOH in EtOAc, $R_f$=0.47 visualized with UV Major Z-isomer data: $^1$H NMR (300 MHz, DMSO): δ 10.64 (s, 1H, NH), 8.65 (d, 1H, J=3.81 Hz), 8.52 (t, 1H, J=1.83 and 3.63 Hz), 8.22-8.14 (m, 2H), 8.06 (dd, 1H, J=2.16 and 8.46 Hz), 7.81-7.70 (m, 3H), 7.64-7.53 (m, 2H), 7.43 (s, 1H), 7.29-7.27 (m, 2H), 6.74-6.70 (m, 1H), 4.37-4.30 (q, 2H, $OCH_2$), 3.75 (s, 3H, $OCH_3$), 2.70 (s, 0.58H, minor isomer, $CH_3$), 2.33 (s, 2.42H, major isomer, $CH_3$), 1.33 (t, 3H, J=7.11 and 14.19 Hz, $CH_3$); $^{13}$C NMR (75 MHz, DMSO): δ 165.91, 164.69, 162.20, 160.01, 157.96, 151.75, 150.82, 140.40, 139.00, 138.22, 131.78, 131.52, 131.21, 130.66, 127.96, 125.69, 125.28, 121.63, 118.58, 112.32, 109.89, 105.83, 61.42, 55.51, 14.66, 13.30.

(Z)-Ethyl 3-(4-((5-(4-chloro-3-((cyclopropylmethyl) carbamoyl)phenyl)furan-2-yl)methylene)-3-methyl-5-oxo-4,5-dihydro-1H-pyrazol-1-yl)benzoate (12)

Red solid (249 mg, 75% yield). TLC: 3% MeOH in DCM, $R_f$=0.43 visualized with UV Major Z-isomer data: $^1$H NMR (500 MHz, DMSO): δ 8.68-8.64 (m, 2H), 8.54 (t, 1H, J=1.8 and 3.55 Hz), 8.23-8.20 (m, 1H), 8.01-7.92 (m, 2H), 7.78-7.74 (m, 2H), 7.68 (d, 1H, J=8.3 Hz), 7.60-7.57 (m, 2H), 4.38-4.33 (q, 2H, $OCH_2$), 3.18 (m, 2H, $NHCH_2$), 2.72 (s, 0.64H, minor isomer, $CH_3$), 2.35 (s, 2.36H, major isomer, $CH_3$), 1.35 (t, 3H, J=7.1 and 14.2 Hz, $CH_3$), 1.06-1.0 (m, 1H, CH), 0.49-0.45 (m, 2H, $CH_2$), 0.28-0.25 (m, 2H, $CH_2$); $^{13}$C NMR (125 MHz, DMSO): δ 165.51, 165.44, 161.74, 157.65, 151.27, 150.29, 138.54, 138.14, 131.07, 130.56, 129.68, 129.37, 127.54, 127.29, 126.66, 124.96, 124.80, 112.16, 121.05, 118.16, 112.28, 60.92, 43.24, 14.17, 12.81, 10.65.

(Z)-Ethyl 3-(4-((5-(4-chloro-3-(cyclopropylcarbamoyl)phenyl)furan-2-yl)methylene)-3-methyl-5-oxo-4,5-dihydro-1H-pyrazol-1-yl)benzoate (13)

Red solid (223 mg, 69% yield). TLC: 3% MeOH in DCM, $R_f$=0.46 visualized with UV Major Z-isomer data: $^1$H NMR (300 MHz, DMSO): δ 8.68 (d, 1H, J=4.26 Hz), 8.63 (d, 1H, J=3.6 Hz), 8.52 (s, 1H), 8.22 (d, 1H, J=7.41 Hz), 7.97-7.88 (m, 2H), 7.79-7.73 (m, 2H), 7.67-7.52 (m, 3H), 4.37-4.30 (q, 2H, $OCH_2$), 2-88-2.82 (m, 1H, CH) 2.68 (s, 0.46H, minor isomer, $CH_3$), 2.35 (s, 2.54H, major isomer, $CH_3$), 1.33 (t, 3H, J=7.08 and 14.13 Hz, $CH_3$), 0.75-0.69 (m, 2H, $CH_2$), 0.58-0.53 (m, 2H, $CH_2$); $^{13}$C NMR (75 MHz, DMSO): δ 167.19, 165.92, 162.20, 158.09, 151.76, 150.75, 139.02, 138.83, 138.34, 138.06, 131.04, 130.17, 129.88, 128.05, 127.75, 127.16, 125.51, 125.27, 122.59, 121.50, 118.58, 112.83, 61.42, 23.23, 14.67, 13.33, 6.16.

(Z)-Ethyl 3-(4-((5-(4-chloro-3-(morpholene-4-carbonyl)phenyl)furan-2-yl)methylene)-3-methyl-5-oxo-4,5-dihydro-1H-pyrazol-1-yl)benzoate (14)

Red solid (226 mg, 66% yield). TLC: 3% MeOH in DCM, $R_f$=0.41 visualized with UV Major Z-isomer data: $^1$H NMR (300 MHz, DMSO): δ 8.62 (d, 1H, J=3.81 Hz), 8.50 (t, 1H, J=1.74 and 3.45 Hz), 8.21 (d, 1H, J=7.5 Hz), 7.97-7.87 (m, 2H), 7.77-7.66 (m, 3H), 7.61-7.51 (m, 2H), 4.37-4.29 (q, 2H, $OCH_2$), 3.72 (s, 4H, $2CH_2$), 3.57 (s, 2H, $CH_2$), 3.21 (s, 2H, $CH_2$), 2.67 (s, 0.65H, minor isomer, $CH_3$), 2.32 (s, 2.35H, major isomer, $CH_3$), 1.33 (t, 3H, J=7.11 and 14.16 Hz, $CH_3$); $^{13}$C NMR (75 MHz, DMSO): δ 165.92, 165.43, 162.23, 151.78, 150.80, 139.01, 136.89, 131.04, 130.61, 130.20, 129.27, 128.00, 127.18, 125.32, 124.82, 122.66, 121.63, 118.63, 112.98, 66.39, 61.43, 47.16, 14.67, 13.32.

(Z)-Ethyl 3-(4-((5-(4-chloro-3-(4-methylpiperazine-1-carbonyl)phenyl)furan-2-yl)methylene)-3-methyl-5-oxo-4,5-dihydro-1H-pyrazol-1-yl)benzoate (15)

Red solid (217 mg, 62% yield). TLC: 3% MeOH in DCM, $R_f$=0.43 visualized with UV Major Z-isomer data: $^1$H NMR (300 MHz, DMSO): δ 8.62 (d, 1H, J=3.81 Hz), 8.50 (t, 1H, J=1.83 and 3.63 Hz), 8.21-8.16 (m, 1H), 7.97-7.94 (m, 2H), 7.77-7.64 (m, 3H), 7.58-7.51 (m, 2H), 4.37-4.30 (q, 2H, $OCH_2$), 3.71-3.67 (m, 2H, $CH_2$), 3.22-3.17 (m, 2H, $CH_2$), 2.66 (s, 0.61H, minor isomer, $CH_3$), 2.48-2.44 (m, 2H, $CH_2$), 2.36-2.32 (m, 2H, $CH_2$), 2.32 (s, 2.39H, major isomer, $CH_3$), 2.22 (s, 3H, $NCH_3$), 1.33 (t, 3H, J=7.08 and 14.16 Hz, $CH_3$).

(Z)-Ethyl 3-(4-((5-(4-chloro-3-((tetrahydro-2H-pyran-4-yl)carbamoyl)phenyl)furan-2-yl)methylene)-3-methyl-5-oxo-4,5-dihydro-1H-pyrazol-1-yl) benzoate (16)

Red solid (246 mg, 70% yield). TLC: 3% MeOH in DCM, $R_f$=0.45 visualized with UV Major Z-isomer data: $^1$H NMR (300 MHz, DMSO): δ 8.69 (m, 2H), 8.53 (t, 1H, J=1.71 and 3.51 Hz), 8.26-8.20 (m, 1H), 8.02-7.87 (m, 2H), 7.79 (s, 1H), 7.75 (d, 1H, J=8.1 Hz), 7.69-7.55 (m, 3H), 4.38-4.31 (q, 2H, $OCH_2$), 4.04-3.92 (m, 1H, CH), 3.90-3.84 (m, 2H, $CH_2$), 3.45-3.39 (m, 2H, $CH_2$), 2.71 (s, 0.58H, minor isomer, $CH_3$), 2.34 (s, 2.42H, major isomer, $CH_3$), 1.85-1.75 (m, 2H, $CH_2$), 1.60-1.45 (m, 2H, $CH_2$), 1.33 (t, 3H, J=7.08 and 14.01 Hz, $CH_3$); $^{13}$C NMR (75 MHz, DMSO): δ 166.29, 165.92, 165.37, 162.21, 158.13, 156.81, 152.40, 151.81, 150.77, 146.86, 141.35, 139.03, 138.55, 138.40, 131.41, 131.02, 130.59, 130.24, 127.93, 127.78, 127.16, 125.33, 124.64, 122.65, 121.49, 118.62, 110.44, 66.29, 61.44, 46.06, 32.62, 14.67, 13.36.

(Z)-Ethyl 3-(4-((5-(4-chloro-3-(((tetrahydro-2H-pyran-4-yl)methyl)carbamoyl)phenyl)furan-2-yl) methylene)-3-methyl-5-oxo-4,5-dihydro-1H-pyrazol-1-yl)benzoate (17)

Red solid (267 mg, 74% yield). TLC: 3% MeOH in DCM, $R_f$=0.45 visualized with UV.

Major Z-isomer data: $^1$H NMR (300 MHz, DMSO): δ 8.69-8.63 (m, 2H), 8.53 (s, 1H), 8.22 (d, 1H, J=9.06 Hz), 7.99-7.90 (m, 2H), 7.81-7.74 (m, 1H), 7.77 (s, 1H), 7.67-7.53 (m, 3H), 4.38-4.28 (q, 2H, $OCH_2$), 3.90-3.81 (m, 2H, $CH_2$), 3.32-3.22 (m, 2H, $CH_2$), 3.19-3.13 (m, 2H, $NHCH_2$), 2.72 (s, 0.58H, minor isomer, $CH_3$), 2.34 (s, 2.42H, major isomer, $CH_3$), 1.84-1.71 (m, 1H, CH), 1.69-1.60 (m, 2H, $CH_2$), 1.33 (t, 3H, J=7.08 and 13.95 Hz, $CH_3$), 1.26-1.15 (m, 2H, $CH_2$); $^{13}$C NMR (75 MHz, DMSO): δ 178.58, 166.65, 166.24, 165.92, 162.22, 158.13, 156.80, 152.40, 151.79, 150.77, 146.85, 141.35, 139.02, 138.68, 138.52, 131.72, 131.02, 130.60, 127.95, 127.88, 127.79, 125.30, 124.65, 122.65, 121.51, 119.60, 112.86, 110.42, 108.52, 67.22, 61.43, 45.27, 36.25, 31.22, 14.69, 13.43.

(Z)-Ethyl 4-(4-((5-(4-chloro-3-((cyclopropylmethyl)carbamoyl)phenyl)furan-2-yl)methylene)-3-methyl-5-oxo-4,5-dihydro-1H-pyrazol-1-yl)benzoate (18)

Red solid (364 mg, 82% yield). TLC: 3% MeOH in DCM, $R_f$=0.44 visualized with UV Major Z-isomer data: $^1$H NMR (300 MHz, DMSO): δ 8.74 (t, 1H, J=5.31 and 10.5 Hz), 8.59 (s, 1H), 8.07 (t, 2H, J=8.73 and 17.7 Hz), 8.0 (d, 4H, J=7.83 Hz), 7.75 (s, 1H), 7.66 (d, 1H, J=8.85 Hz), 7.58 (d, 1H, J=3.96 Hz), 4.32-4.25 (q, 2H, $OCH_2$), 3.16 (t, 2H, J=6.09 and 12.42 Hz, $NHCH_2$), 2.68 (s, 0.66H, minor isomer, $CH_3$), 2.32 (s, 2.34H, major isomer, $CH_3$), 1.31 (t, 3H, J=7.11 and 14.16 Hz, $CH_3$), 1.09-0.98 (m, 1H, CH), 0.48-0.42 (m, 2H, $CH_2$), 0.28-0.23 (m, 2H, $CH_2$); $^{13}$C NMR (75 MHz, DMSO): δ 166.00, 166.07, 165.92, 162.49, 158.74, 157.92, 152.39, 150.77, 150.34, 148.97, 142.47, 138.63, 138.42, 131.62, 131.12, 130.77, 127.95, 127.73, 127.20, 125.50, 121.07, 119.60, 117.51, 112.81, 61.06, 43.68, 14.70, 13.39, 11.17, 3.36.

(Z)-ethyl 4-(4-((5-(4-chloro-3-((4-fluorobenzyl)carbamoyl)phenyl)furan-2-yl)methylene)-3-methyl-5-oxo-4,5-dihydro-1H-pyrazol-1-yl)benzoate (19)

Red solid (300 mg, 79% yield). TLC: 3% MeOH in DCM, $R_f$=0.47 visualized with UV Major Z-isomer data: $^1$H NMR (300 MHz, DMSO): δ 9.17 (t, 1H, J=5.88 and 11.76 Hz), 8.62 (s, 1H), 8.16-7.97 (m, 6H), 7.75 (s, 1H), 7.69 (d, 1H, J=8.4 Hz), 7.60 (d, 1H, J= 3.33 Hz), 7.45-7.41 (m, 2H), 7.22-7.18 (m, 2H), 4.49 (d, 2H, J=5.76 Hz, $NHCH_2$), 4.32-4.25 (q, 2H, $OCH_2$), 2.62 (s, 0.74H, minor isomer, $CH_3$), 2.33 (s, 2.26H, major isomer, $CH_3$), 1.31 (t, 3H, J=7.08 and 14.1 Hz, $CH_3$); $^{13}$C NMR (75 MHz, DMSO): δ 166.23, 166.07, 165.23, 162.53, 158.66, 158.19, 154.90, 151.00, 150.74, 150.37, 149.06, 144.85, 142.46, 138.22, 138.04, 135.57, 131.61, 131.34, 130.78, 130.35, 129.73, 127.99, 127.83, 126.52, 125.53, 124.10, 121.33, 118.28, 117.52, 115.91, 115.69, 115.41, 112.89, 61.05, 44.84, 14.69, 13.47.

Example 5

General Synthetic Scheme of Target Compounds

Scheme 7

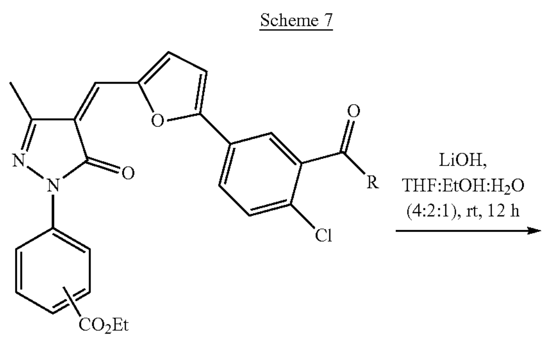

10-19

-continued

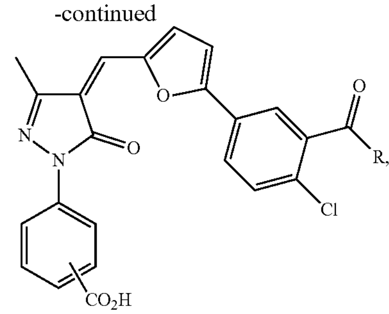

m-COOH = NG-01-64, NG-01-68, NG-01-70, NG-01-78, NG-01-81, NG-01-82, NG-01-99, NG-01-100
p-COOH = NG-01-91, NG-01-92

Synthesis of (Z)-3-(4-((5-(4-Chloro-3-((4-fluorobenzyl)carbamoyl)phenyl)furan-2-yl)methylene)-3-methyl-5-oxo-4,5-dihydro-1H-pyrazol-1-yl)benzoic acid (NG-01-64)

To a stirred suspension of ester 10 (80 mg, 1 equiv.) in THF:EtOH:$H_2O$ (4:2:1, 7 mL) was added LiOH (32 mg, 10 equiv.). The reaction mixture was stirred at room temperature for 12 h. Solvent was removed in vacuo and residue was acidified to pH 2-3 using 20% citric acid solution. The product was extracted with EtOAc (3×15 mL). The combined organic extracts was washed with brine, dried over $Na_2SO_4$ and concentrated under reduced pressure. The product was crystallized in EtOH, solid was collected, washed with EtOAc and then hot solutions of 20-30% EtOAc in hexanes to afford NG-01-64 (47 mg, 62% yield) as a red solid.

Major Z-isomer data: $^1$H NMR (500 MHz, DMSO): δ 9.15 (t, 1H, J=5.8 and 11.7 Hz), 8.68 (d, 1H, J=3.05 Hz), 8.56 (t, 1H, J=1.7 and 3.85 Hz), 8.20 (d, 1H, J=7.45 Hz), 8.04-7.94 (m, 2H), 7.82-7.69 (m, 2H), 7.71 (t, 1H, J=8.15 and 16.45 Hz), 7.62-7.55 (m, 2H), 7.45-7.42 (m, 2H), 7.22-7.17 (m, 2H), 4.49 (d, 2H, J=5.85 Hz, $NHCH_2$), 2.68 (s, 0.76H, $CH_3$), 2.36 (s, 2.24H, $CH_3$).

Compounds NG-01-68, NG-01-70, NG-01-78, NG-01-81, NG-01-82, NG-02-91, NG-02-92, NG-02-99 and NG-02-100 were synthesized by an above synthetic procedure described for the preparation of compound NG-01-64 using appropriate starting materials. Each compound was crystallized in EtOH, solid was collected, washed with EtOAc and then hot solutions of 20-30% EtOAc in hexanes to afford desired final compound. All synthetic compounds for in vitro studies were >95% purity as determined by an absolute quantitative $^1$H NMR spectroscopy (J. Med. Chem., 2014, 57(22), 9219-9219 and J. Med. Chem., 2014, 57(22), 9220-9231).

(Z)-3-(4-((5-(4-Chloro-3-((3-methoxyphenyl)carbamoyl)phenyl)furan-2-yl)methylene)-3-methyl-5-oxo-4,5-dihydro-1H-pyrazol-1-yl)benzoic acid (NG-01-68)

Red solid (111 mg, 69% yield)

Major Z-isomer data: $^1$H NMR (300 MHz, DMSO): δ 13.04 (brs, 1H, COOH), 10.65 (s, 1H, NH), 8.69 (d, 1H, J=3.16 Hz), 8.55 (t, 1H, J=1.95 and 3.5 Hz), 8.31-8.19 (m, 2H), 8.08-7.97 (m, 1H), 7.80-7.70 (m, 3H), 7.65-7.55 (m, 2H), 7.43 (s, 1H), 7.29-7.28 (m, 2H), 6.74-6.69 (m, 1H), 3.76 (s, 3H, $OCH_3$), 2.73 (s, 0.51H, minor isomer, $CH_3$), 2.34 (s, 2.49H, major isomer, $CH_3$); $^{13}C$ NMR (75 MHz, DMSO): δ 172.50, 167.51, 167.28, 165.08, 164.69, 162.22, 160.01, 157.94, 151.59, 140.41, 138.93, 123.24, 132.03, 131.93, 131.22, 130.72, 129.72, 129.47, 125.48, 124.69, 122.30, 121.74, 112.32, 109.89, 105.83, 55.52, 13.30.

(Z)-3-(4-((5-(4-Chloro-3-((cyclopropylmethyl)carbamoyl)phenyl)furan-2-yl)methylene)-3-methyl-5-oxo-4,5-dihydro-1H-pyrazol-1-yl)benzoic acid (NG-01-70)

Red solid (56 mg, 60% yield)

Major Z-isomer data: $^1H$ NMR (300 MHz, DMSO): δ 13.10 (brs, 1H, COOH), 8.71-8.65 (m, 2H), 8.55 (s, 1H), 8.20 (d, 1H, J=7.74 Hz), 8.02-7.94 (m, 2H), 7.83-7.66 (m, 3H), 7.62-7.53 (m, 2H), 3.19-3.13 (m, 2H, $NHCH_2$), 2.73 (s, 0.71H, minor isomer, $CH_3$), 2.35 (s, 2.29H, major isomer, $CH_3$), 1.07-0.95 (m, 1H, CH), 0.48-0.42 (m, 2H, $CH_2$), 0.28-0.23 (m, 2H, $CH_2$); $^{13}C$ NMR (75 MHz, DMSO): δ 167.50, 166.00, 162.22, 158.11, 151.71, 150.80, 138.94, 138.63, 131.93, 131.54, 130.07, 129.73, 128.01, 127.78, 127.15, 125.49, 122.31, 121.61, 118.97, 112.81, 43.71, 13.32, 11.16, 3.73.

(Z)-3-(4-((5-(4-Chloro-3-(cyclopropylcarbamoyl)phenyl)furan-2-yl)methylene)-3-methyl-5-oxo-4,5-dihydro-1H-pyrazol-1-yl)benzoic acid (NG-01-78)

Red solid (64 mg, 68% yield)

Major Z-isomer data: $^1H$ NMR (300 MHz, DMSO): δ 13.12 (brs, 1H, COOH), 8.66-8.63 (m, 2H), 8.54 (t, 1H, J=1.77 and 3.54 Hz), 8.20 (d, 1H, J=8.16 Hz), 8.00-7.94 (m, 2H), 7.82-7.73 (m, 2H), 7.69-7.64 (m, 1H), 7.60-7.53 (m, 2H), 2.89-2.80 (m, 1H, CH), 2.71 (s, 1.10H, minor isomer, $CH_3$), 2.34 (s, 1.90H, major isomer, $CH_3$), 0.77-0.69 (m, 2H, $CH_2$), 0.58-0.53 (m, 2H, $CH_2$); $^{13}C$ NMR (75 MHz, DMSO): δ 167.50, 167.19, 162.21, 158.06, 151.69, 150.78, 138.94, 138.38, 131.93, 131.57, 131.06, 130.15, 129.73, 127.99, 127.78, 127.15, 126.49, 122.29, 121.62, 118.95, 112.81, 23.22, 13.32, 6.18.

(Z)-3-(4-((5-(4-Chloro-3-(morpholine-4-carbonyl)phenyl)furan-2-yl)methylene)-3-methyl-5-oxo-4,5-dihydro-1H-pyrazol-1-yl)benzoic acid (NG-01-81)

Red solid (68 mg, 72% yield). Major Z-isomer data $^1H$ NMR (300 MHz, DMSO): δ 12.94 (brs, 1H, COOH), 8.65 (d, 1H, J=3.45 Hz), 8.54 (s, 1H), 8.20 (d, 1H, J=8.04 Hz), 8.07-7.98 (m, 2H), 7.79-7.68 (m, 3H), 7.62-7.50 (m, 2H), 3.68 (s, 4H, $2CH_2$), 3.56 (s, 2H, $CH_2$), 3.20 (s, 2H, $CH_2$), 2.72 (s, 0.61H, minor isomer, $CH_3$), 2.34 (s, 2.39H, major isomer, $CH_3$).

(Z)-3-(4-((5-(4-Chloro-3-(4-methylpiperazine-1-carbonyl)phenyl)furan-2-yl)methylene)-3-methyl-5-oxo-4,5-dihydro-1H-pyrazol-1-yl)benzoic acid (NG-01-82)

Red solid (64 mg, 69% yield)

Major Z-isomer data: $^1H$ NMR (300 MHz, DMSO): δ 12.68 (brs, 1H, COOH), 8.69 (d, 1H, J=3.95 Hz), 8.55 (t, 1H, J=1.75 and 3.55 Hz), 8.20-8.16 (m, 1H), 7.98-7.94 (m, 2H), 7.81-7.73 (m, 3H), 7.64-7.54 (m, 2H), 3.49-3.44 (m, 2H, $CH_2$), 3.25-3.16 (m, 2H, $CH_2$), 2.66 (s, 0.83H, minor isomer, $CH_3$), 2.50-2.45 (m, 2H, $CH_2$), 2.36-2.31 (m, 2H, $CH_2$), 2.33 (s, 2.17H, major isomer, $CH_3$), 2.21 (s, 3H, $NCH_3$).

(Z)-4-(4-((5-(4-Chloro-3-((cyclopropylmethyl)carbamoyl)phenyl)furan-2-yl)methylene)-3-methyl-5-oxo-4,5-dihydro-1H-pyrazol-1-yl)benzoic acid (NG-02-91)

Red solid (89 mg, 63% yield)

Major Z-isomer data: $^1H$ NMR (300 MHz, DMSO): δ 12.83 (brs, 1H, COOH), 8.67 (t, 1H, J=5.1 and 10.2 Hz), 8.60 (s, 1H), 8.06 (t, 2H, J=8.01 and 14.19 Hz), 8.0 (d, 4H, J=8.55 Hz), 7.76 (s, 1H), 7.67 (d, 1H, J=8.64 Hz), 7.58 (d, 1H, J=3.9 Hz), 3.17 (t, 2H, J=5.7 and 11.4 Hz, $NHCH_2$), 2.70 (s, 0.81H, minor isomer, $CH_3$), 2.33 (s, 2.19H, major isomer, $CH_3$), 1.08-0.94 (m, 1H, CH), 0.49-0.40 (m, 2H, $CH_2$), 0.28-0.22 (m, 2H, $CH_2$); $^{13}C$ NMR (75 MHz, DMSO): δ 167.31, 166.01, 165.91, 162.41, 159.64, 158.22, 152.18, 150.76, 150.29, 149.09, 142.21, 138.60, 138.39, 131.83, 131.05, 130.21, 128.18, 127.74, 127.16, 126.44, 125.45, 121.33, 119.62, 117.542, 112.81, 43.71, 13.35, 11.17, 3.73.

(Z)-4-(4-((5-(4-Chloro-3-((4-fluorobenzyl)carbamoyl)phenyl)furan-2-yl)methylene)-3-methyl-5-oxo-4,5-dihydro-1H-pyrazol-1-yl)benzoic acid (NG-02-92)

Red solid (66 mg, 70% yield)

Isomer data: $^1H$ NMR (300 MHz, DMSO): δ 12.85 (brs, 1H, COOH), 9.17 (t, 1H, J=5.88 and 11.79 Hz), 8.64 (d, 1H, J=3.66 Hz), 8.10-7.92 (m, 6H), 7.83-7.79 (m, 1H), 7.71 (dd, 1H, J=2.67 and 8.4 Hz), 7.62-7.56 (m, 1H), 7.45-7.40 (m, 2H), 7.23-7.15 (m, 2H), 4.48 (d, 2H, J=5.88 Hz, $NHCH_2$), 2.66 (s, 01.65H, $CH_3$), 2.34 (s, 1.35H, $CH_3$); $^{13}C$ NMR (75 MHz, DMSO): δ 167.31, 166.23, 166.11, 165.28, 162.44, 160.10, 159.56, 158.15, 152.22, 150.81, 150.33, 149.13, 142.20, 142.00, 138.22, 138.04, 135.56, 131.83, 131.59, 131.47, 131.17, 131.03, 130.93, 127.83, 127.73, 126.52, 125.90, 125.54, 121.41, 119.71, 117.47, 117.25, 115.69, 115.42, 112.93, 42.32, 13.37.

(Z)-3-(4-((5-(4-Chloro-3-((tetrahydro-2H-pyran-4-yl)carbamoyl)phenyl)furan-2-yl)methylene)-3-methyl-5-oxo-4,5-dihydro-1H-pyrazol-1-yl)benzoic acid (NG-02-99)

Red solid (72 mg, 76% yield)

Major Z-isomer data: $^1H$ NMR (300 MHz, DMSO): δ 13.11 (brs, 1H, COOH), 8.65-8.59 (m, 2H), 8.54 (t, 1H, J=1.71 and 3.42 Hz), 8.20 (d, 1H, J=8.16 Hz), 8.01-7.93 (m, 2H), 7.82-7.73 (m, 2H), 7.70-7.65 (m, 1H), 7.61-7.53 (m, 2H), 4.05-3.95 (m, 1H, CH), 3.91-3.84 (m, 2H, $CH_2$), 3.46-3.41 (m, 2H, $CH_2$), 2.72 (s, 0.77H, minor isomer, $CH_3$), 2.34 (s, 2.23H, major isomer, $CH_3$), 1.86-1.79 (m, 2H, $CH_2$), 1.59-1.46 (m, 2H, $CH_2$); $^{13}C$ NMR (75 MHz, DMSO): δ 167.50, 165.37, 162.19, 158.07, 151.68, 150.79, 138.94, 138.57, 131.92, 131.56, 131.03, 130.13, 129.71, 128.02, 127.80, 127.14, 125.34, 122.29, 121.60, 118.96, 112.81, 66.28, 46.05, 32.65, 13.32.

(Z)-3-(4-((5-(4-Chloro-3-(((tetrahydro-2H-pyran-4-yl)methyl)carbamoyl)phenyl)furan-2-yl)methylene)-3-methyl-5-oxo-4,5-dihydro-1H-pyrazol-1-yl)benzoic acid (NG-02-100)

Red solid (66 mg, 70% yield)

Major Z-isomer data: $^1$H NMR (300 MHz, DMSO): δ 13.12 (brs, 1H, COOH), 8.65-8.59 (m, 2H), 8.54 (s, 1H), 8.19 (d, 1H, J=7.77 Hz), 8.01-7.92 (m, 2H), 7.82-7.73 (m, 2H), 7.69-7.65 (m, 1H), 7.60-7.54 (m, 2H), 3.90-3.81 (m, 2H, $CH_2$), 3.28-3.22 (m, 2H, $CH_2$), 3.19-3.13 (m, 2H, $NHCH_2$), 2.70 (s, 0.67H, minor isomer, $CH_3$), 2.34 (s, 2.33H, major isomer, $CH_3$), 1.84-1.72 (m, 1H, CH), 1.69-1.61 (m, 2H, $CH_2$), 1.30-1.14 (m, 2H, $CH_2$); $^{13}$C NMR (75 MHz, DMSO): δ 167.00, 165.75, 161.70, 157.56, 151.18, 150.29, 138.42, 138.18, 131.41, 130.93, 130.54, 129.66, 129.22, 127.47, 127.31, 126.60, 124.98, 121.79, 121.10, 118.45, 112.32, 66.72, 44.78, 34.77, 30.40, 12.80.

Example 6

General Reduction Method for Target Compounds

Synthesis of NG-01-72.

Scheme 8

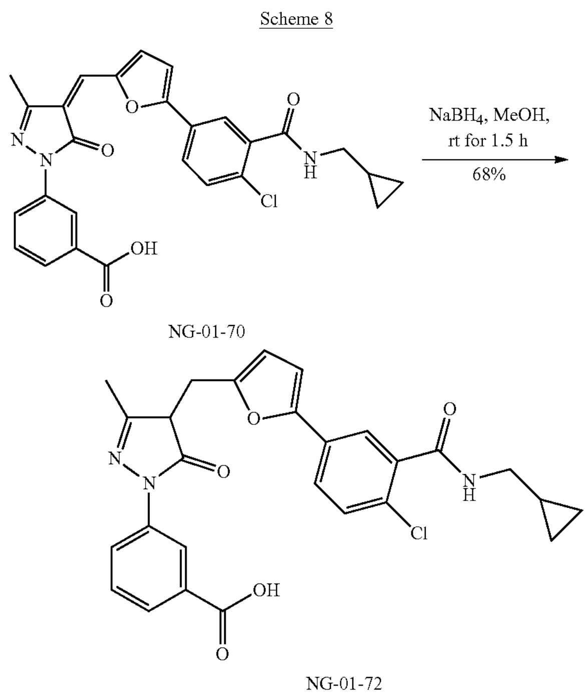

NG-01-70

NG-01-72

3-(4-((5-(4-Chloro-3-((cyclopropylmethyl)carbamoyl)phenyl)furan-2-yl)methyl)-3-methyl-5-oxo-4,5-dihydro-1H-pyrazol-1-yl)benzoic acid (NG-01-72): To a suspension of NG-01-70 (60 mg, 1 equiv.) in anhydrous methanol (5 mL) was added sodium borohydride (13 mg, 3 equiv.) in portions. During addition gas evolution was observed, and the color of the solution changed from dark red to yellowish orange. The resulting solution was stirred at room temperature for 1.5 h. Solvent was removed in vacuo and residue was acidified to pH 2-3 using 20% citric acid solution. The product was extracted with EtOAc (3×15 mL). The combined organic extracts was washed with brine, dried over $Na_2SO_4$ and concentrated under reduced pressure. The product was crystallized in EtOAc, solid was collected, washed with cold EtOAc and then hot solutions of 20-30% EtOAc in hexanes to afford NG-01-72 (41 mg, 68% yield) as a red solid.

Major Z-isomer data: $^1$H NMR (300 MHz, DMSO): δ 13.15 (brs, 1H, COOH), 8.55 (t, 1H, J=5.85 and 11.58 Hz), 8.30 (s, 1H), 7.99 (d, 1H, J=8.22 Hz), 7.78 (d, 2H, J=7.59 Hz), 7.63-7.47 (m, 3H), 6.97 (d, 1H, J=3.3 Hz), 6.33 (d, 1H, J=3.39 Hz), 3.11 (t, 2H, J=6.12 and 12.33 Hz, $NHCH_2$), 2.78-2.62 (q, 1H, CH), 2.34 (brs, 4H), 1.02-0.94 (m, 1H, CH), 0.44-0.38 (m, 2H, $CH_2$), 0.25-0.18 (m, 2H, $CH_2$).

3-(4-((5-(4-Chloro-3-((4-fluorobenzyl)carbamoyl)phenyl)furan-2-yl)methyl)-3-methyl-5-oxo-4,5-dihydro-1H-pyrazol-1-yl)benzoic acid (NG-01-65)

NG-01-65 was prepared from NG-01-64 according to the method described for preparing NG-01-72.

$^1$H NMR (500 MHz, DMSO): δ 8.95 (m, 1H), 8.56 (t, 1H), 8.17 (d, 1H), 8.02-7.95 (m, 2H), 7.73-7.69 (m, 2H), 7.65 (t, 1H), 7.52-7.49 (m, 2H), 7.41-7.38 (m, 2H), 7.17-7.13 (m, 2H), 4.47 (d, 2H, $NHCH_2$), 2.21 (brs, 3H).

Following the same procedure as described for the preparing NG-01-72, the following additional target compounds were prepared using the procedures described above, and starting from the appropriate compound.

Ethyl 3-(4-((5-(4-chloro-3-((3-methoxyphenyl)carbamoyl)phenyl)furan-2-yl)methyl)-3-methyl-5-oxo-4,5-dihydro-1H-pyrazol-1-yl)benzoate (NG-02-131)

MS (ESI) m/z=586.1 $[M+H]^+$ 3-(4-((5-(4-Chloro-3-((3-methoxyphenyl)carbamoyl)phenyl)furan-2-yl)methyl)-3-methyl-5-oxo-4,5-dihydro-1H-pyrazol-1-yl)benzoic acid (NG-02-132)

$^1$H NMR (300 MHz, DMSO): δ 13.12 (brs, 1H, COOH), 10.65.97 (s, 1H, NH), 8.69, 8.68 and 8.55 (m, 1H), 8.32 (s, 1H), 8.23-8.19 (m, 1H), 8.06-8.00 (m, 1H), 7.84-7.74 (m, 3H), 7.65-7.55 (m, 2H), 7.43 (brs, 1H), 7.29-7.27 (t, 2H), 6.75-6.71 (m, 1H), 3.76 (s, 3H), 2.12 (s, 3H).

3-(4-((5-(4-Chloro-3-((3-Methoxyphenyl)carbamoyl)furan-2-yl)methyl)-3-methyl-5-oxo-4,5-dihydro-1H-pyrazol-1-yl)benzoic acid (NG-02-165)

MS (ESI) m/z=446.1 $[M-H]^-$ 4-(4-((5-(4-Chloro-3-((3-methoxyphenyl)carbamoyl)phenyl)furan-2-yl)methyl)-3-methyl-5-oxo-4,5-dihydro-1H-pyrazol-1-yl)benzoic acid (NG-03-188)

$^1$H NMR (300 MHz, DMSO): δ 12.15 (brs, 1H, COOH), 10.67 (s, 1H, NH), 8.22-7.89 (m, 8H), 7.82-7.76 (m, 1H), 7.44 (brs, 1H), 7.30-7.26 (m, 2H), 6.74-6.71 (t, 1H), 3.78 (s, 3H), 2.10 (brs, 3H).

2-chloro-N-(3-Methoxyphenyl)-5-(5-((3-methyl-5-oxo-1-(4-sulfamoylphenyl)-4,5-dihydro-1H-pyrazol-4-yl)methyl)furan-2-yl)benzamide (NG-03-202)

$^1$H NMR (300 MHz, DMSO): δ 10.57 (s, 1H, NH), 7.91-7.80 (m, 5H), 7.73-7.69 (m, 1H), 7.61-7.56 (m, 1H), 7.43-7.36 (m, 2H), 7.28-7.25 (m, 2H), 6.73-6.69 (m, 1H), 3.76 (s, 3H), 2.17 (s, 3H).

5-(5-((1-(3-(1H-Tetrazol-5-yl)phenyl)-3-methyl-5-oxo-4,5-dihydro-1H-pyrazol-4-yl)methyl)furan-2-yl)-2-chloro-N-(3-methoxyphenyl)benzamide (NG-03-205)

$^1$H NMR (300 MHz, DMSO): δ 10.62 (s, 1H, NH), 8.32 (s, 1H), 8.21-8.17 (m, 2H), 8.08-8.02 (s, 1H), 7.8s-7.77 (m, 2H), 7.69-7.65 (m, 3H), 7.53-7.44 (m, 1H), 7.29-7.26 (brs, 2H), 6.74-6.70 (brs, 1H), 3.75 (s, 3H), 1.98 (s, 3H).

3-(4-((5-(4-Chloro-3-((3,4-dimethoxyphenyl)carbamoyl)phenyl)furan-2-yl)methyl)-3-methyl-5-oxo-4,5-dihydro-1H-pyrazol-1-yl)benzoic acid (NG-03-206)

$^1$H NMR (300 MHz, DMSO): δ 10.43 (s, 1H, NH), 8.33-8.31 (m, 1H), 8.05-7.98 (m, 1H), 8.82-7.74 (m, 2H), 7.59-7.55 (m, 2H), 7.44-7.40 (m, 2H), 7.27-7.21 (m, 2H), 6.97-6.91 (m, 2H), 3.76 (s, 6H), 2.17 (s, 3H).

3-(4-((5-(4-chloro-3-((3-Methoxyphenyl)carbamoyl)phenyl)thiophen-2-yl)methyl)-3-methyl-5-oxo-4,5-dihydro-1H-pyrazol-1-yl)benzoic acid (NG-03-207)

$^1$H NMR (300 MHz, DMSO): δ 10.51 (s, 1H, NH), 8.33-8.30 (m, 1H), 8.04-7.98 (m, 1H), 8.77-7.73 (m, 2H), 7.66-7.64 (m, 1H), 7.56-7.51 (m, 3H), 7.45-7.39 (m, 2H), 7.26-7.23 (m, 2H), 6.72-6.69 (m, 1H), 3.74 (s, 3H), 2.15 (s, 3H).

3-(4-((5-(4-Chloro-3-((cyclopropylmethyl)carbamoyl)phenyl)thiophen-2-yl)methyl)-3-methyl-5-oxo-4,5-dihydro-1H-pyrazol-1-yl)benzoic acid (NG-03-231)

MS (ESI) m/z=520.1 $[M-H]^-$ 4-(4-((5-(4-Chloro-3-((3-methoxyphenyl)carbamoyl)phenyl)thiophen-2-yl)methyl)-3-methyl-5-oxo-4,5-dihydro-1H-pyrazol-1-yl)benzoic acid (NG-03-238)

$^1$H NMR (300 MHz, DMSO): δ 12.88 (brs, 1H, COOH), 10.53 (brs, 1H, NH), 8.03-7.98 (m, 2H), 7.95-7.89 (t, 2H), 7.76 (s, 1H), 7.68-7.64 (m, 1H), 7.54-7.51 (d, 1H), 7.47-7.46 (dd, 1H), 7.41 (brs, 1H), 7.26-7.21 (m, 2H), 6.91-6.90 (d, 1H), 6.71-6.67 (m, 1H), 3.74 (s, 3H), 2.17 (s, 3H).

Example 7

Synthesis of NG-01-77

Scheme 9

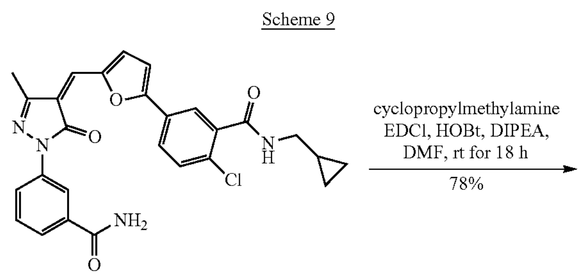

-continued

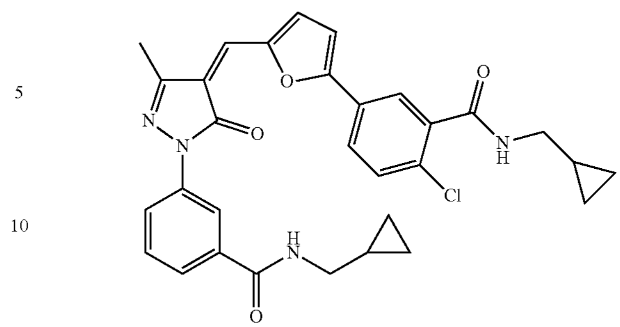

(Z)-2-Chloro-N-(cyclopropylmethyl)-5-(5-((1-(3-((cyclopropylmethyl)carbamoyl)phenyl)-3-methyl-5-oxo-1H-pyrazol-4(5H)-ylidene)methyl)furan-2-yl)benzamide (NG-01-77)

NG-01-77 was synthesized using synthetic procedure described for the preparation of compound 10 using NG-01-70 as a starting material. Product was crystallized in EtOH, solid was collected, washed with EtOAc and then hot solutions of 20-30% EtOAc in hexanes to afford NG-01-77 as a red solid (51 mg, 78% yield). TLC: 4% MeOH in DCM, $R_f$=0.42 visualized with UV.

Major Z-isomer data: $^1$H NMR (300 MHz, DMSO): δ 8.70-8.65 (m, 3H), 8.36 (s, 1H), 8.11 (d, 1H, J=7.83 Hz), 7.99-7.91 (m, 2H), 7.77 (s, 1H), 7.68-7.65 (m, 2H), 7.58 (d, 1H, J=3.9 Hz), 7.54-7.48 (m, 1H), 3.19-3.13 (q, 4H, $2NHCH_2$), 2.72 (s, 0.56H, minor isomer, $CH_3$), 2.34 (s, 2.44H, major isomer, $CH_3$), 1.07-0.95 (m, 2H, 2CH), 0.49-0.41 (m, 4H, $2CH_2$), 0.27-0.23 (m, 4H, $2CH_2$); $^{13}$C NMR (75 MHz, DMSO): δ 166.30, 166.01, 162.14, 159.49, 158.05, 151.50, 150.80, 138.76, 138.61, 136.01, 131.51, 131.23, 131.07, 130.05, 129.23, 127.91, 127.78, 125.41, 123.34, 121.66, 120.89, 117.69, 112.76, 44.08, 43.71 13.31, 11.49, 11.16, 3.73 (t).

Example 8

General Synthesis of NG-02-104, NG-02-105, NG-02-112 and NG-02-113

Scheme 10

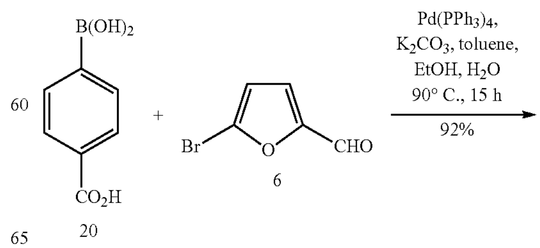

20

6

-continued

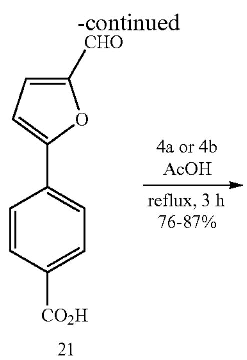

21

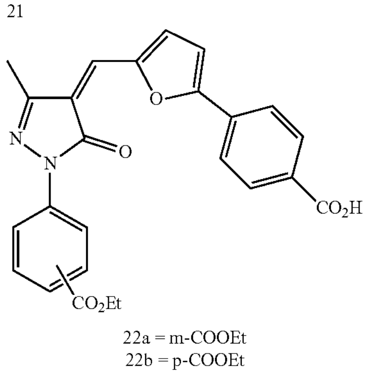

22a = m-COOEt
22b = p-COOEt

Step 1: Synthesis of 4-(5-Formylfuran-2-yl)benzoic acid (21)

A solution of $K_2CO_3$ (2.37 gm, 3 equiv.) in water (10 mL) was added to a mixture of 4-carboxyphenylboronic acid 20 (1.14 gm, 1.2 equiv.) and 5-bromo-2-furaldehyde 6 (1 gm, 1 equiv.) in toluene/ethanol (60 mL). The mixture was degassed with argon for 5 minute and then $Pd(PPh_3)_4$ (330 mg, 0.05 equiv.) was added. The reaction mixture was stirred at 90° C. for 15 h. The reaction mixture was cooled to room temperature and solvent was removed under reduced pressure. The product was washed successively with water (3×15 mL), EtOAc (2×10 mL), DCM and dried under high vacuum overnight to get 4-(5-formylfuran-2-yl)benzoic acid 21 (1.11 gm, 90% yield) as a white solid.

Major Z-isomer data: $^1H$ NMR (500 MHz, DMSO): δ 13.16 (s, 1H, COOH), 9.66 (s, 1H, CHO), 8.05 (dd, 2H, J=1.5 and 6.5 Hz), 8.00 (dd, 2H, J=2.0 and 7.0 Hz), 7.70 (d, 1H, J=3.5 Hz), 7.46 (d, 1H, J=4.0 Hz); $^{13}C$ NMR (125 MHz, DMSO): δ 178.70, 167.17, 157.36, 152.66, 132.78, 131.73, 130.61, 125.47, 111.05.

Step 2: Synthesis of 22a and 22b 22a and 22b were prepared using synthetic procedure described for the preparation of compound 8a using 4-(5-formylfuran-2-yl)benzoic acid 21, 4a (600 mg) and 4b (600 mg) as starting materials.

Step 2a: (Z)-4-(5-((1-(3-(Ethoxycarbonyl)phenyl)-3-methyl-5-oxo-1H-pyrazol-4(5H)-ylidene)methyl)furan-2-yl)benzoic acid (22a)

Red solid (844 mg, 78% yield).

Major Z-isomer data: $^1H$ NMR (500 MHz, DMSO): δ 13.14 (s, 1H, COOH), 8.63 (d, 1H, J=3.5 Hz); 8.49 (t, 1H, J=1.5 and 3.5 Hz), 8.20 (d, 1H, J=8.5 Hz), 8.03-7.90 (m, 4H), 7.76-7.71 (m, 1H), 7.65 (s, 1H), 7.56-7.51 (m, 2H), 4.35-4.29 (q, 2H, $OCH_2$), 2.67 (s, 0.68H, minor isomer, $CH_3$), 2.32 (s, 2.32H, major isomer, $CH_3$), 1.34 (t, 3H, J=7.5 and 14.5 Hz, $CH_3$); $^{13}C$ NMR (125 MHz, DMSO): δ 166.62, 165.40, 161.60, 158.05, 151.10, 150.51, 138.48, 133.15, 131.98, 131.25, 130.09, 129.45, 129.29, 127.32, 124.91, 124.70, 121.27, 118.02, 112.91, 60.88, 14.15, 12.78.

Step 2b: (Z)-4-(5-((1-(4-(Ethoxycarbonyl)phenyl)-3-methyl-5-oxo-1H-pyrazol-4(5H)-ylidene)methyl)furan-2-yl)benzoic acid (22b)

Red solid (920 mg, 85% yield).

Major Z-isomer data: $^1H$ NMR (300 MHz, DMSO): δ 13.08 (brs, 1H, COOH), 8.56 (s, 1H), 7.98-7.81 (m, 7H), 7.62-7.39 (m, 3H), 4.27-4.20 (q, 2H, $OCH_2$), 2.59 (s, 0.68H, minor isomer, $CH_3$), 2.28 (s, 2.32H, major isomer, $CH_3$), 1.28 (t, 3H, J=6.63 and 12.57 Hz, $CH_3$).

Example 9

Synthesis of Amides 23-26

Compounds 23-24 and 25-26 were prepared using synthetic procedure described for the preparation of compound 10 using 22a (300 mg) and 22b (300 mg) as a starting material, respectively.

(Z)-Ethyl 3-(4-((5-(4-((cyclopropylmethyl)carbamoyl)phenyl)furan-2-yl)methylene)-3-methyl-5-oxo-4,5-dihydro-1H-pyrazol-1-yl)benzoate (23)

Red solid (248 mg, 74% yield).

Major Z-isomer data: $^1H$ NMR (300 MHz, DMSO): δ 8.71-8.64 (m, 2H), 8.52 (t, 1H, J=1.8 and 3.6 Hz), 8.21 (d, 1H, J=8.22 Hz), 8.03-7.91 (m, 4H), 7.78-7.70 (m, 2H), 7.59-7.50 (m, 2H), 4.37-4.28 (q, 2H, $OCH_2$), 3.16 (t, 2H, J=6.21 and 12.36 Hz, $NHCH_2$), 2.70 (s, 0.71H, minor isomer, $CH_3$), 2.34 (s, 2.29H, major isomer, $CH_3$), 1.36-1.30 (m, 3H, $CH_3$), 1.08-0.98 (m, 1H, CH), 0.47-0.41 (m, 2H, $CH_2$), 0.26-0.21 (m, 2H, $CH_2$); $^{13}C$ NMR (75 MHz, DMSO): δ 165.91, 165.64, 165.01, 162.18, 159.00, 151.69, 150.82, 139.02, 138.84, 135.64, 131.01, 130.97, 130.09, 129.83, 128.56, 128.04, 127.00, 125.25, 122.53, 121.43, 118.53, 112.96, 61.40, 44.11, 14.66, 13.31, 11.46, 3.83.

(Z)-Ethyl 3-(4-((5-(4-((4-fluorobenzyl)carbamoyl)phenyl)furan-2-yl)methylene)-3-methyl-5-oxo-4,5-dihydro-1H-pyrazol-1-yl)benzoate (24)

Red solid (294 mg, 79% yield).

Major Z-isomer data: $^1H$ NMR (300 MHz, DMSO): δ 9.29 (t, 1H, J=5.7 and 11.7 Hz), 8.64 (d, 1H, J=3.72 Hz), 8.56-8.47 (m, 1H), 8.21 (d, 1H, J=8.1 Hz), 8.06-7.86 (m, 4H), 7.76-7.61 (m, 2H), 7.57-7.44 (m, 2H), 7.42-7.32 (m, 2H), 7.20-7.12 (m, 2H), 4.45 (d, 2H, J=5.67 Hz, $NHCH_2$), 4.36-4.27 (q, 2H, $OCH_2$), 2.67 (s, 0.49H, minor isomer, $CH_3$), 2.32 (s, 2.51H, major isomer, $CH_3$), 1.35-1.29 (m, 3H, $CH_3$); $^{13}C$ NMR (75 MHz, DMSO): δ 166.59, 166.05, 162.49, 159.25, 158.43, 151.15, 150.67, 147.18, 139.31, 136.55, 135.55, 132.60, 131.50, 131.28, 130.89, 130.04, 129.94, 129.01, 128.69, 128.34, 125.75, 125.61, 122.86, 121.76, 119.92, 118.85, 115.84, 115.75, 113.36, 61.70 (d), 42.74, 14.99, 13.76 (d).

(Z)-Ethyl 4-(4-((5-(4-((cyclopropylmethyl)carbamoyl)phenyl)furan-2-yl)methylene)-3-methyl-5-oxo-4,5-dihydro-1H-pyrazol-1-yl)benzoate (25)

Red solid (251 mg, 75% yield).

Major Z-isomer data: $^1$H NMR (300 MHz, DMSO): δ 8.69 (t, 1H, J=5.58 and 11.55 Hz), 8.63 (d, 1H, J=3.66 Hz), 8.09-7.90 (m, 8H), 7.70 (s, 1H), 7.56-7.50 (m, 1H), 4.31-4.22 (q, 2H, $OCH_2$), 3.15 (t, 2H, J=5.7 and 12.0 Hz, $NHCH_2$), 2.68 (s, 0.70H, minor isomer, $CH_3$), 2.33 (s, 2.30H, major isomer, $CH_3$), 1.33-127 (m, 3H, $CH_3$), 1.08-0.99 (m, 1H, CH), 0.47-0.41 (m, 2H, $CH_2$), 0.26-0.21 (m, 2H, $CH_2$).

(Z)-Ethyl 4-(4-((5-(4-((4-fluorobenzyl)carbamoyl)phenyl)furan-2-yl)methylene)-3-methyl-5-oxo-4,5-dihydro-1H-pyrazol-1-yl)benzoate (26)

Red solid (297 mg, 80% yield).

Major Z-isomer data: $^1$H NMR (300 MHz, DMSO): δ 9.20 (m, 1H), 8.64 (d, 1H, J=3.84 Hz), 8.11-7.92 (m, 8H), 7.73 (d, 1H, J=11.7 Hz), 7.58-7.49 (m, 1H), 7.40-7.31 (m, 2H), 7.19-7.09 (m, 2H), 4.48-4.42 (q, 2H, $NHCH_2$), 4.32-4.21 (m, 2H, $OCH_2$), 2.66 (s, 0.56H, minor isomer, $CH_3$), 2.34 (s, 2.44H, major isomer, $CH_3$), 1.33-1.25 (m, 3H, $CH_3$).

Example 10

Preparation of compounds NG-02-104, NG-02-105, NG-02-112 and NG-02-113

Compounds NG-02-104, NG-02-105, NG-02-112 and NG-02-113 were prepared using synthetic procedure described for the preparation of compound NG-01-64 using appropriate starting materials. Each compound was crystallized in EtOH, solid was collected, washed with EtOAc and then hot solutions of 20-30% EtOAc in hexanes to afford desired final compound.

(Z)-3-(4-((5-(4-((Cyclopropylmethyl)carbamoyl)phenyl)furan-2-yl)methylene)-3-methyl-5-oxo-4,5-dihydro-1H-pyrazol-1-yl)benzoic acid (NG-02-104)

Red solid (90 mg, 64% yield)

Isomer data: $^1$H NMR (300 MHz, DMSO): δ 13.11 (s, 1H, COOH), 8.72-8.65 (m, 2H), 8.55 (d, 1H, J=14.52 Hz), 8.19 (d, 1H, J=6.15 Hz), 8.05-7.92 (m, 4H), 7.82-7.70 (m, 2H), 7.59-7.51 (m, 2H), 3.16 (t, 2H, J=6.35 and 12.28 Hz, $NHCH_2$), 2.73 (s, 1.65H, $CH_3$), 2.34 (s, 1.35H, $CH_3$), 1.09-0.97 (m, 1H, CH), 0.48-0.40 (m, 2H, $CH_2$), 0.27-0.20 (m, 2H, $CH_2$); $^{13}$C NMR (75 MHz, DMSO): δ 167.07, 165.22, 161.75, 159.93, 158.54, 151.20, 150.41, 138.49, 138.33, 135.20, 131.45, 130.77, 130.60, 129.65, 129.25, 128.14, 127.56, 124.99, 124.82, 121.82, 121.09, 118.48, 112.52, 112.29, 43.67, 12.87, 11.02, 3.39.

(Z)-3-(4-((5-(4-((4-Fluorobenzyl)carbamoyl)phenyl)furan-2-yl)methylene)-3-methyl-5-oxo-4,5-dihydro-1H-pyrazol-1-yl)benzoic acid (NG-02-105)

Red solid (103 mg, 73% yield)

Major Z-isomer data: $^1$H NMR (300 MHz, DMSO): δ 13.12 (s, 1H, COOH), 9.20-9.16 (m, 1H), 8.69 (d, 1H, J=3.84 Hz), 8.55 (t, 1H, J=1.83 and 3.6 Hz, major isomer), 8.21 (d, 1H, J=8.16 Hz), 8.08-7.98 (m, 4H), 7.83-7.73 (m, 2H), 7.60-7.53 (m, 2H), 7.40-7.35 (m, 2H), 7.16 (t, 2H, J=8.94 and 17.82 Hz), 4.48 (d, 2H, J=5.79 Hz, $NHCH_2$), 2.75 (s, 1.06H, minor isomer, $CH_3$), 2.35 (s, 1.94H, major isomer, $CH_3$); $^{13}$C NMR (75 MHz, DMSO): δ 167.03, 165.34, 162.76, 161.74, 159.56, 158.43, 149.97, 148.23, 138.46, 135.68, 134.79, 131.44, 130.79, 129.32, 129.22, 128.19, 127.51, 125.04, 124.87, 121.82, 121.13, 119.46, 118.47, 115.15, 114.87, 112.60, 42.01, 12.84.

(Z)-4-(4-((5-(4-((Cyclopropylmethyl)carbamoyl)phenyl)furan-2-yl)methylene)-3-methyl-5-oxo-4,5-dihydro-1H-pyrazol-1-yl)benzoic acid (NG-02-112)

Red solid (94 mg, 67% yield)

Major Z-isomer data: $^1$H NMR (300 MHz, DMSO): δ 12.82 (s, 1H, COOH), 8.70-8.64 (m, 2H,), 8.09-7.79 (m, 8H), 7.73 (s, 1H), 7.57-7.53 (m, 1H), 3.15 (t, 2H, J=6.0 and 12.0 Hz, $NHCH_2$), 2.72 (s, 0.45H, minor isomer, $CH_3$), 2.33 (s, 2.55H, major isomer, $CH_3$), 1.09-0.97 (m, 1H, CH), 0.46-0.40 (m, 2H, $CH_2$), 0.26-0.21 (m, 2H, $CH_2$); $^{13}$C NMR (75 MHz, DMSO): δ 166.76, 165.09, 161.86, 158.55, 151.59, 150.27, 141.65, 135.21, 130.85, 130.44, 128.03, 125.87, 124.73, 120.71, 116.86, 112.45, 43.56, 12.79, 10.90, 3.27.

(Z)-4-(4-((5-(4-((4-Fluorobenzyl)carbamoyl)phenyl)furan-2-yl)methylene)-3-methyl-5-oxo-4,5-dihydro-1H-pyrazol-1-yl)benzoic acid (NG-02-113)

Red solid (109 mg, 77% yield)

Major Z-isomer data: $^1$H NMR (300 MHz, DMSO): δ 12.82 (s, 1H, COOH), 9.18 (t, 1H, J=5.7 and 11.64 Hz), 8.65 (d, 1H, J=3.45 Hz), 8.10-7.94 (m, 8H), 7.74 (s, 1H), 7.59-7.54 (m, 1H), 7.40-7.32 (m, 2H), 7.16 (t, 2H, J=8.85 and 17.67 Hz), 4.48 (d, 2H, J=5.55, $NHCH_2$), 2.73 (s, 0.64H, minor isomer, $CH_3$), 2.34 (s, 2.36H, major isomer, $CH_3$); $^{13}$C NMR (75 MHz, DMSO): δ 166.65, 165.14, 161.76, 158.36, 151.51, 150.21, 141.54, 135.53, 135.49, 130.56, 130.26, 129.14, 129.03, 128.00, 125.78, 124.70, 120.68, 116.77, 114.97, 114.68, 112.44, 41.83, 12.69.

Example 11

Preparation of (Z)-3-(4-((5-((3-methoxyphenyecarbamoyl)furan-2-yl)methylene)-3-methyl-5-oxo-4,5-dihydro-1H-pyrazol-1-yl)benzoic acid (NG-02-162)

NG-02-162 was made according to the procedure described in Example 1, except that 3-methoxyphenylboronic acid was used in place of 4-chloro-3-carboxyphenylboronic acid. $^1$H NMR (300 MHz, DMSO): δ 9.97 (brs, 1H, NH), 8.35 (s, 1H), 8.04-8.02 (s, 1H), 7.77-7.74 (m, 1H), 7.60-7.54 (t, 1H), 7.37-7.21 (m, 5H), 6.66-6.64 (m, 1H), 3.72 (s, 3H), 2.33 (s, 2.37H; major isomer, $CH_3$).

Example 12

Preparation of Additional Target Compounds

Addition target compounds were prepared according to the procedures shown in Examples 4 and 5 using appropriate starting materials.

(Z)-4-(4-((5-(4-Chloro-3-((3-methoxyphenyl)carbamoyl)phenyl)furan-2-yl)methylene)-3-methyl-5-oxo-4,5-dihydro-1H-pyrazol-1-yl)benzoic acid (NG-03-185)

Major Z-isomer data: $^1$H NMR (300 MHz, DMSO): δ 12.91 (brs, 1H, COOH), 10.55 (s, 1H, NH), 8.62 (brs, 1H), 8.10-7.87 (m, 7H), 7.81-7.78 (m, 1H), 7.70-7.68 (m, 1H), 7.60- 7.56 (m, 1H), 7.45-7.41 (m, 1H), 7.28-7.24 (m, 2H), 6.72-6.69 (m, 1H). 3.74 (s, 3H), 2.74 (s, 0.22H; minor isomer, $CH_3$), 2.35 (s, 2.84H; major isomer, $CH_3$).

(Z)-3-(4-((5-(4-chloro-3-((3,4-dimethoxyphenyl) carbamoyl)phenyl)furan-2-yl)methylene)-3-methyl-5-oxo-4,5-dihydro-1H-pyrazol-1-yl)benzoic acid (NG-03-189)

Red solid (60 mg, 63% yield).

Major Z-isomer data: $^1$H NMR (300 MHz, DMSO): δ 13.14 (brs, 1H, COOH), 10.52 (s, 1H, NH), 8.70 (d, 1H, J=3.75 Hz), 8.56-8.51 (m, 1H), 8.28-8.18 (m, 2H), 8.08-8.04 (m, 1H), 7.80-7.74 (m, 3H), 7.65-7.55 (m, 2H), 7.45 (m, 1H), 7.30-7.27 (m, 2H), 6.97-6.90 (m, 1H), 3.75 and 3.74 (s, 3H, $OCH_3$), 2.74 (s, 0.49H; minor isomer, $CH_3$), 2.35 (s, 2.49H; major isomer, $CH_3$); $^{13}$C NMR (75 MHz, DMSO): δ 167.51, 164.22, 164.69, 162.22, 157.99, 151.70, 150.84, 149.00, 145.79, 138.93, 138.37, 131.93, 131.58, 130.46, 129.74, 127.94, 127.39, 125.73, 125.43, 122.30, 121.71, 118.96, 112.44, 111.98, 104.97, 105.83, 56.17, 55.84, 13.30. MS (ESI) m/z=584.1 [M−H]$^-$; HRMS (ESI): calcd for $C_{31}H_{23}N_3O_7Cl$ [M−H]$^-$ m/z=584.1225, found 584.1236. HPLC purity: 95.07%.

(Z)-2-chloro-5-(5-((1-(3-cyanophenyl)-3-methyl-5-oxo-1,5-dihydro-4H-pyrazol-4-ylidene)methyl) furan-2-yl)-N-(3-methoxyphenyl)benzamide (NG-03-193)

Major Z-isomer data: $^1$H NMR (300 MHz, DMSO): δ 10.65 (s, 1H, NH), 8.62 (brs, 1H), 8.30-8.16 (m, 2H), 7.74 (s, 1H), 7.31-7.25 (m, 2H), 6.72 (brs, 1H), 3.72 (s, 3H), 2.77 (s, 0.92H; minor isomer, $CH_3$), 2.32 (s, 2.08H; major isomer, $CH_3$).

(Z)-2-chloro-N-(3-methoxyphenyl)-5-(5-((3-methyl-5-oxo-1-(4-sulfamoylphenyl)-1,5-dihydro-4H-pyrazol-4-ylidene)methyl)furan-2-yl)benzamide (NG-03-196)

Major Z-isomer data: $^1$H NMR (300 MHz, DMSO): δ 10.66 (s, 1H, NH), 8.64-8.63 (s, 1H), 8.15-8.10 (m, 2H), 7.87-7.78 (m, 4H), 7.66-7.65 (d, 1H), 7.43 (s, 1H), 7.34 (s, 2H), 7.29-7.28 (d, 2H), 6.75-6.71 (m, 1H), 3.76 (s, 3H), 2.74 (s, 0.42H; minor isomer, $CH_3$), 2.35 (s, 2.60H; major isomer, $CH_3$).

(Z)-3-(4-((5-(4-chloro-3-((3-methoxyphenyl)carbamoyl)phenyl)thiophen-2-yl)methylene)-3-methyl-5-oxo-4,5-dihydro-1H-pyrazol-1-yl)benzoic acid (NG-03-203)

100% Z-isomer data: $^1$H NMR (300 MHz, DMSO): δ 10.63 (s, 1H, NH), 8.58 (t, 1H), 8.19-8.15 (m, 3H), 8.07-8.06 (d, 1H), 7.97-7.92 (m, 2H), 7.66-7.66 (dd, 2H), 7.58-7.53 (t, 1H), 7.44-7.43 (m, 1H), 7.29-7.27 (m, 2H), 6.74-6.70 (m, 1H), 3.75 (s, 3H), 2.34 (s, 3H); $^{13}$C NMR (75 MHz, DMSO): δ 168.61, 165.75, 163.60, 161.04, 154.90, 152.92, 146.05, 141.45, 139.91, 139.76, 139.21, 137.74, 133.33, 132.93, 132.34, 131.19, 130.86, 130.04, 127.75, 126.55, 123.25, 122.33, 119.76, 113.46, 110.99, 106.93, 56.56, 14.37.

(Z)-2-chloro-N-(cyclopropylmethyl)-5-(5-((3-methyl-5-oxo-1-(4-sulfamoylphenyl)-1,5-dihydro-4H-pyrazol-4-ylidene)methyl)furan-2-yl)benzamide (NG-03-212)

Major Z-isomer data: $^1$H NMR (300 MHz, DMSO): δ 8.71 (t, 1H), 8.63 and 8.62 (d, 1H), 8.16-8.10 (m, 2H), 8.03-8.01 (m, 2H), 7.90-7.82 (m, 3H), 7.70-7.67 (m, 1H), 7.63-7.59 (m, 1H), 7.34 (s, 2H, $SO_2NH_2$), 3.19-3.15 (t, 2H, $NHCH_2$), 2.74 (s, 0.52H; minor isomer, $CH_3$), 2.36 (s, 2.59H; major isomer, $CH_3$), 1.05-0.1 (m, 1H), 0.49-0.43 (m, 2H, $CH_2$), 0.28-0.25 (m, 2H, $CH_2$).

(Z)-2-chloro-N-(4-fluorobenzyl)-5-(5-((3-methyl-5-oxo-1-(4-sulfamoylphenyl)-1,5-dihydro-4H-pyrazol-4-ylidene)methyl)furan-2-yl)benzamide (NG-03-213)

Major Z-isomer data: $^1$H NMR (300 MHz, DMSO): δ 9.16 (t, 1H), 8.66 and 8.65 (d, 1H), 8.16-8.12 (m, 2H), 8.04-7.99 (m, 2H), 7.72-7.60 (m, 2H), 7.44-7.41 (m, 2H), 7.34 (s, 2H, $SO_2NH_2$), 7.23-7.16 (m, 4H), 4.49-4.47 (d, 2H), 2.68 (s, 0.55H; minor isomer, $CH_3$), 2.36 (s, 2.43H; major isomer, $CH_3$).

(Z)-5-(5-((1-(3-Carboxyphenyl)-3-methyl-5-oxo-1,5-dihydro-4H-pyrazol-4-ylidene)methyl)thiophen-2-yl)-2-chlorobenzoic acid (NG-03-224)

100% Z-isomer data: $^1$H NMR (300 MHz, DMSO): δ 14.15 (brs, 1H, COOH), 13.29 (brs, 1H, COOH), 8.33 (brs, 1H), 8.04-8.01 (d, 2H), 7.91-7.89 (m. 1H), 7.82-7.69 (m, 2H), 7.60-7.42 (m, 3H), 6.79 (brs, 1H), 2.36 (s, 3H, major isomer, $CH_3$).

(Z)-3-(4-((5-(4-Chloro-3-((cyclopropylmethyl)carbamoyl)phenyl)thiophen-2-yl)methylene)-3-methyl-5-oxo-4,5-dihydro-1H-pyrazol-1-yl)benzoic acid (NG-03-226)

100% Z-isomer data: $^1$H NMR (300 MHz, DMSO): δ 13.11 (brs, 1H, COOH), 8.63-8.54 (m, 1H), 8.39 (brs, 1H), 8.09-8.06 (d, 1H), 7.80-7.72 (m, 2H), 7.64-7.37 (m, 5H), 6.76-6.75 (brs, 1H), 3.16-3.09 (m, 2H, $NHCH_2$), 2.31 (s, 3H, major isomer, $CH_3$), 1.04-0.96 (m, 1H, CH), 0.45-0.40 (m, 2H, $CH_2$), 0.24-0.20 (m, 2H, $CH_2$).

(Z)-3-(4-((5-(4-Chloro-3-((4-fluorobenzyl)carbamoyl)phenyl)thiophen-2-yl)methylene)-3-methyl-5-oxo-4,5-dihydro-1H-pyrazol-1-yl)benzoic acid (NG-03-227)

100% Z-isomer data: $^1$H NMR (300 MHz, DMSO): δ 13.14 (brs, 1H, COOH), 9.18-9.14 (t, 1H), 8.59 (brs, 1H), 8.23-8.19 (m, 3H), 7.94-7.90 (m, 3H), 7.80-7.75 (d, 1H), 7.65-7.55 (m, 2H), 7.46-7.41 (m, 2H), 7.22-7.16 (t, 2H), 4.49-4.47 (d, 2H, $NHCH_2$), 2.36 (s, 3H, major isomer, $CH_3$).

3-(4-((5-(4-Chloro-3-((4-fluorobenzyl)carbamoyl)phenyl)thiophen-2-yl)methyl)-3-methyl-5-oxo-4,5-dihydro-1H-pyrazol-1-yl)benzoic acid (NG-03-232)

MS (ESI) m/z=574.1 $[M-H]^-$ (Z)-5-(5-((1-(4-Carboxyphenyl)-3-methyl-5-oxo-1,5-dihydro-4H-pyrazol-4-ylidene)methyl)thiophen-2-yl)-2-chlorobenzoic acid (NG-03-234)

100% Z-isomer data: $^1$H NMR (300 MHz, DMSO): δ 14.11 (brs, 1H, COOH), 13.23 (brs, 1H, COOH), 8.20-8.00 (m, 3H), 7.95-7.88 (m, 3H), 7.74-7.70 (m, 1H), 7.53-7.42 (m, 2H), 2.35 (s, 3H, major isomer, $CH_3$).

Ethyl (Z)-4-(4-((5-(4-chloro-3-((3-methoxyphenyl)carbamoyl)phenyl)thiophen-2-yl)methylene)-3-methyl-5-oxo-4,5-dihydro-1H-pyrazol-1-yl)benzoate (NG-03-235)

100% Z-isomer data: $^1$H NMR (300 MHz, DMSO): δ 10.64 (brs, 1H, NH), 8.21-8.16 (m, 2H), 8.16-8.14 (m, 1H), 8.10 (s, 1H), 8.06-8.0 (m, 3H), 7.95-7.90 (m, 2H), 7.71-7.68 (d, 1H), 7.46-7.43 (m, 1H), 7.30-7.24 (m, 2H), 6.74-6.70 (m, 1H), 4.34 (q, 2H), 3.76 (s, 3H), 2.35 (s, 3H, major isomer, $CH_3$), 1.34-1.28 (t, 3H).

(Z)-4-(4-((5-(4-Chloro-3-((3-methoxyphenyl)carbamoyl)phenyl)thiophen-2-yl)methylene)-3-methyl-5-oxo-4,5-dihydro-1H-pyrazol-1-yl)benzoic acid (NG-03-236)

100% Z-isomer data: $^1$H NMR (300 MHz, DMSO): δ 12.87 (brs, 1H, COOH), 10.64 (brs, 1H, NH), 8.21-8.16 (m, 2H), 8.14-7.90 (m, 7H), 7.74-7.68 (d, 1H), 7.46-7.41 (m, 1H), 7.29-7.24 (m, 2H), 6.74-6.70 (m, 1H), 3.76 (s, 3H), 2.35 (s, 3H, major isomer, $CH_3$).

(Z)-3-(4-((5-(3-(Benzylcarbamoyl)-4-chlorophenyl)furan-2-yl)methylene)-3-methyl-5-oxo-4,5-dihydro-1H-pyrazol-1-yl)benzoic acid (NG-03-270)

Major Z-isomer data: $^1$H NMR (300 MHz, DMSO): δ 13.17 (brs, 1H, COOH), 9.07 (t, 1H), 8.33 (brs, 1H), 8.04-8.01 (d, 1H), 7.80-7.25 (m, 12H), 6.99-6.98 (d, 1H), 4.45-4.43 (d, 2H), 2.70 (s, 0.70H; minor isomer, $CH_3$), 2.29 (s, 2.43H; major isomer, $CH_3$).

(Z)-3-(4-((5-(4-chloro-3-((2-chlorobenzyl)carbamoyl)phenyl)furan-2-yl)methylene)-3-methyl-5-oxo-4,5-dihydro-1H-pyrazol-1-yl)benzoic acid (NG-03-271)

Major Z-isomer data: $^1$H NMR (300 MHz, DMSO): δ 13.14 (brs, 1H, COOH), 9.12-9.09 (m, 1H), 8.32 (brs, 1H), 8.03-8.00 (d, 1H), 7.95-7.78 (m, 2H), 7.70-7.30 (m, 9H), 7.06-6.99 (m, 1H), 4.51-4.49 (d, 2H), 2.71 (s, 0.52H; minor isomer, $CH_3$), 2.36 (s, 2.49H; major isomer, $CH_3$).

(Z)-4-(4-((5-(3-(Benzylcarbamoyl)-4-chlorophenyl)furan-2-yl)methylene)-3-methyl-5-oxo-4,5-dihydro-1H-pyrazol-1-yl)benzoic acid (NG-03-280)

Major Z-isomer data: $^1$H NMR (300 MHz, DMSO): δ 12.87 (brs, 1H, COOH), 9.16-9.11 (t, 1H), 8.62 (brs, 1H), 8.10-7.86 (m, 5H), 7.82-7.76 (m, 1H), 7.70-7.67 (d, 1H), 7.67-7.53 (m, 2H), 7.46-7.27 (m, 5H), 4.51-4.49 (d, 2H), 2.66 (s, 1.05H; minor isomer, $CH_3$), 2.34 (s, 1.96H; major isomer, $CH_3$).

(Z)-4-(4-((5-(4-Chloro-3-((3-methoxybenzyl)carbamoyl)phenyl)furan-2-yl)methylene)-3-methyl-5-oxo-4,5-dihydro-1H-pyrazol-1-yl)benzoic acid (NG-04-286)

Major Z-isomer data: $^1$H NMR (300 MHz, DMSO): δ 12.87 (brs, 1H, COOH), 9.16-9.12 (t, 1H), 8.64 and 8.63 (d, 1H), 8.14-7.92 (m, 5H), 7.82-7.78 (m, 1H), 7.71-7.68 (d, 1H), 7.68-7.53 (m, 2H), 7.35-7.24 (m, 1H), 6.97-6.96 (brs, 2H), 6.88-6.82 (m, 1H), 4.49-4.47 (d, 2H), 3.75 (s, 3H), 2.67 (s, 0.77H; minor isomer, $CH_3$), 2.34 (s, 2.26H; major isomer, $CH_3$).

Example 13

Preparation of NG-03-201

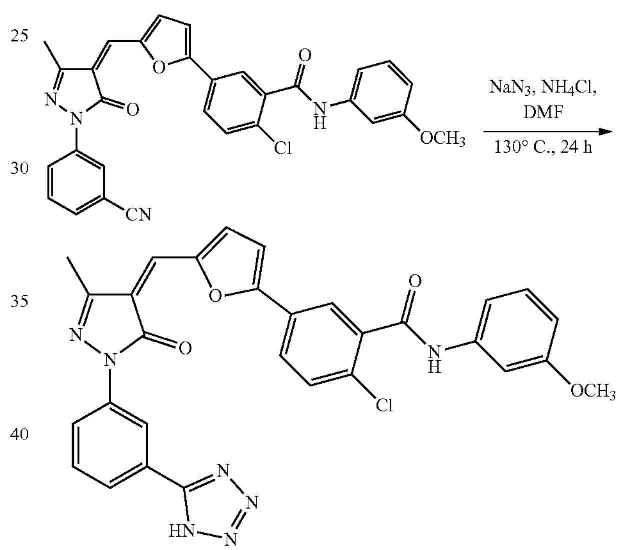

(Z)-5-(5-((1-(3-(1H-Tetrazol-5-yl)phenyl)-3-methyl-5-oxo-1,5-dihydro-4H-pyrazol-4-ylidene)methyl)furan-2-yl)-2-chloro-N-(3-methoxyphenyl)benzamide (NG-03-201)

To a solution of nitrile (NG-03-193) (200 mg, 1 equiv.) in anhydrous DMF (10 mL) was added sodium azide (72 mg, 3 equiv.) and then $NH_4Cl$ (60 mg, 3 equiv.). The reaction mixture was heated at 130° C. for 24 h. After cooling the reaction mixture, it was poured into 50-60 ml cold water and acidified with 1N HCl to pH~2. The precipitated solid was collected by filtration, washed with water. The crude product was crystallized in EtOH/EtOAc mixture (1:9), solid was collected, washed with EtOAc and then hot solutions of 20-30% EtOAc in hexanes to afford tetrazole NG-03-201 (138 mg, 64% yield) as a red solid.

Major Z-isomer data: $^1$H NMR (300 MHz, DMSO): δ 10.66 (s, 1H, NH), 8.64 and 8.62 (d, 1H), 8.32 (s, 1H), 8.28-8.21 (m, 2H), 8.08-8.02 (m, 1H), 7.84 (s, 1H), 7.77-7.74 (d, 1H), 7.65-7.62 (m, 3H), 7.44-7.41 (m, 1H), 7.29-

7.25 (m, 2H), 6.74-6.70 (m, 1H), 3.75 (s, 3H), 2.71 (s, 0.64H; minor isomer, $CH_3$), 2.33 (s, 2.36H; major isomer, $CH_3$).

BIOLOGICAL EXAMPLES

Example 1: Protein Purification and Biochemical Assays

Recombinant human Ku heterodimer was purified from insect cells infected with recombinant baculovirus as previously described (see for example, Lehman, J. et al., Biochemistry, 2008, 47, 4359-68). Ku-DNA binding assays were also performed as previously described (see for example, Lehman, J. et al., Biochemistry, 2008, 47, 4359-68; Pawelczak, K. et al., Nucleic Acids Res., 2005; 33, 152-61; and Pawelczak, K. et al., Nucleic Acids Res., 2008, 36, 4022-31).

Assay Results

Figure 1B:
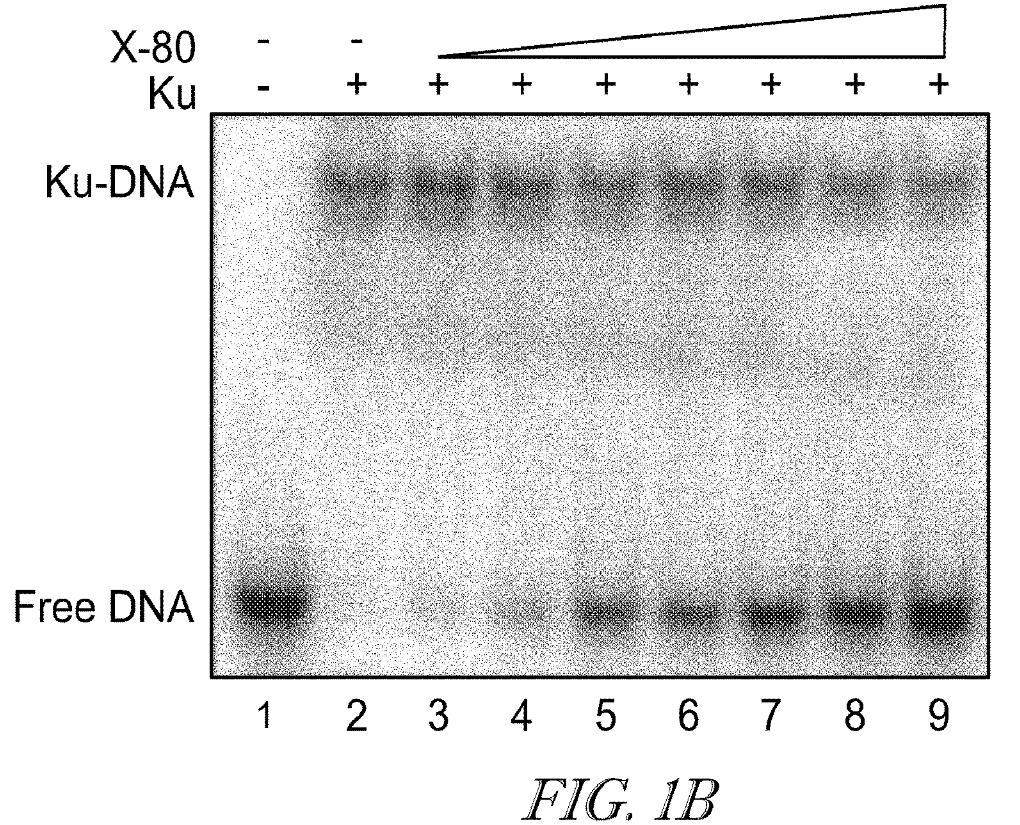

In our analysis of compound specificity, we observed that the X80 class of compounds had robust inhibitory activity against the Ku protein. X80 was titrated into Ku-DNA binding reactions and the results presented in FIGS. 1A and 1B. The DNA binding ability of Ku is reduced in a concentration dependent manner with an $IC_{50}$, (concentration that inhibits 50% of the binding activity) of ~75 μM. Ku is a DNA end-binding protein that is essential for the repair of DNA double strand breaks via the NHEJ pathway. The mechanism of DNA binding by Ku is via a toroid structure that encircles double-stranded DNA from a terminus.

Figures 2A, 2B:
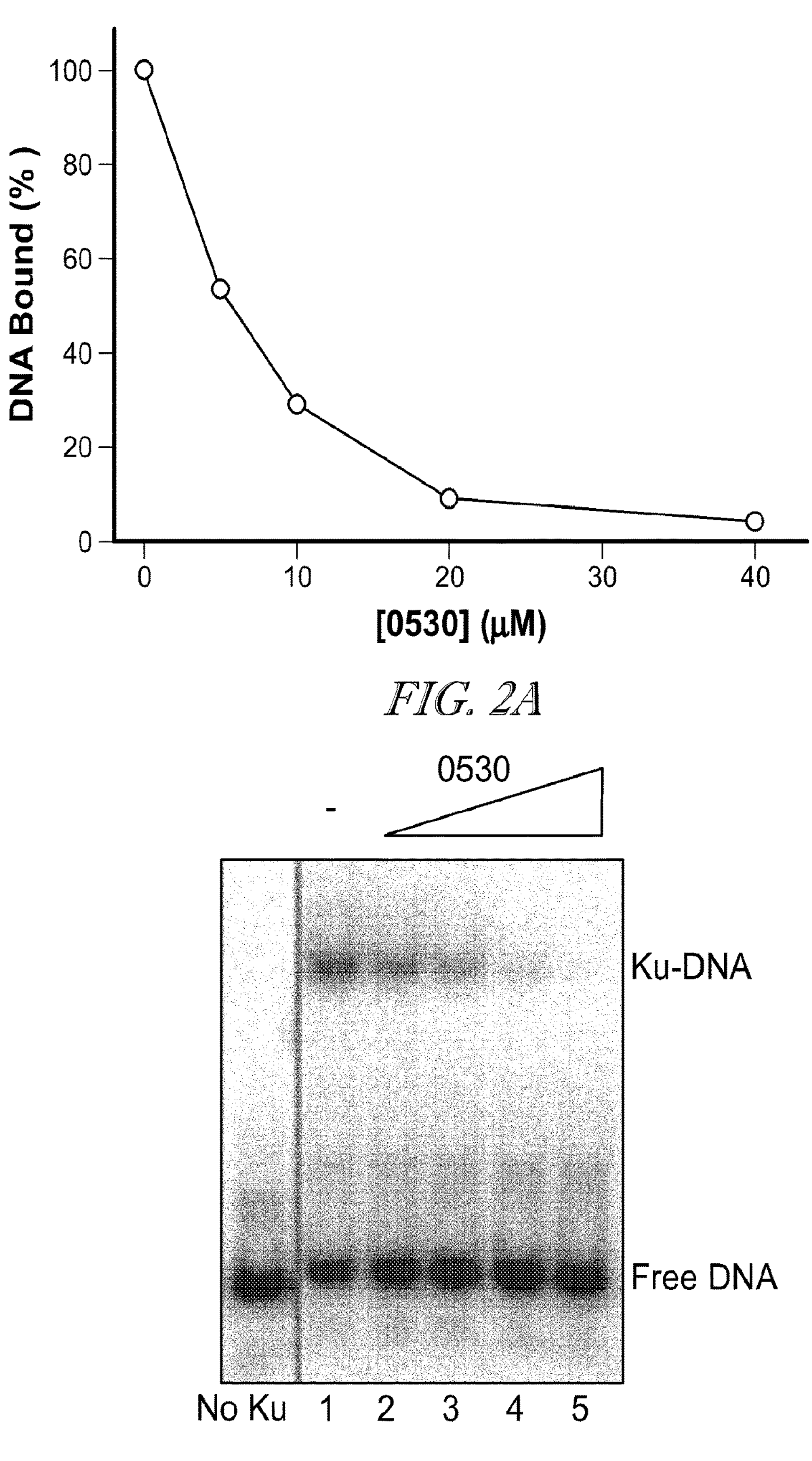
FIG. 2A-2B shows the effect of 0530 on Ku binding DNA with FIG. 2A showing a plot of percentage of DNA bound as a function of 0530 concentration and FIG. 2B showing a DNA gel of Ku-DNA binding as a function of 0530 concentration

A series of commercially available compounds were purchased to pursue the determination of structure activity relationships. A second generation compounds typified by 0530 resulted in considerable greater potency with an $IC_{50}$ of ~5 μM (FIGS. 2A, 2B). The structures and potencies of the second generation inhibitors are presented in Table 1.

TABLE 1

| Name | Structure | $IC_{50}$ (μM) |
| --- | --- | --- |
| X80 | 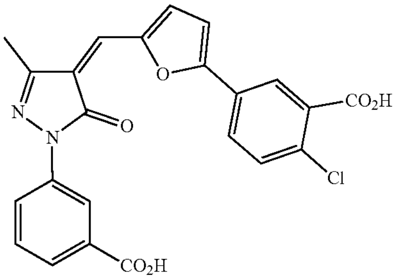<br>$C_{23}H_{15}ClN_2O_6$ | 75 |
| 0814 | 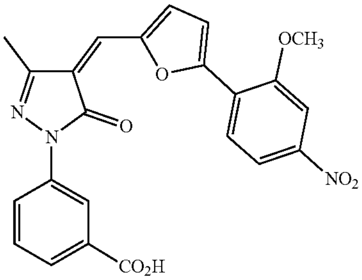<br>$C_{23}H_{17}N_3O_7$ | 190 |
| 0949 | 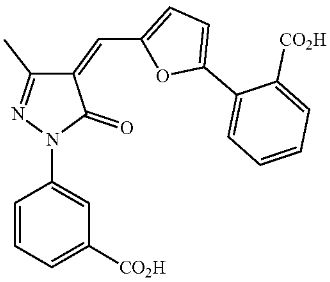<br>$C_{23}H_{16}N_2O_6$ | 91 |

TABLE 1-continued
| Name | Structure | $IC_{50}$ (μM) |
|---|---|---|
| 2513 | 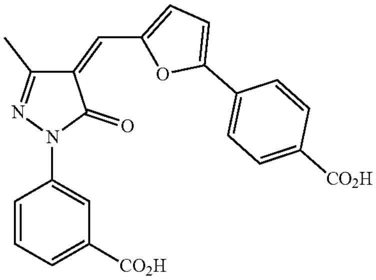 $C_{23}H_{16}N_2O_6$ | 150 |
| 0803 | 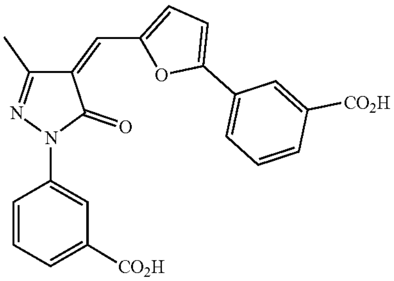 $C_{23}H_{16}N_2O_6$ | 65 |
| 0277 | 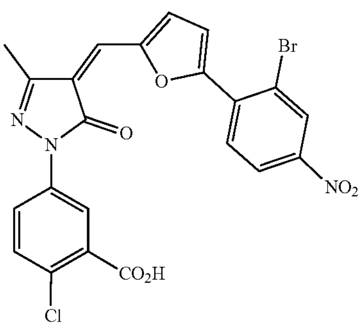 $C_{22}H_{13}BrClN_3O_6$ | 21, 19 |
| 2138 | 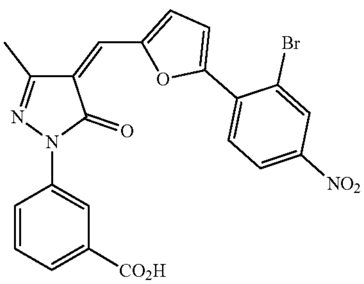 $C_{22}H_{14}BrN_3O_6$ | 17, 9, 12 |

TABLE 1-continued
| Name | Structure | $IC_{50}$ (μM) |
|---|---|---|
| 1564 | 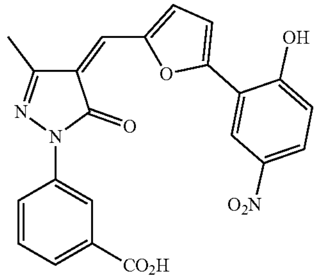 $C_{22}H_{15}N_3O_7$ | 21, 7 |
| 0302 | 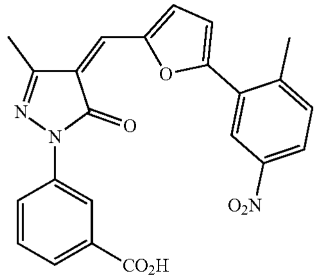 $C_{23}H_{17}N_3O_6$ | 13, 7, 9, |
| 0530 | 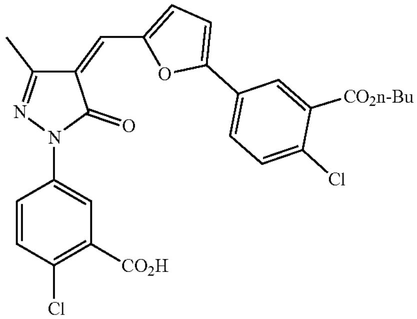 $C_{27}H_{22}Cl_2N_2O_6$ | 5.6 |
| 2714 | 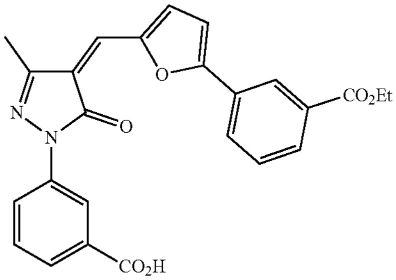 $C_{25}H_{20}N_2O_6$ | 9.1 |

TABLE 1-continued
| Name | Structure | $IC_{50}$ (μM) |
|---|---|---|
| 2727 | 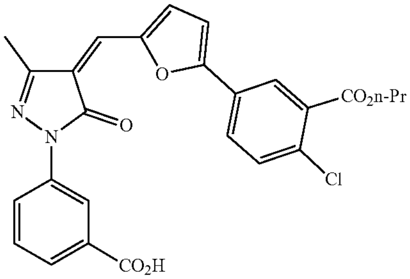 $C_{26}H_{21}ClN_2O_6$ | 7.6, 5.7 |
| 2249 | 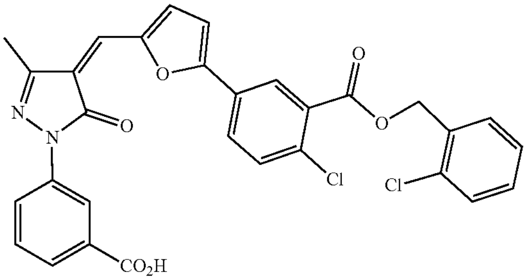 $C_{30}H_{20}Cl_2N_2O_6$ | 2.9 |
| 2922 | 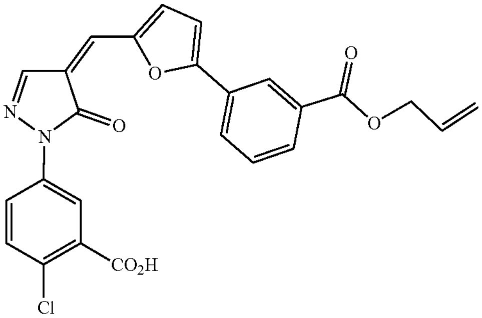 $C_{25}H_{17}ClN_2O_6$ | 6.2, 5 |
| 5135 | 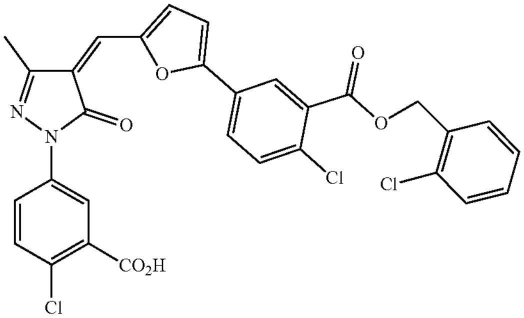 [SMILES: "C30H20Cl2N2O6" ; CC1=NN(c2cccc(C(=O)O)c2)C(=O)/C1=C\c1ccc(-c2ccc(Cl)c(C(=O)OCc3ccccc3Cl)c2)o1] $C_{30}H_{19}Cl_3N_2O_6$ | |

TABLE 1-continued
| Name | Structure | $IC_{50}$ (μM) |
|---|---|---|
| 7997 | 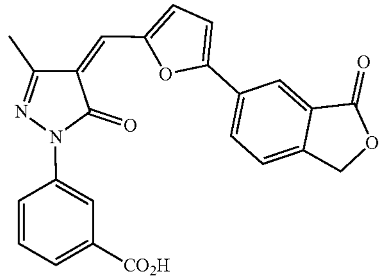 $C_{24}H_{16}N_2O_6$ | 32, 16, 40 |
| 2849 | 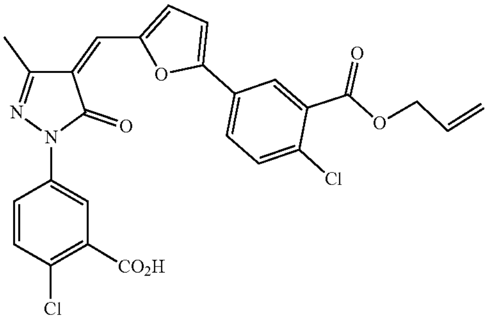 $C_{26}H_{18}Cl_2N_2O_6$ | 6.6, 6.6 |
| 2777 | 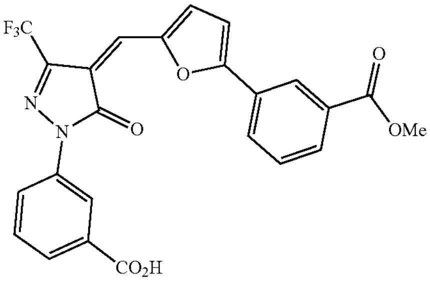 $C_{24}H_{15}F_3N_2O_6$ | 40, 16 |
| 3125 | 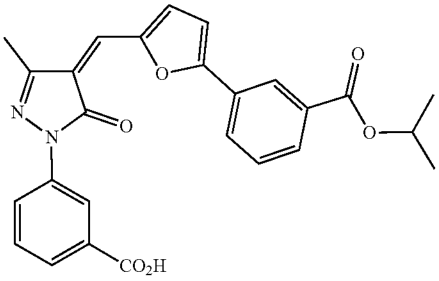 $C_{26}H_{21}ClN_2O_6$ | 11, 3.5 |

TABLE 1-continued
| Name | Structure | $IC_{50}$ (μM) |
|---|---|---|
| 3315 | 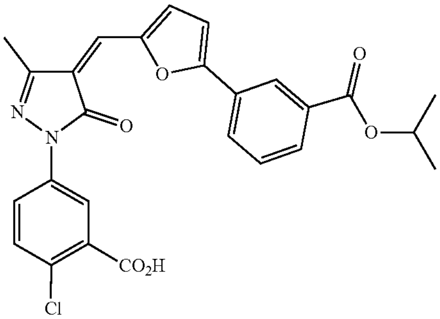 $C_{26}H_{21}ClN_2O_6$ | 31, 5.7 |
| 3278 | 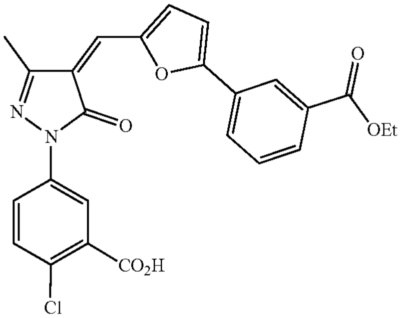 $C_{25}H_{19}ClN_2O_6$ | 4.3, 8.1 |
| 5102 | 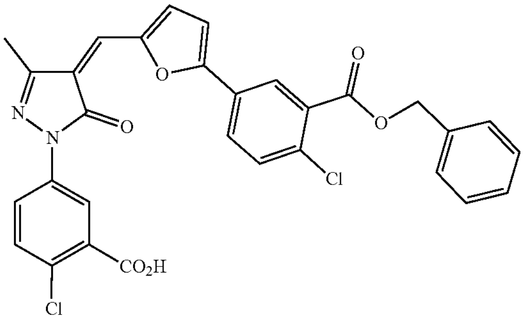 $C_{30}H_{20}Cl_2N_2O_6$ | |
| 2733 | 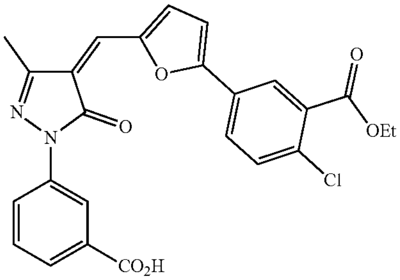 $C_{25}H_{19}ClN_2O_6$ | 4.2, 9 |

TABLE 1-continued

| Name | Structure | $IC_{50}$ (μM) |
|---|---|---|
| 4770 | 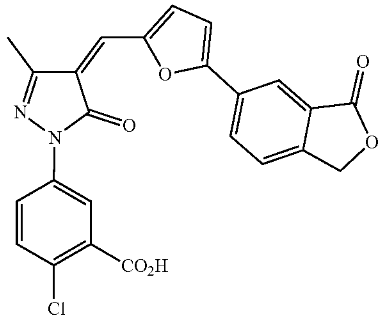 $C_{24}H_{15}ClN_2O_6$ | 21.8 |
| 7026 | 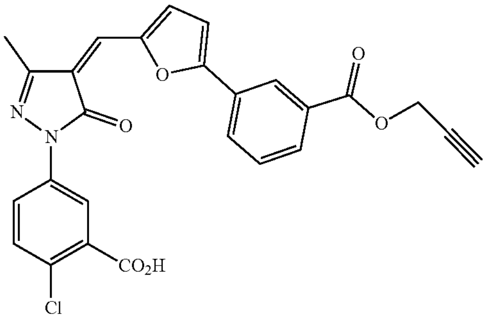 $C_{26}H_{17}ClN_2O_6$ | 16.9 |

Example 2 New Chemical Entities Targeting Ku and Assay Results

Based on the data in Table 1, we pursued a synthetic scheme and synthesized a series of derivatives to further explore the structure-activity relationships that drive Ku inhibition. The structures and inhibition data are presented in Table 2. These data revealed a series of inhibitors with varied inhibitory activities against Ku and allowed the identification of SAR for Ku inhibition.

TABLE 2

| Name | Structure | $IC_{50}$ (μM) |
|---|---|---|
| NG-01-54/01-64 | 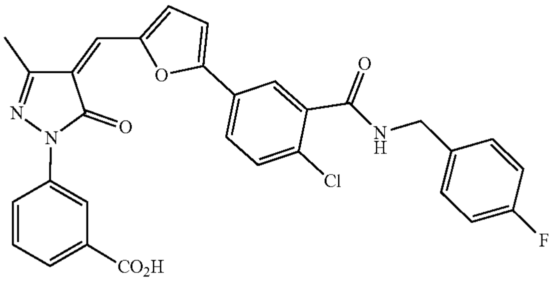 $C_{30}H_{21}ClFN_3O_5$ | 50, 30, 12, 7 |

TABLE 2-continued
| Name | Structure | $IC_{50}$ (μM) |
| --- | --- | --- |
| NG-01-65 | 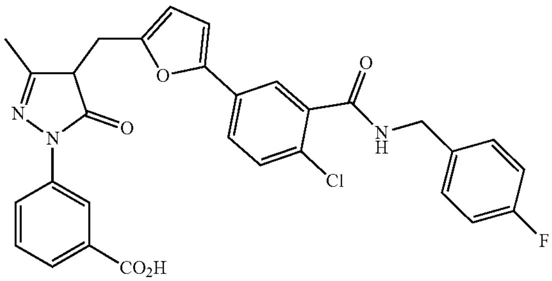 $C_{30}H_{23}ClFN_3O_5$ | 8 |
| NG-01-68/02-140/03-180 | 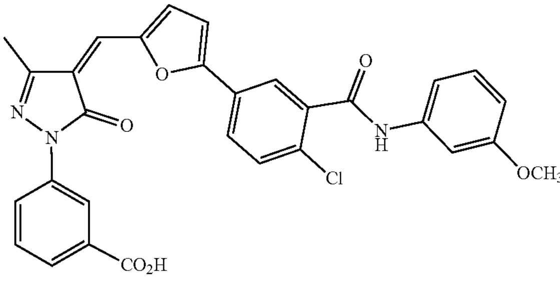 $C_{30}H_{22}ClN_3O_6$ | 6, 15, 4, 4 |
| NG-01-70 | 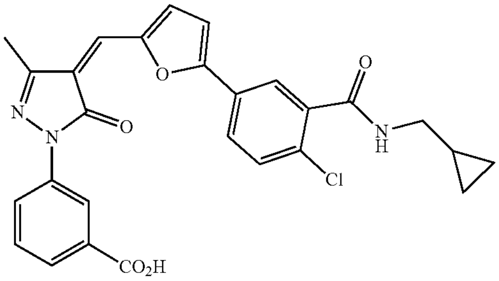 $C_{27}H_{22}ClN_3O_5$ | 25, >50 |
| NG-01-72 | 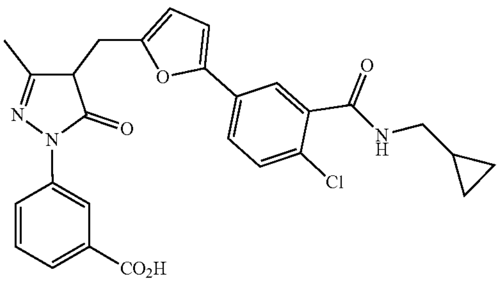 $C_{27}H_{24}ClN_3O_5$ | 10 |

TABLE 2-continued
| Name | Structure | $IC_{50}$ (μM) |
|---|---|---|
| NG-01-77 | 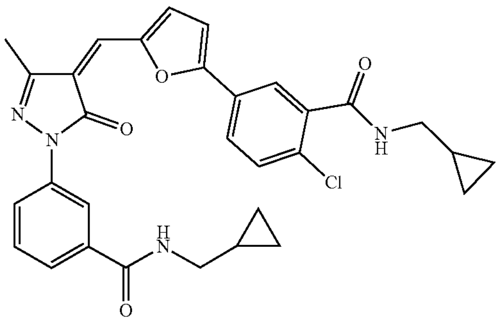 $C_{31}H_{29}ClN_4O_4$ | |
| NG-01-78 | 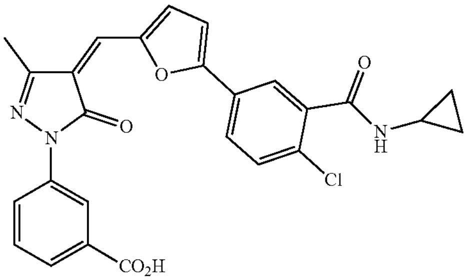 $C_{26}H_{20}ClN_3O_5$ | |
| NG-01-81 | 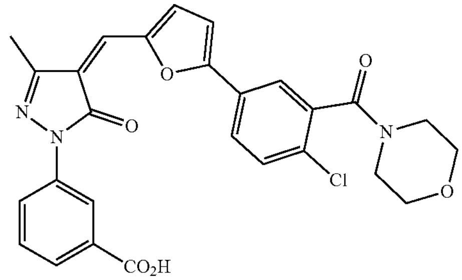 $C_{27}H_{22}ClN_3O_6$ | |
| NG-01-82 | 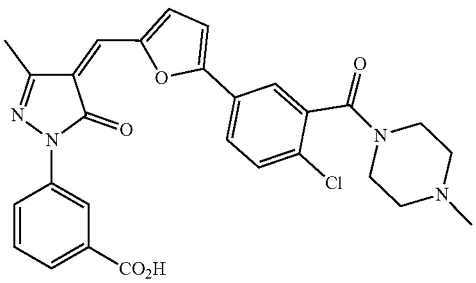 $C_{28}H_{25}ClN_nO_5$ | |

TABLE 2-continued
| Name | Structure | $IC_{50}$ (μM) |
|---|---|---|
| NG-01-91 | 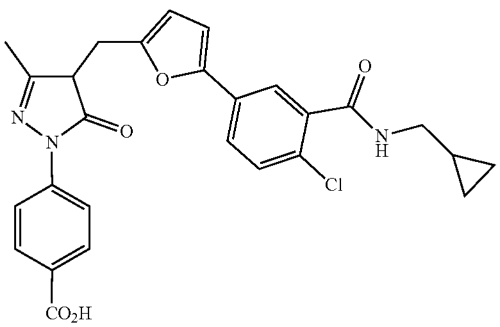 $C_{27}H_{24}ClN_3O_5$ | |
| NG-01-92 | 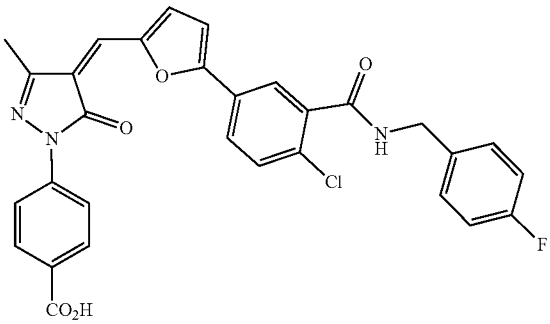 $C_{30}H_{21}ClFN_3O_5$ | |
| NG-01-99 | 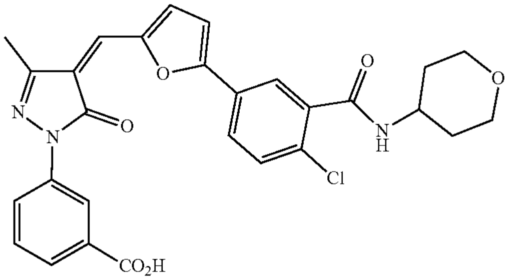 $C_{28}H_{23}ClN_3O_6$ | |
| NG-01-100 | 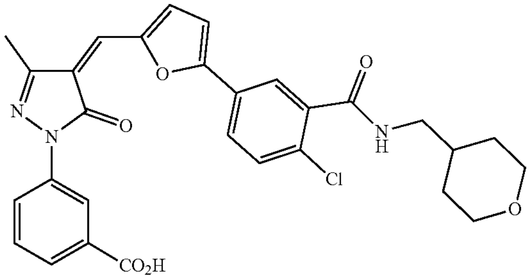 $C_{29}H_{25}ClN_3O_6$ | |

TABLE 2-continued
| Name | Structure | $IC_{50}$ (μM) |
|---|---|---|
| NG-01-104 | 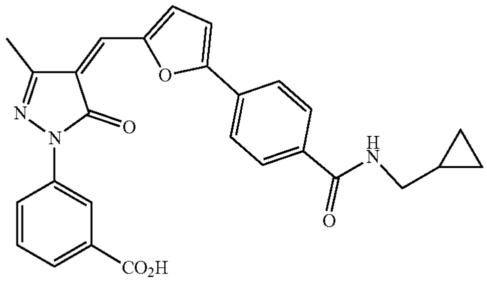 $C_{27}H_{23}N_3O_5$ | |
| NG-01-105 | 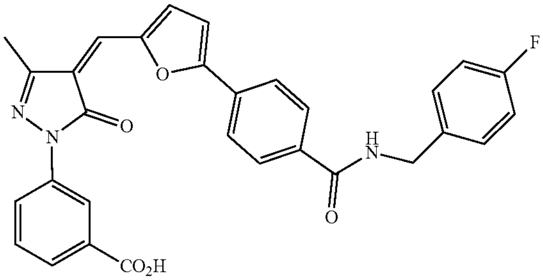 $C_{30}H_{22}FN_3O_5$ | |
| NG-01-112 | 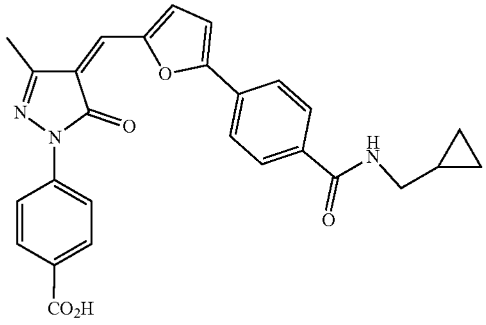 $C_{27}H_{23}N_3O_5$ | |
| NG-01-113 | 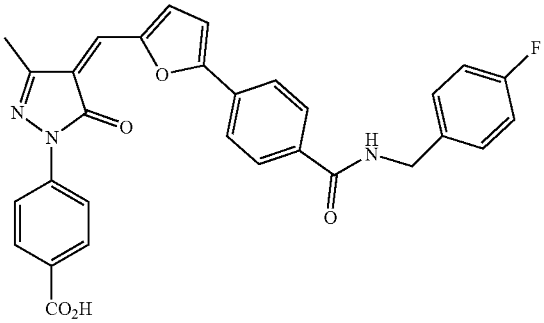 $C_{30}H_{22}FN_3O_5$ | |

TABLE 2-continued
| Name | Structure | $IC_{50}$ (μM) |
| --- | --- | --- |
| NG-02-130 | 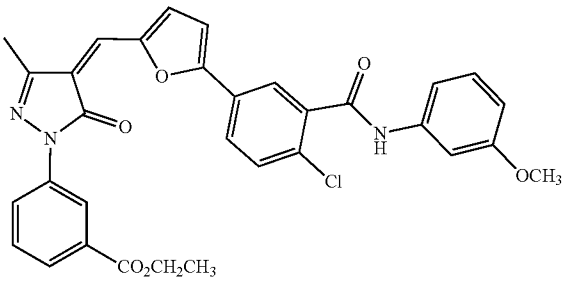 $C_{32}H_{26}ClN_3O_6$ | 3 |
| NG-02-131 | 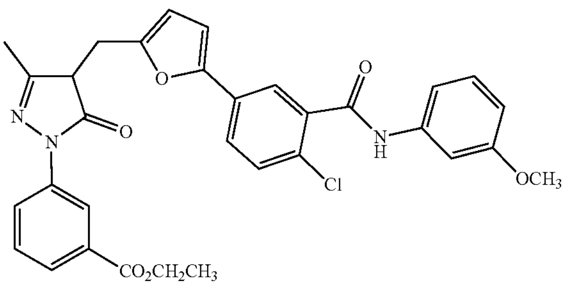 $C_{32}H_{28}ClN_3O_6$ | 3 |
| NG-02-132/ NG-02-149 | 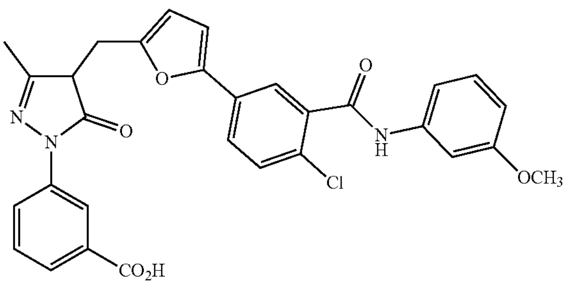 $C_{30}H_{24}ClN_3O_6$ | 1, 1, 4, 6 |
| NG-02-162/ NG-02-162C | 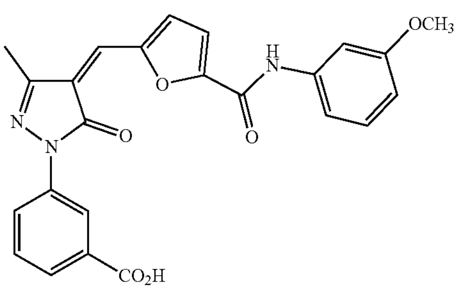 $C_{24}H_{19}N_3O_6$ | 8, 11 |

TABLE 2-continued
| Name | Structure | $IC_{50}$ (μM) |
| --- | --- | --- |
| NG-02-165 | 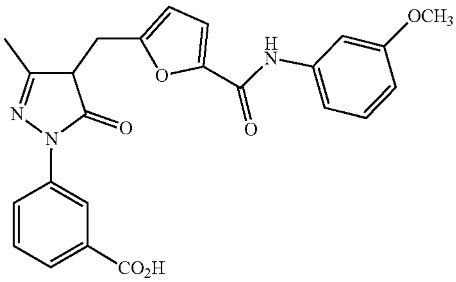 $C_{24}H_{21}N_3O_6$ | 11 |
| NG-03-185 | 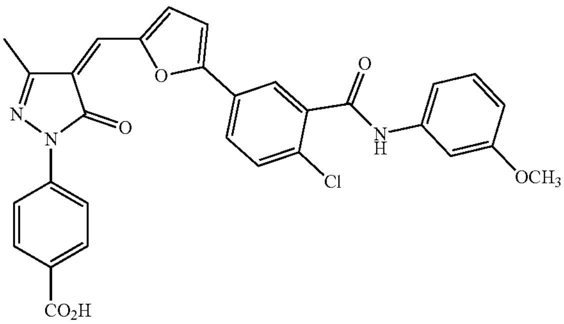 $C_{30}H_{22}ClN_3O_6$ | 5, 8, 6, 2 |
| NG-03-188 | 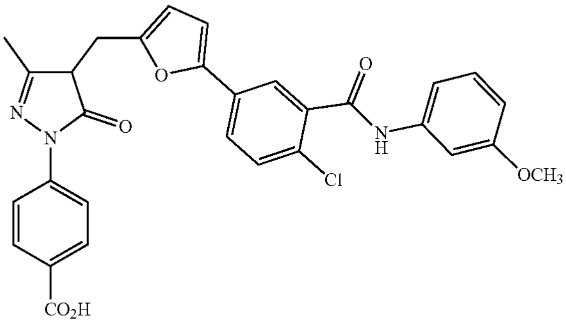 $C_{30}H_{24}ClN_3O_6$ | 12.5, 6 |
| NG-03-189 | 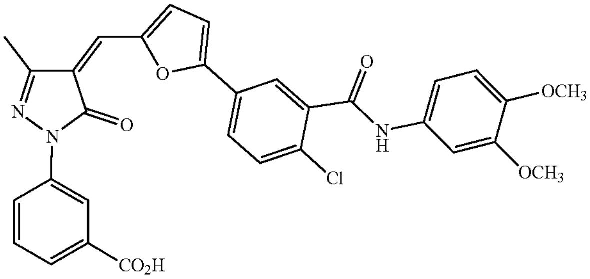 $C_{31}H_{24}ClN_3O_7$ | 14 |

TABLE 2-continued
| Name | Structure | $IC_{50}$ (μM) |
|---|---|---|
| NG-03-193 | 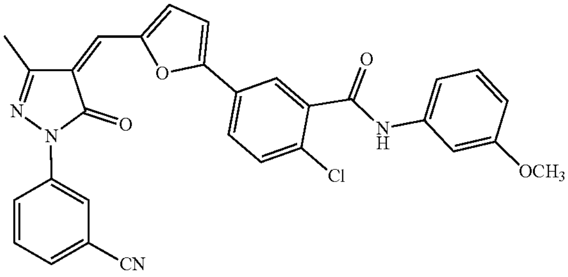<br>$C_{30}H_{21}ClN_4O_4$ | 25 |
| NG-03-196 | 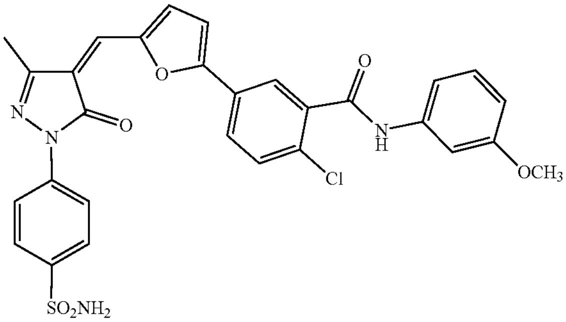<br>$C_{29}H_{23}ClN_4O_6S$ | 20 |
| NG-03-201 | 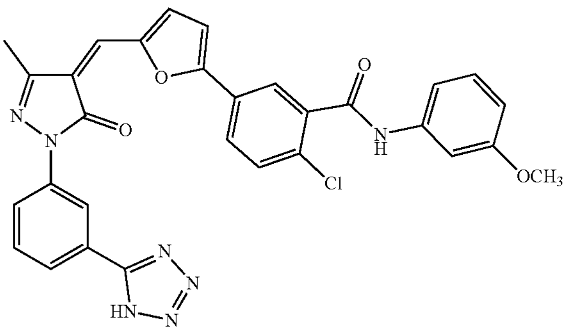<br>$C_{30}H_{22}ClN_7O_4$ | 4.5, 6.5 |
| NG-03-202 | 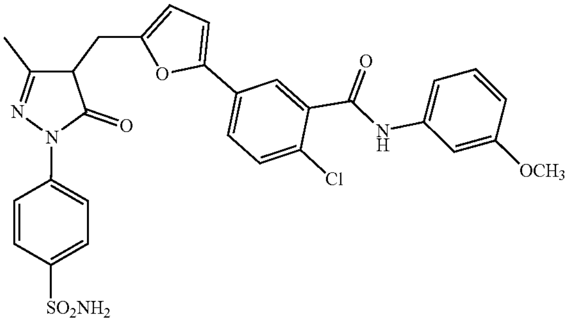<br>$C_{29}ClN_4O_6S$ | |

TABLE 2-continued
| Name | Structure | $IC_{50}$ (μM) |
|---|---|---|
| NG-03-203 | 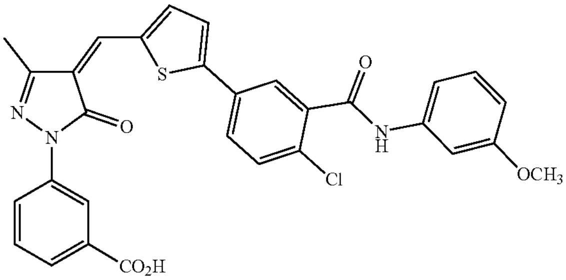 $C_{30}H_{22}ClN_3O_5S$ | 18 |
| NG-03-205 | 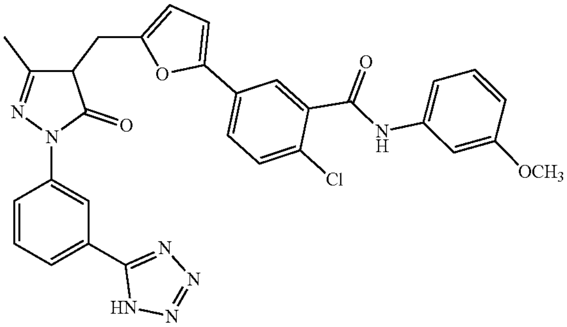 $C_{30}H_{24}ClN_7O_4$ | 13 |
| NG-03-206 | 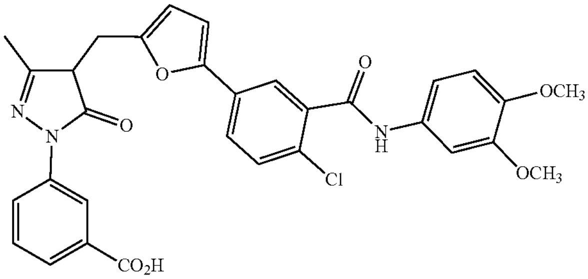 $C_{31}H_{26}ClN_3O_7$ | 7.5 |
| NG-03-207 | 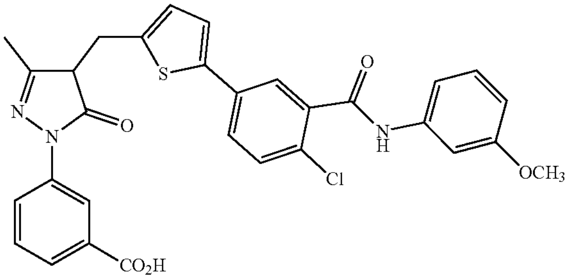 $C_{30}H_{24}ClN_3O_5S$ | 7 |

TABLE 2-continued
| Name | Structure | $IC_{50}$ (μM) |
|---|---|---|
| NG-03-212 | 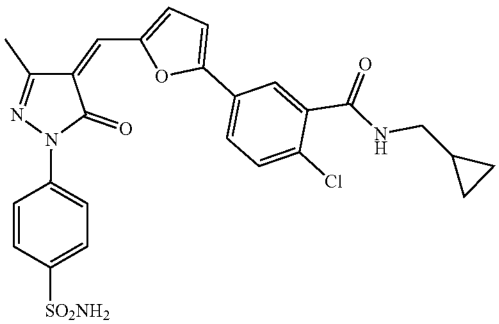 $C_{26}H_{23}ClN_4O_5S$ | 30 |
| NG-03-213 | 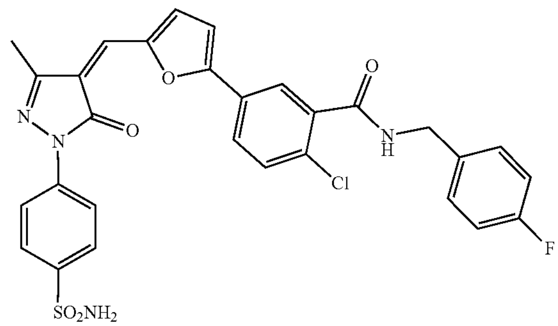 $C_{29}H_{22}ClFN_4O_5S$ | 25 |
| NG-03-224 | 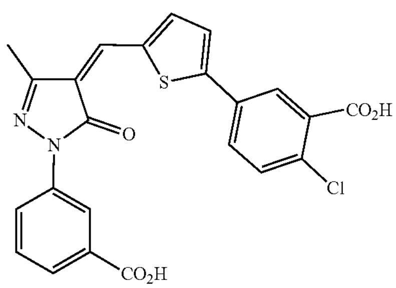 $C_{23}H_{15}ClN_2O_5S$ | 15 |
| NG-03-226 | 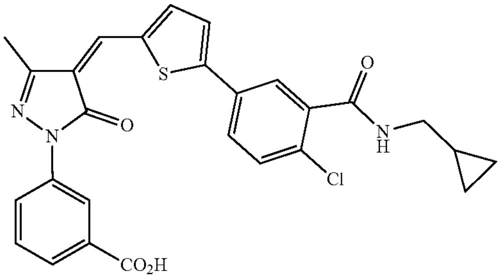 $C_{27}H_{22}ClN_3O_4S$ | 7 |

TABLE 2-continued
| Name | Structure | $IC_{50}$ (μM) |
| --- | --- | --- |
| NG-03-227 | 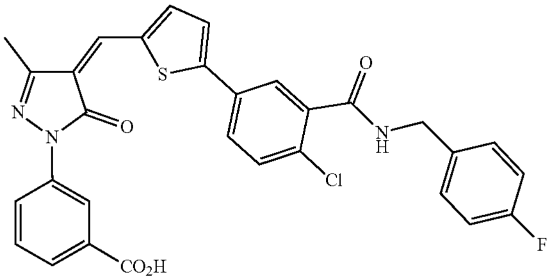 $C_{30}H_{21}ClFN_3O_4S$ | 25 |
| NG-03-231 | 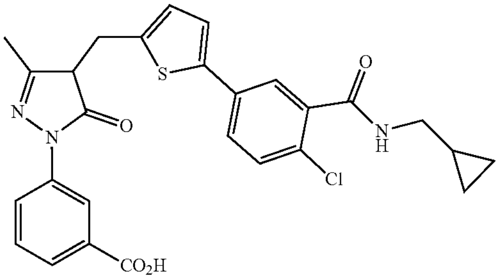 $C_{27}H_{24}ClN_3O_4S$ | 12 |
| NG-03-232 | 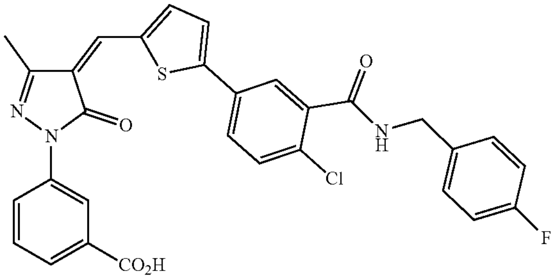 $C_{30}H_{23}ClFN_3O_4S$ | 6 |
| NG-03-234 | 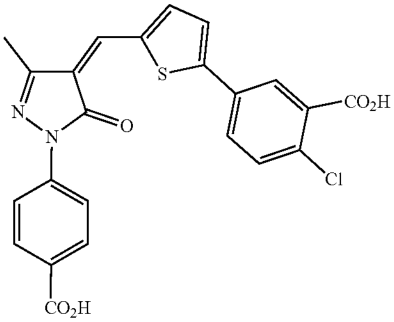 $C_{23}H_{15}ClN_2O_5S$ | 6 |

TABLE 2-continued
| Name | Structure | $IC_{50}$ (μM) |
|---|---|---|
| NG-03-235 | 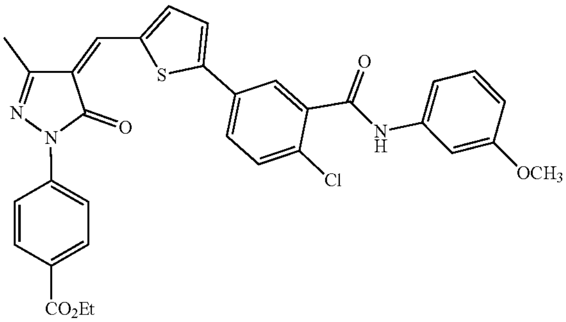 $C_{32}H_{26}ClN_3O_5S$ | 8.75 |
| NG-03-236 | 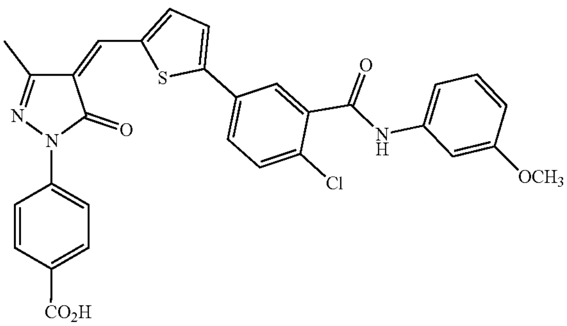 $C_{30}H_{22}ClN_3O_5S$ | 10 |
| NG-03-238 | 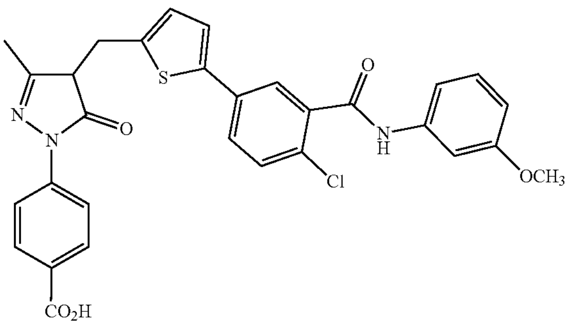 $C_{30}H_{24}ClN_3O_5S$ | 14 |
| NG-02-201/NG-03-244 | 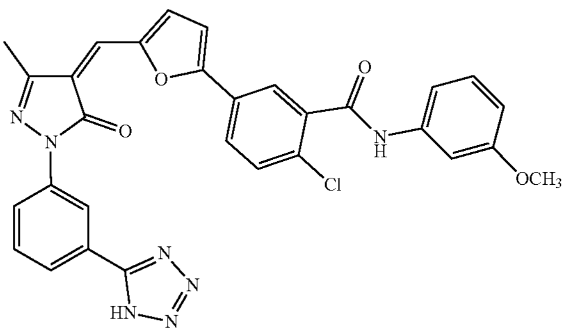 $C_{30}H_{24}ClN_7O_4$ | 4 |

TABLE 2-continued

| Name | Structure | $IC_{50}$ (μM) |
|---|---|---|
| NG-03-270 | 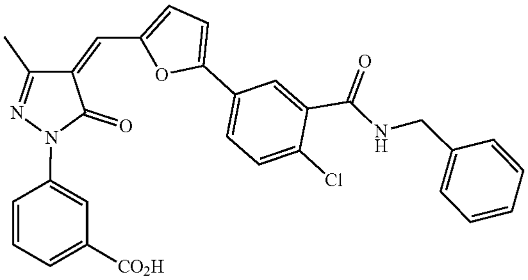 $C_{30}H_{22}ClN_3O_5$ | 10 |
| NG-03-271 | 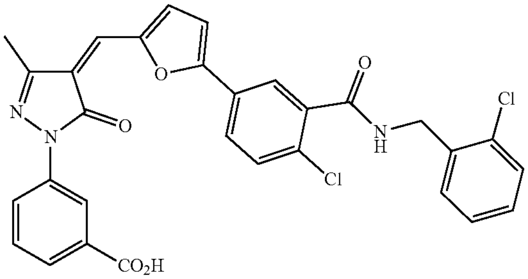 $C_{30}H_{21}Cl_2N_3O_5$ | 18 |
| NG-03-280 | 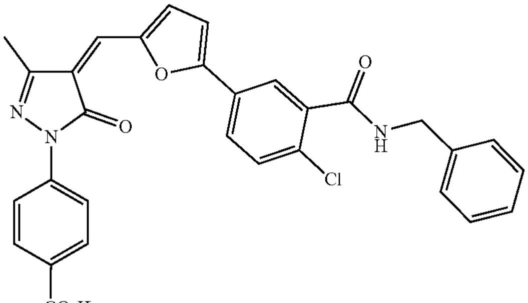 $C_{30}H_{22}ClN_3O_5$ | 22 |
| NG-03-286 | 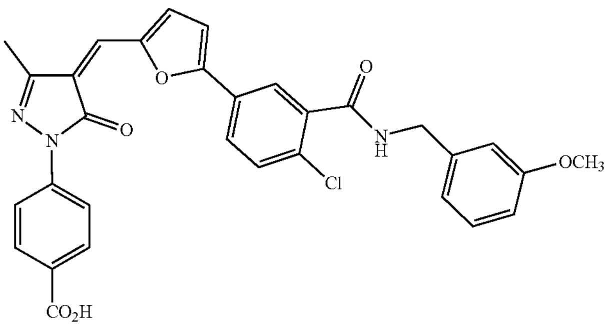 $C_{31}H_{24}ClN_3O_6$ | 30 |

Example 3: Inhibition of NHEJ Activity

Disruption of Ku-DNA binding should result in inhibition of NHEJ activity, and to test this inhibition we will employ a host cell reactivation assay. This assay utilizes a linearized plasmid encoding a GFP gene that is transfected into the cell and expressed upon NHEJ mediated re-circularization of the plasmid (Sears, C A., 2012 and Woods, D., 2015). Co-transfection of a circular RFP plasmid accounts for differences in transfection efficiency, and NHEJ mediated repair of the GFP plasmid can be quantified by assessing the ratio of green:red cells. This assay will be used to assess the Ku inhibitor compounds in H460 and HEK-293 cells, and the data obtained from these experiments will allow us to determine the sensitivity of the chemical compounds and effect of Ku inhibition on NHEJ activity. As this is a cellular assay, we will also utilize this assay to do a series of time course experiments to determine the optimal time to deliver the inhibitor to cells in order to achieve maximum inhibition of NHEJ activity. Preliminary data we very recently obtained demonstrate that compound NG-01-68, when pre-incubated with H460 cells 2 hours prior to transfection of the reporters, was capable of reducing NHEJ catalyzed repair events from 26% to 17% measured 48 hours post transfection. This 35% reduction in a first pass experiment portends the possibility for rapid development to determine the optimal treatment regimen to maximally inhibit NHEJ and stimulate HDR mediate genome editing.

Figure 3:
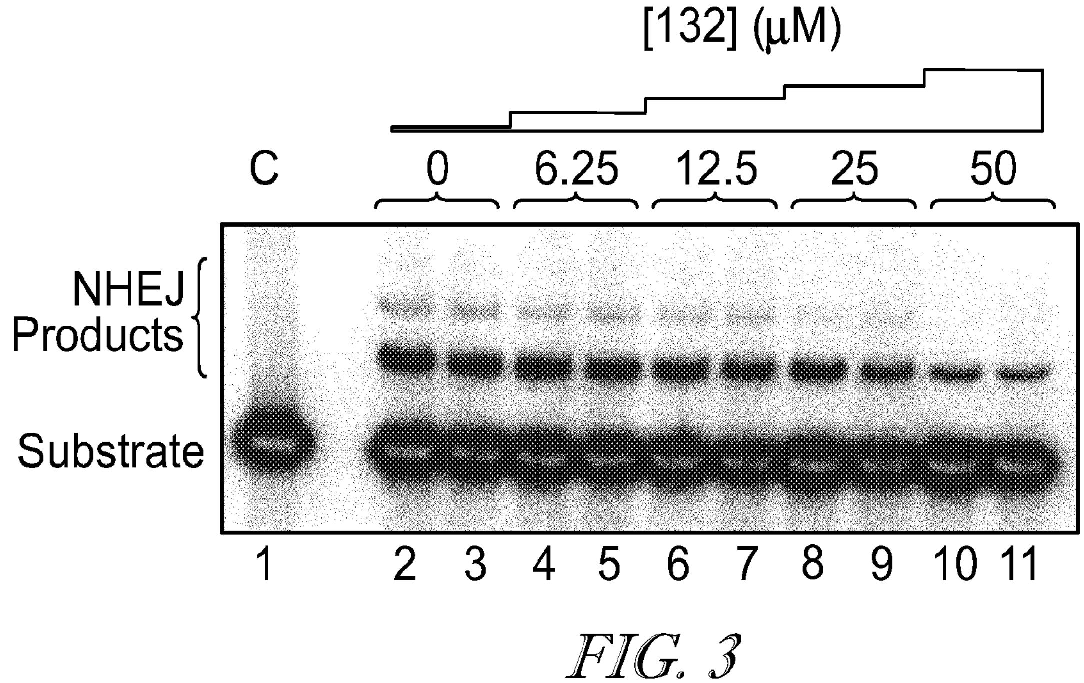
FIG. 3 shows results for an in vitro NHEJ assay. Radiolabeled linearized DNA was incubated with whole cell extracts with increasing amounts of inhibitor NG-02-132.

A linearized plasmid DNA (3 kbp) is incubated with a cell free extract prepared from a NHEJ competent cell (HEK 293) and ATP. The results presented in FIG. 3 show the substrate alone in lane 1 and the degree of end joining control reactions as evidenced by the formation of plasmid multimers. Pre-incubation of the extract with NG-02-132 resulted in inhibition of end joining. Quantification of the data revealed an $IC_{50}$ of ~15 uM, consistent with the in vitro Ku DNA binding. These data demonstrate target engagement in a complex protein mixture. Results are shown in FIG. 3.

Example 4: Increase in HDR Efficiency

To determine how reduced NHEJ activity through Ku inhibition affects HDR activity, the effect of Ku inhibitors will be assessed using a published HDR dependent assay (Pierce, A J., 1999). This assay utilizes a genomic substrate that upon cleavage by I-SceI undergoes a recombination event that results in the expression of GFP. GFP expression can be quantified by flow cytometry, and serves as a quantitative indicator of homology directed repair of DSB. Plasmids necessary for the assay have been obtained from Vera Gurbonova and acceptor cell lines have been generated for use in the assay (Seluanov, A., 2010). Similar to experiments described above for assessing NHEJ, this assay will be used to determine how the Ku inhibitors affect HDR activity.

Example 5: Enhancement of Crispr/Cas9 Mediated Gene Engineering

Figure 4A:
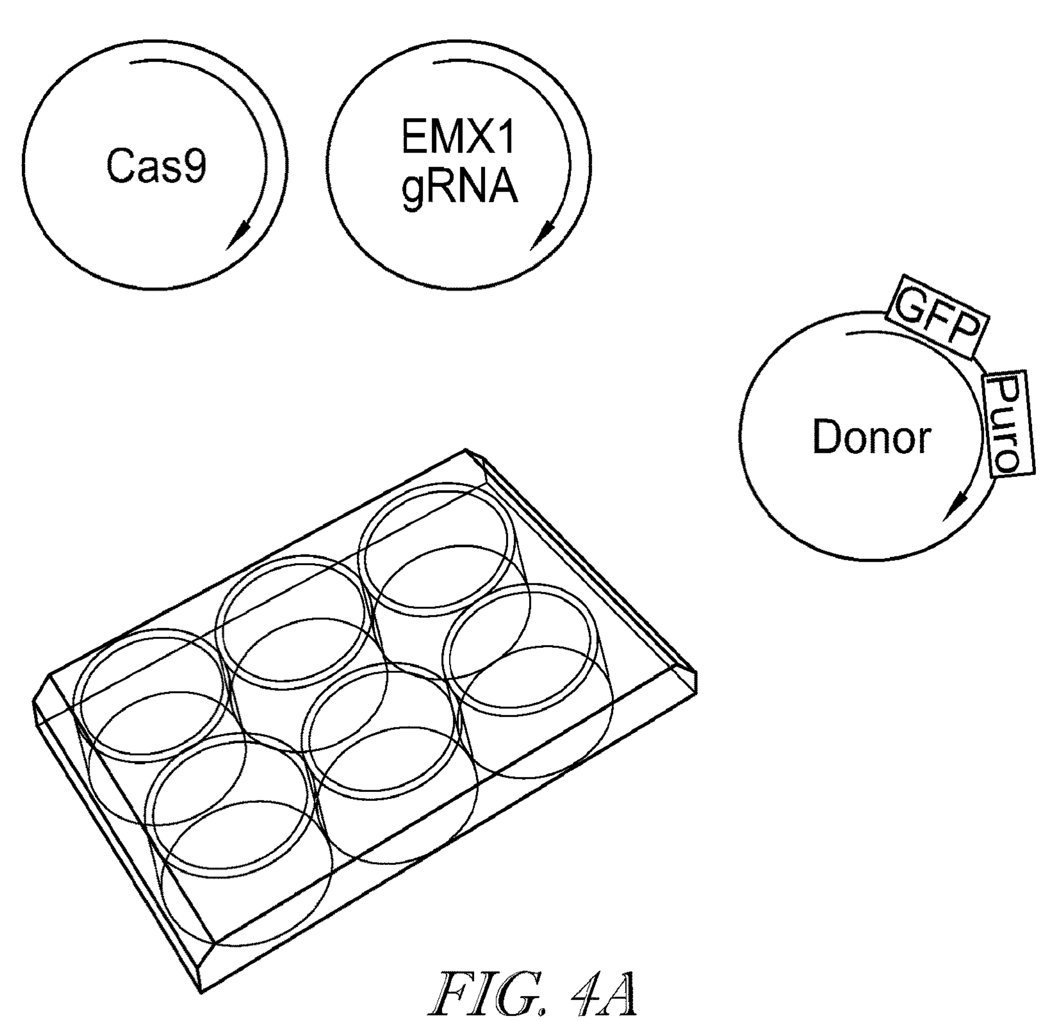
FIG. 4A shows a schematic of the CRISPR components used in Biological Example 5.
Figure 4B:
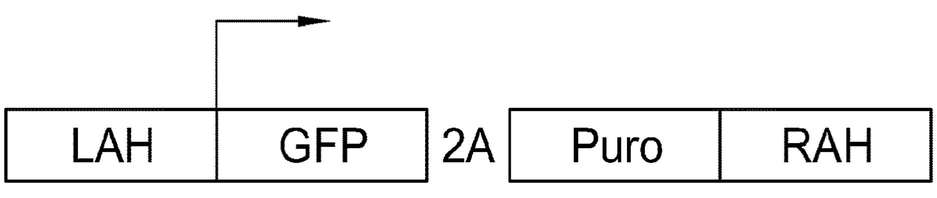
FIG. 4B shows detail of the Donor plasmid 5.2 kb (left arm homolgy (LAH) 0.8 kb; Transgene insert 2.2 kb; left arm homolgy (LAH) 0.8 kb).
Figure 5A:
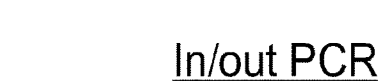
FIG. 5A shows schematic of PCR gene insertion (L1/L2: 1.2 kb; $R^1$/R2: 1.2 kb).
Figure 5A:
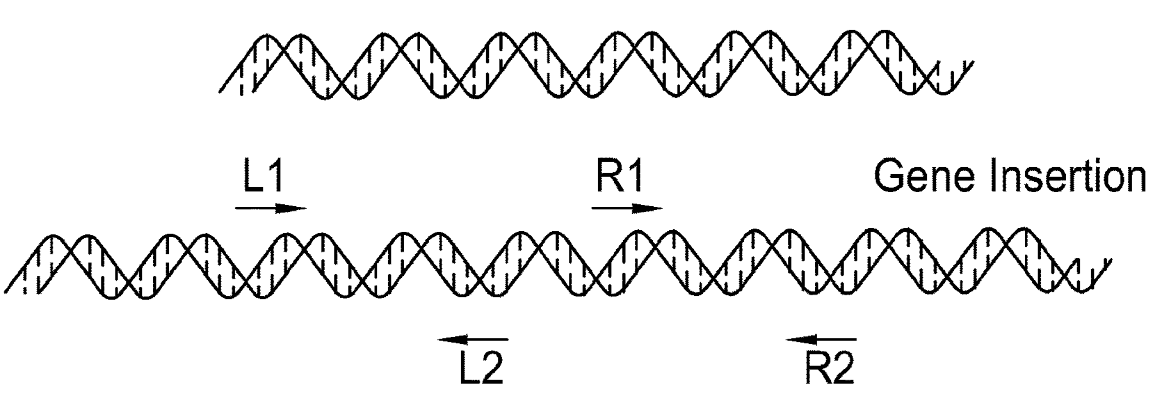
Figure 5B:
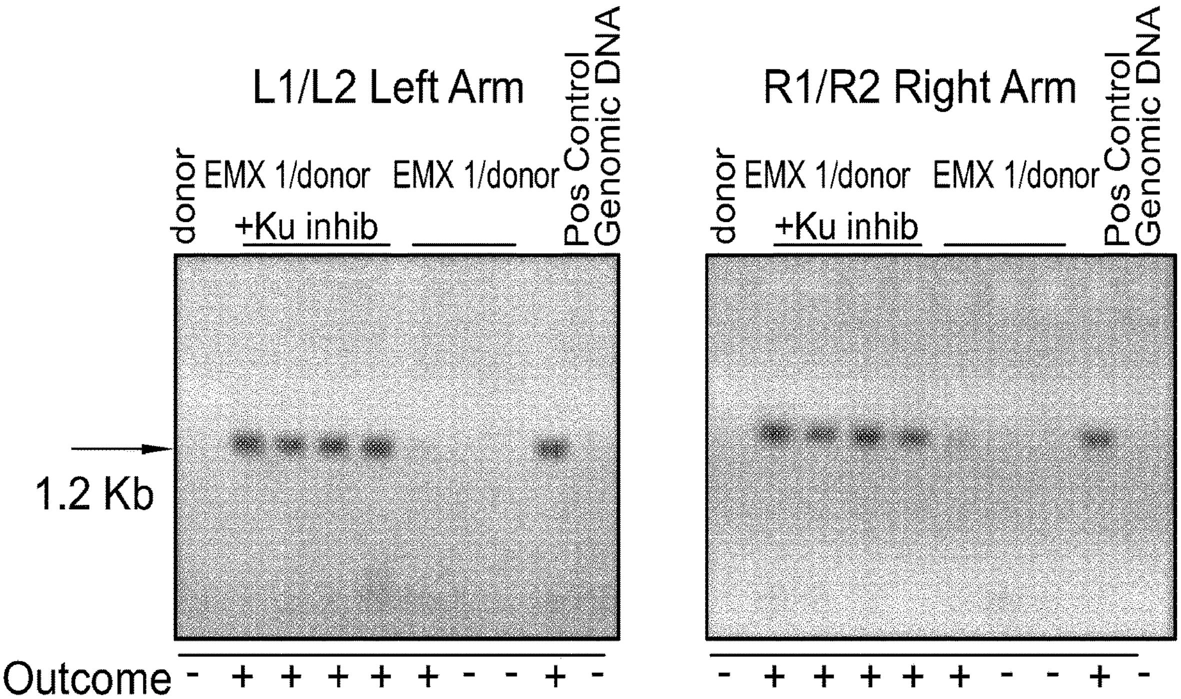
FIG. 5B shows gel images of CRISPR gene insertion.

To assess the effect of Ku inhibitors on genome engineering efficiency we designed an assay to quantify the recombination efficiency of a Crispr/Cas9 mediated gene insertion event. A donor insert of 2.2 kbp encoding puromycin resistance and a GFP gene was flanked by 800 bp homology arms directing the insert to the EMX1 locus. A guide RNA directing the Cas9 nuclease to the EMX1 gene was purchased and co-transfected with the donor construct and Cas9 expressing plasmid in H460 non-small cell lung cancer cells that were either treated with vehicle or 20 uM 205. 24 hours later, cells were placed under selection with puromycin for 5 days and plated in 96-well plates for single cell cloning. Clones were expanded, genomic DNA isolated and location specific PCR analysis was performed to assess accurate gene insertion at the EMX1 locus. The data demonstrate a greater than 6-fold increase in precise genome insertion efficiency when cells were pre-incubated with a Ku inhibitor. Results are shown in FIG. 4, FIG. 5, and Table 3.

TABLE 3

| EMX1 CRISPR/Cas9 Results | | |
|---|---|---|
| | +Inhibitor | −Inhibitor |
| Clones | 5 | 28 |
| In/Out+ | 4 | 4 |
| Efficiency | 80% | 14% |

Reduced over-all number of puromycin-resistant cells
Increased HDR mediated gene-insertion into a CRISPR/Cas9 generated cut site by ~6 fold

We claim:

1. A method of gene editing comprising a. contacting a compound with at least one cell comprising at least one programmable nuclease, wherein the at least one programmable nuclease comprises a Cas9 endonuclease; and wherein the compound is of formula I

I

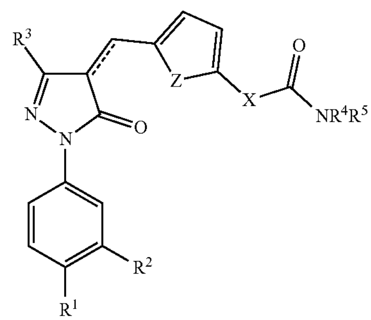

wherein

X is absent

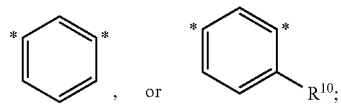

, or ;

Z is O or S;

$R^1$ is H, $—CO_2R^6$, or $—S(O)_2NR^6R^7$;

$R^2$ is H, $—CO_2R^6$, —CN, or tetrazolyl;

$R^3$ is $C_1$-$C_6$ alkyl;

$R^4$ is selected from the group consisting of

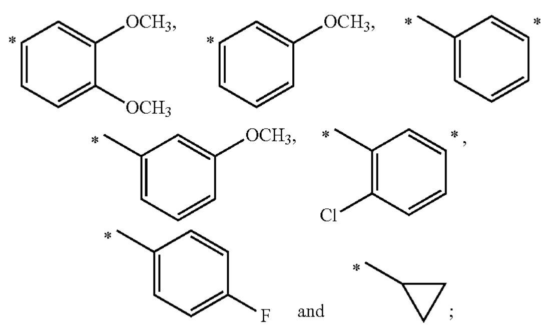

, , , , and ;

$R^5$ is H;

$R^6$ and $R^7$ are each independently H, or $C_1$-$C_6$ alkyl;

$R^{10}$ is halogen;

"*" represents the point of attachment as indicated in Formula I; and

═══ is either a single bond or a pi-bond; and b. contacting the at least one cell with a plasmid encoding a guide RNA (gRNA) comprising a Clustered Regularly Interspaced Short Palindromic repeat RNA (crRNA) and a trans-activating RNA (tracrRNA).

2. The method of claim 1, wherein the compound is of the formula Ia (Ia)

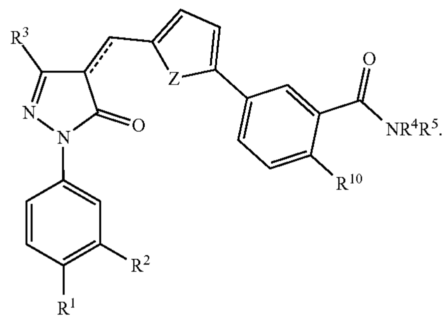

3. The method of claim 2, wherein the compound is of the formula Ib (Ib)

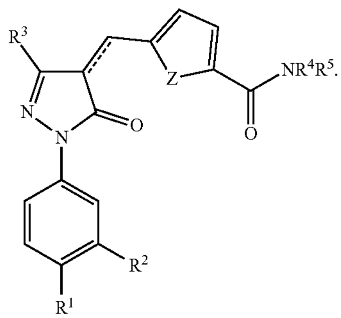

4. The method of claim 1, wherein $R^1$ is H, —$CO_2H$, —$S(O)_2NH_2$, or —$CO_2Et$; and $R^2$ is H, —$CO_2H$, —$CO_2Et$, —CN, or tetrazolyl, provided that at least one of $R^1$ and $R^2$ is not H.

5. The method of claim 4, wherein $R^1$ is H, and $R^2$ is tetrazolyl.

6. The method of claim 4, wherein $R^1$ is —$S(O)_2NH_2$ and $R^2$ is H.

7. The method of claim 1, wherein the Cas9 endonuclease is encoded in a plasmid.

8. The method of claim 1, wherein the at least one cell is a bacterial cell, a mammalian cell, a yeast cell, or a plant cell.

9. The method of claim 1, wherein $R^3$ is methyl.

10. The method of claim 1, wherein $R^4$ is selected from the group consisting of

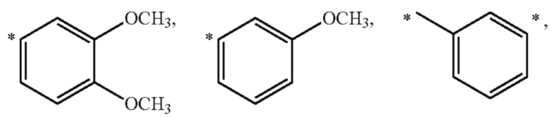

-continued

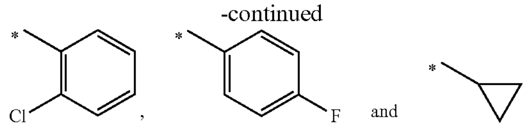

wherein * represents the point of attachment of $R^4$ to the amide nitrogen.

11. The method of claim 1, wherein the compound is selected from the group consisting of

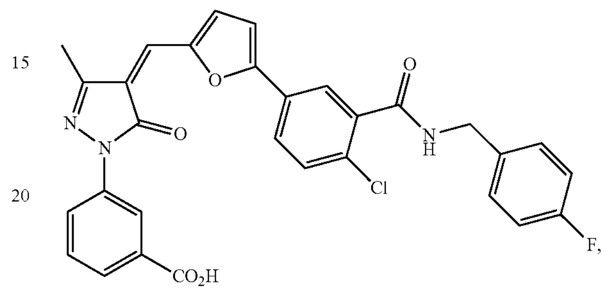

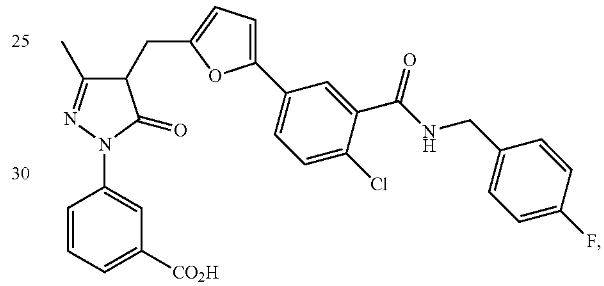

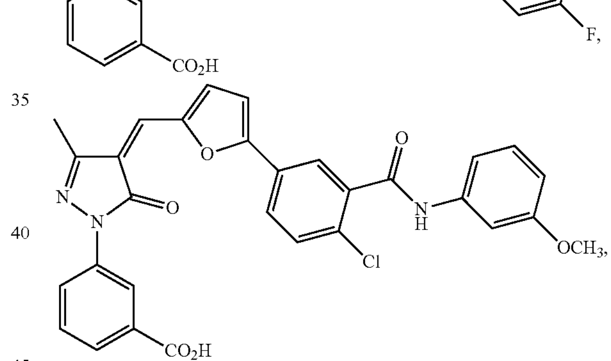

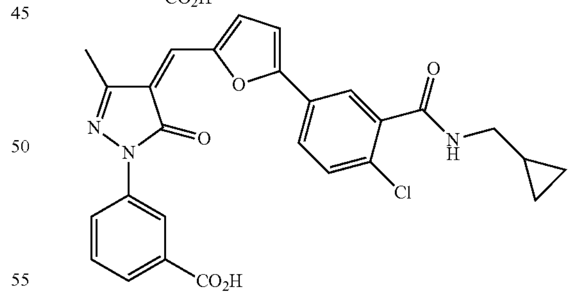

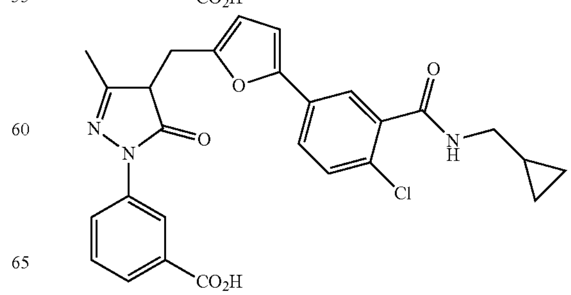

-continued
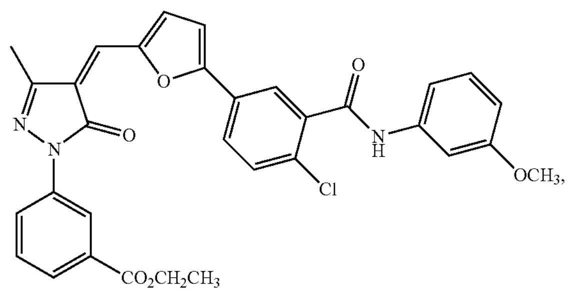
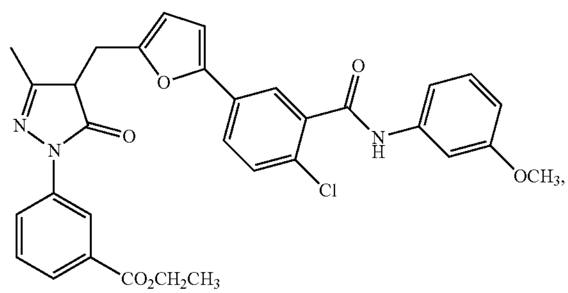
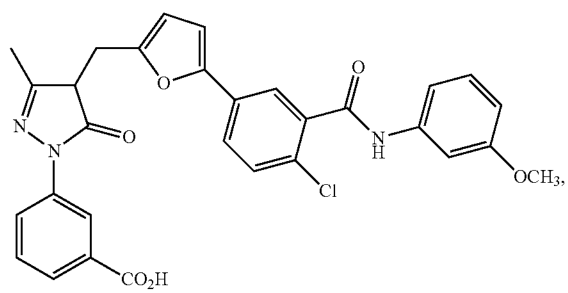
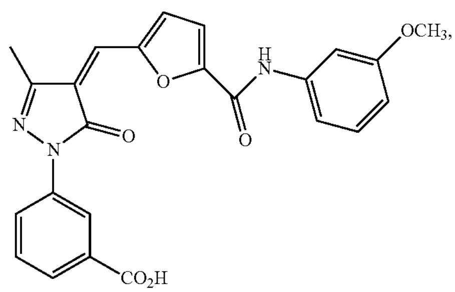
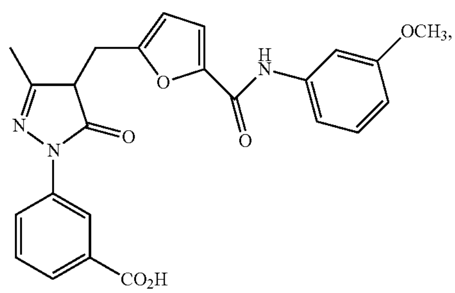
-continued
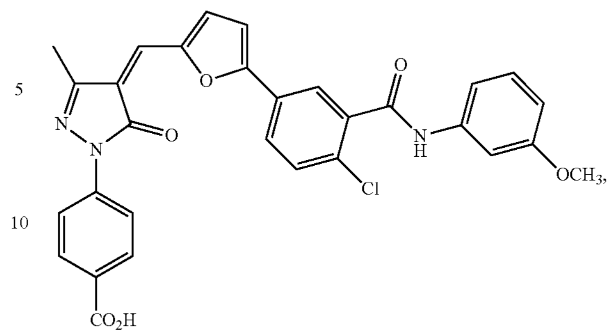
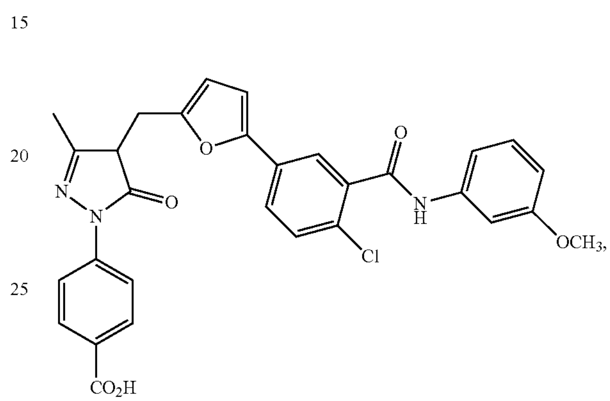
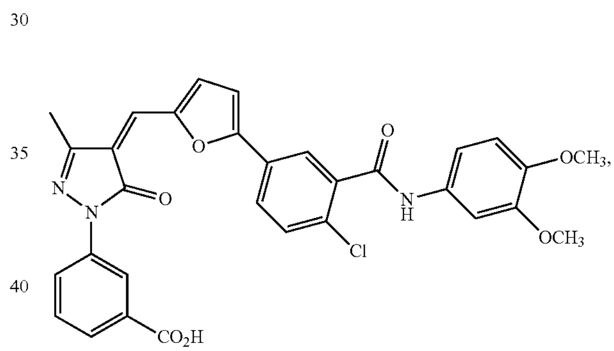
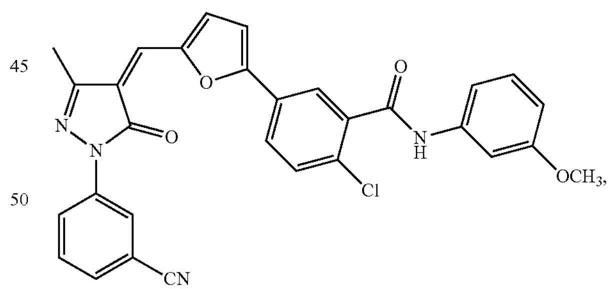
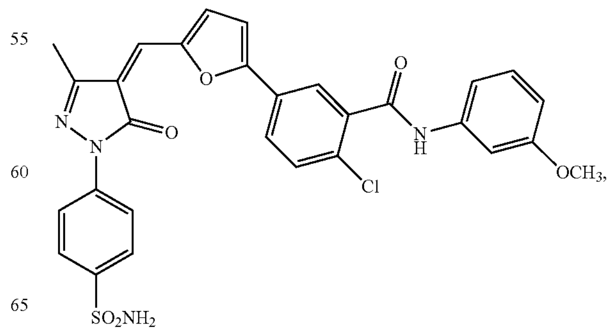

-continued
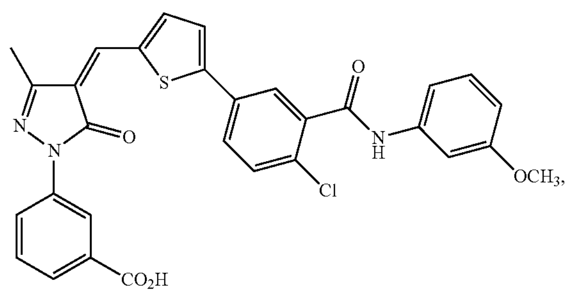
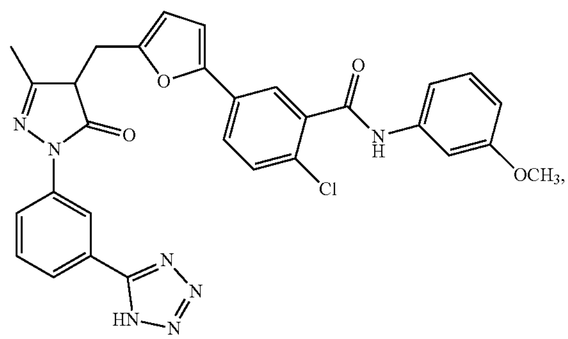
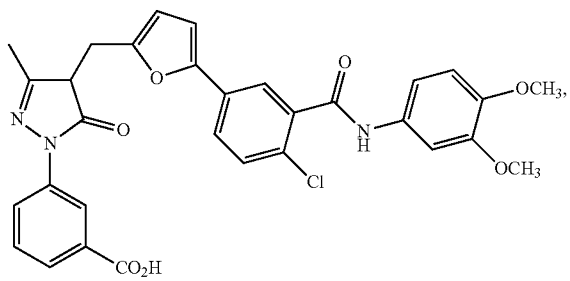
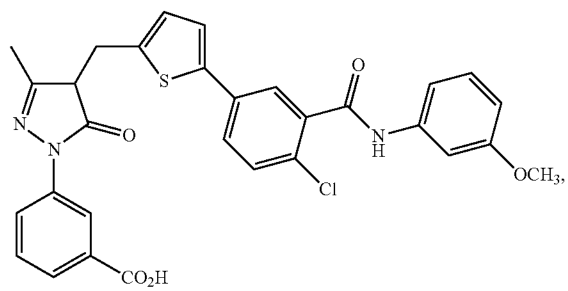
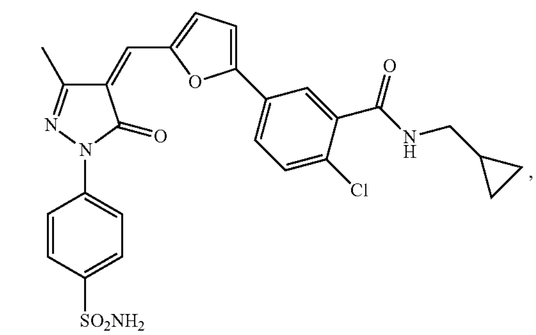
-continued
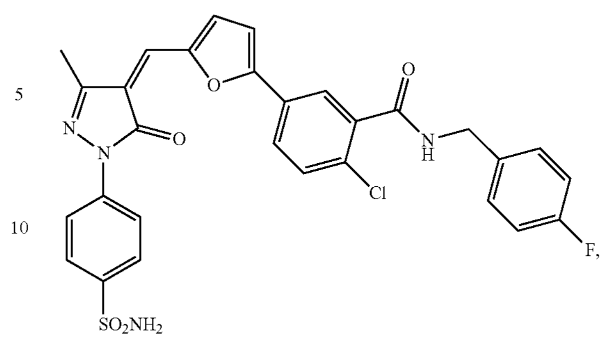
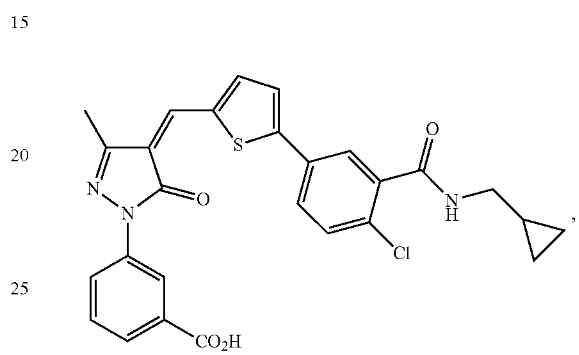
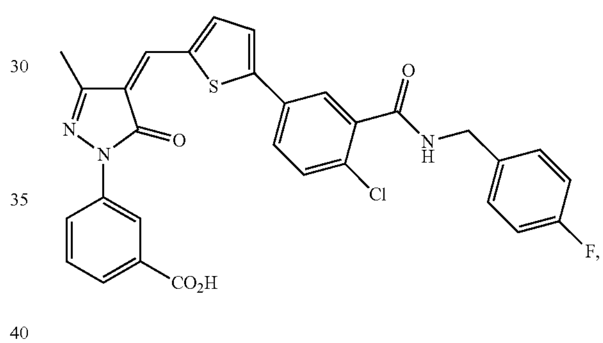
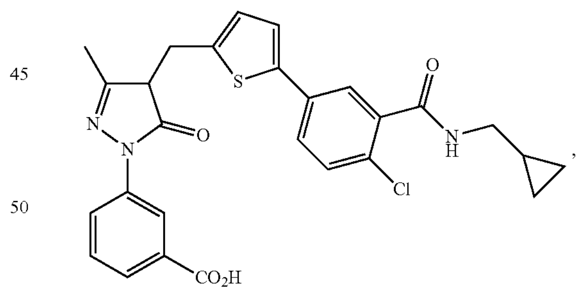
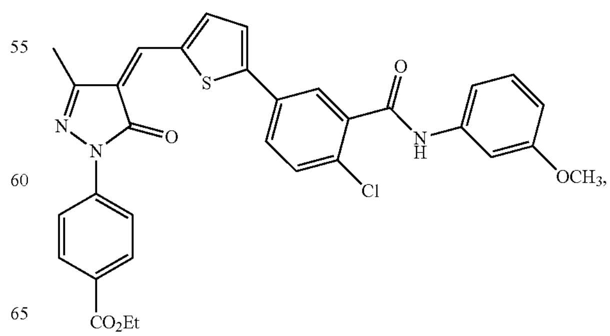

-continued
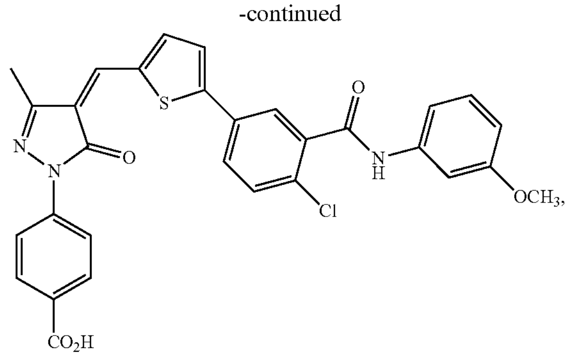
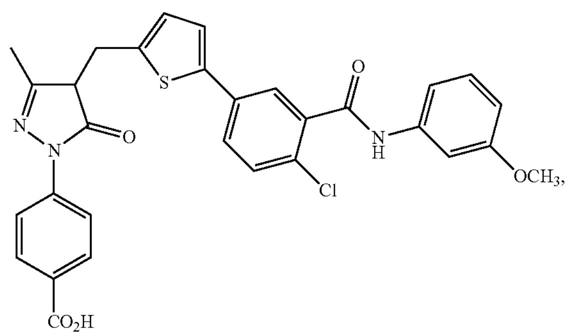
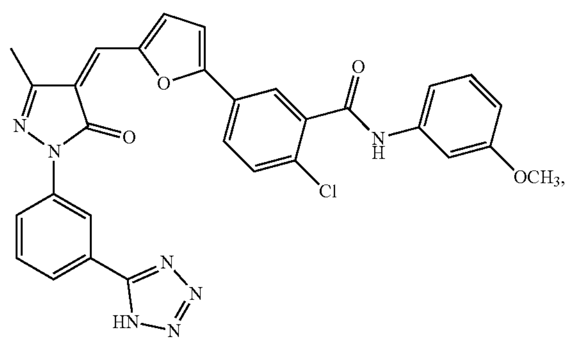
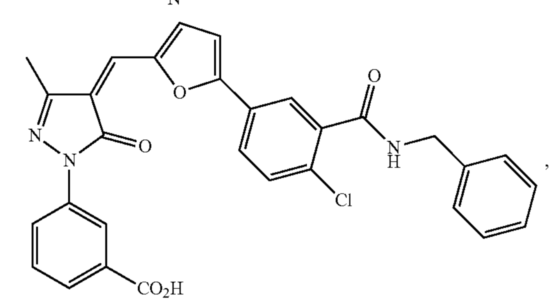
,
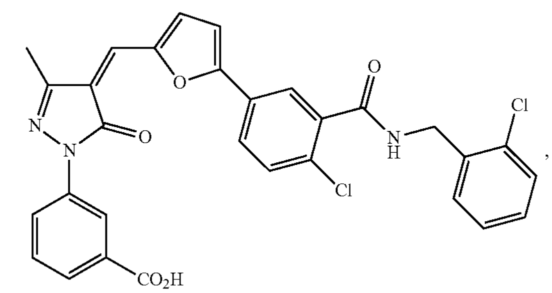
,
-continued
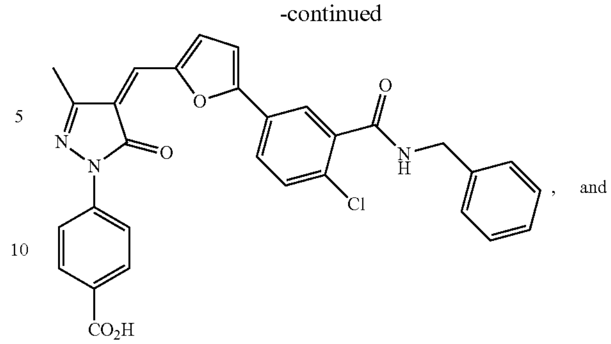
, and
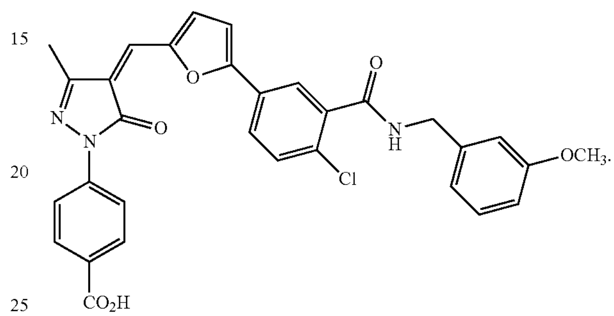
12. The method of claim 1, wherein the compound is selected from the group consisting of
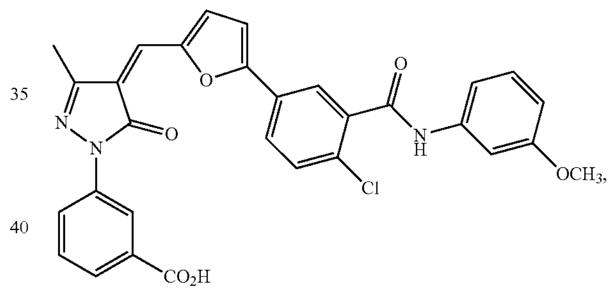
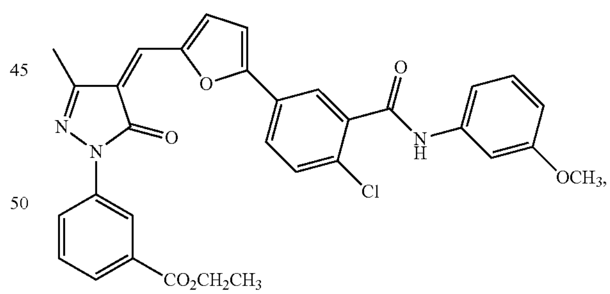
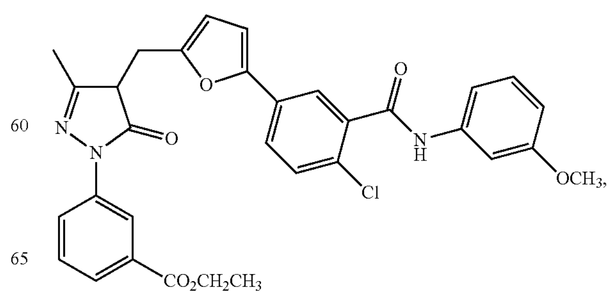

-continued
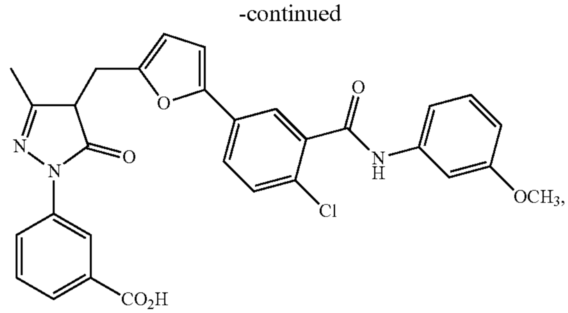
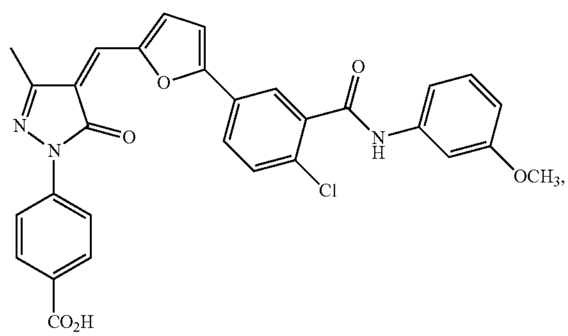
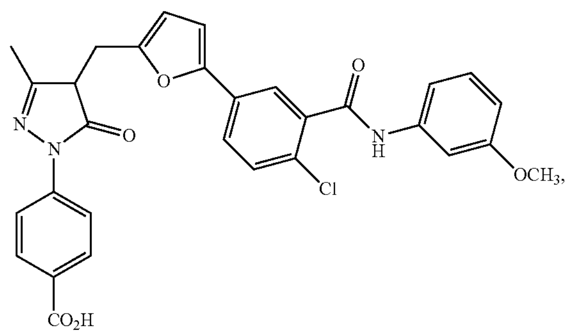
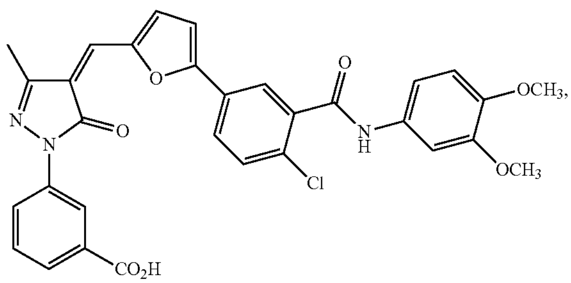
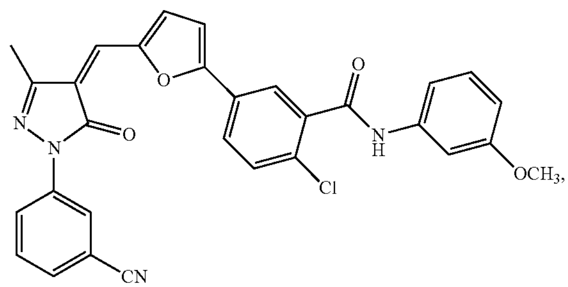
-continued
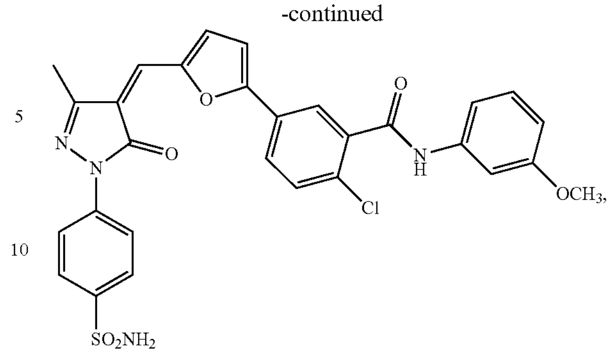
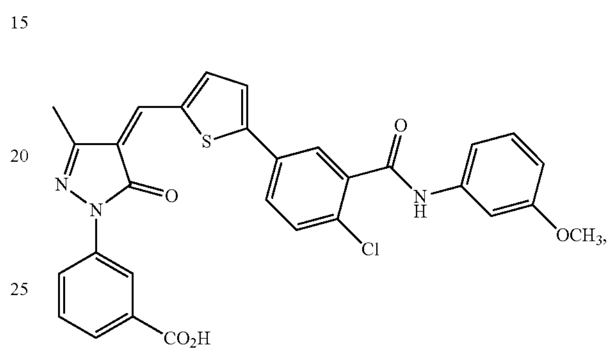
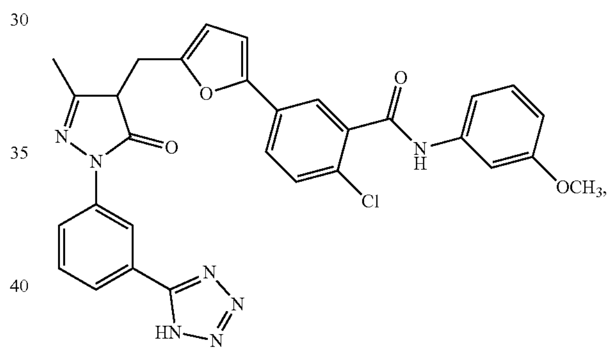
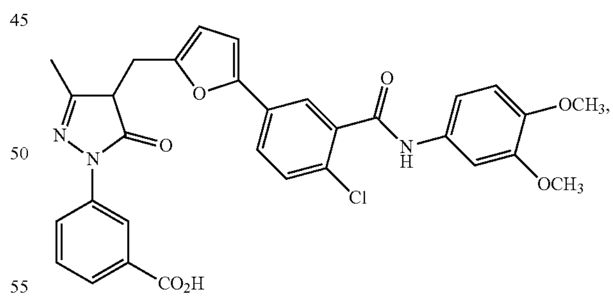
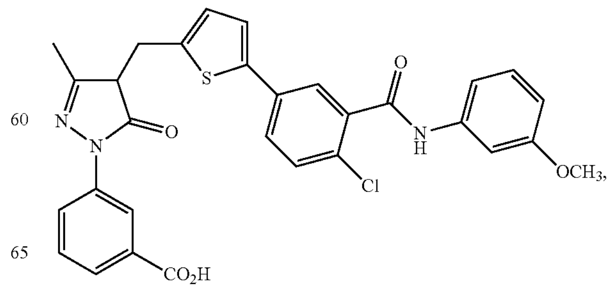

-continued

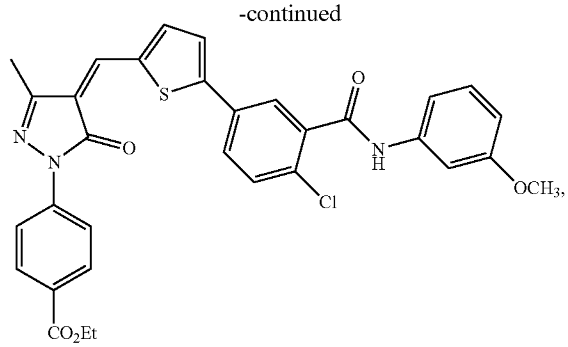

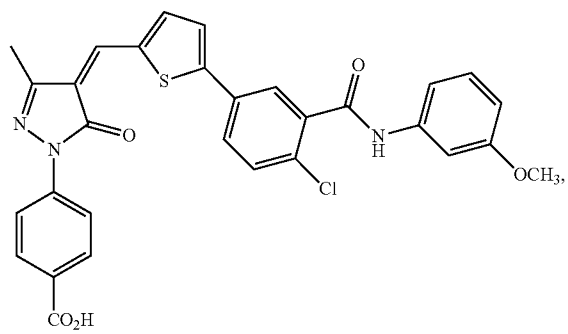

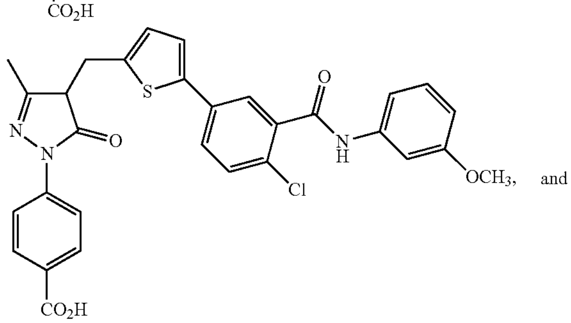

and

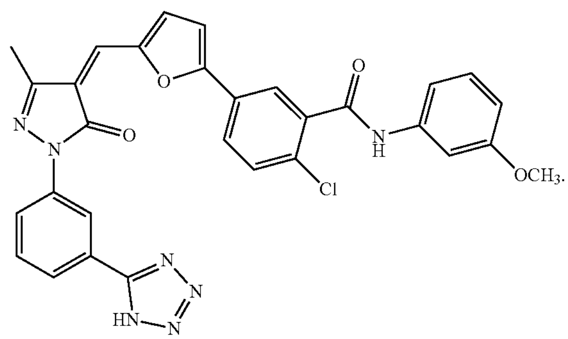

13. The method of claim 1, wherein X is absent,

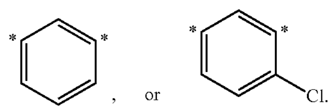

14. The method of claim 13, wherein X is C

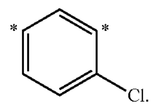

15. The method of claim 1, wherein
X is absent,

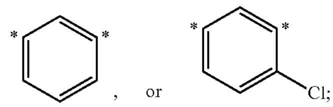

$R^1$ is H, —$CO_2H$, —$S(O)_2NH_2$, or —$CO_2Et$;
$R^2$ is H, —$CO_2H$, —$CO_2Et$, —CN, or tetrazolyl;
$R^3$ is methyl;
$R^4$ is selected from the group consisting of

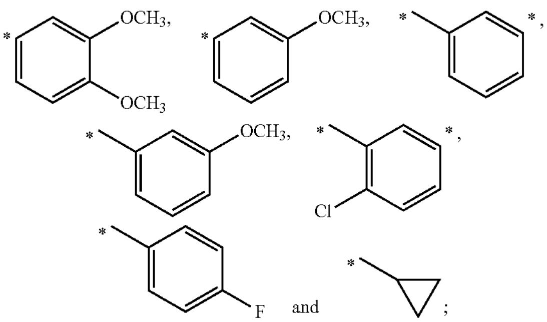

"*" represents the point of attachment as indicated in Formula I; and
$=\!=\!=$ is either a single bond or a pi-bond.

16. The method of claim 1, wherein
X is absent claim 1, wherein

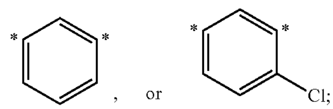

$R^1$ is H, —$CO_2H$, —$S(O)_2NH_2$, or —$CO_2Et$;
$R^2$ is H, —$CO_2H$, —$CO_2Et$, —CN, or tetrazolyl;
$R^3$ is methyl;
$R^4$ is selected from the group consisting of

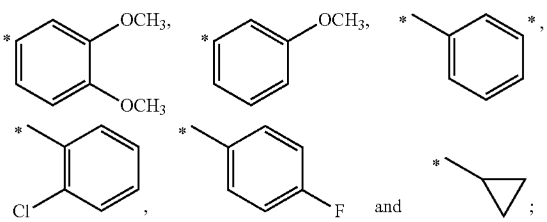

"*" represents the point of attachment as indicated in Formula I; and
$=\!=\!=$ is either a single bond or a pi-bond.

17. A method of gene editing comprising a. contacting a compound with at least one cell comprising at least one programmable nuclease, wherein the at least one programmable nuclease comprises a Cas9 endonuclease; and wherein the compound is of formula I

I

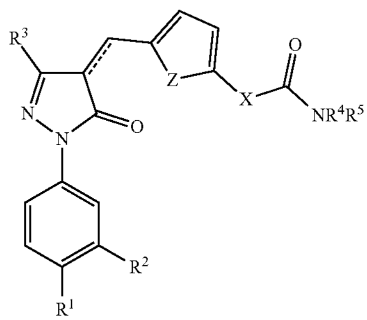

wherein

X is absent,

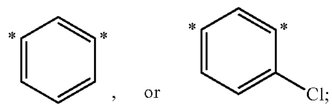 [SMILES: c1ccccc1 ; Clc1ccccc1]

Z is O or S;

$R^1$ is H, —$CO_2H$, —$S(O)_2NH_2$, or —$CO_2Et$;

$R^2$ is H, —$CO_2H$, —$CO_2Et$, —CN, or tetrazolyl;

$R^3$ is methyl;

$R^4$ is selected from the group consisting of

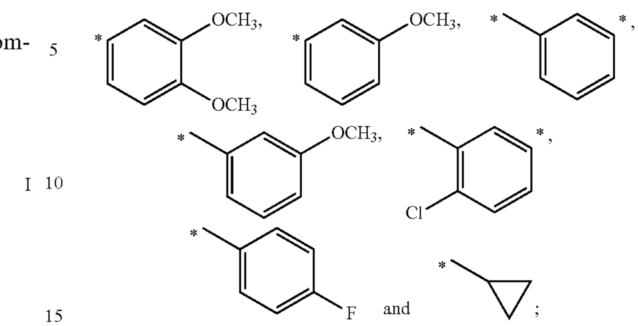

"*" represents the point of attachment as indicated in Formula I; and

═══ is either a single bond or a pi-bond; and b. contacting the at least one cell with a plasmid encoding a guide RNA (gRNA) comprising a Clustered Regularly Interspaced Short Palindromic repeat RNA (crRNA) and a trans-activating RNA (tracrRNA).

18. The method of claim 17, wherein $R^4$ is selected from the group consisting of

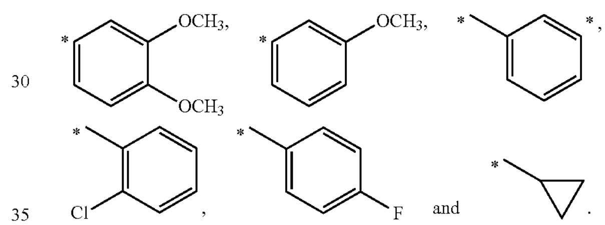

19. The method of claim 1, wherein Z is O.

20. The method of claim 17, wherein Z is O.

* * * * *